US008999973B2

(12) United States Patent
Son et al.

(10) Patent No.: US 8,999,973 B2
(45) Date of Patent: Apr. 7, 2015

(54) THIENO[3,2-D]PYRIMIDINE DERIVATIVES HAVING INHIBITORY ACTIVITY ON PROTEIN KINASES

(75) Inventors: Jung Beom Son, Hwaseong-si (KR); Seung Hyun Jung, Goyang-si (KR); Wha Il Choi, Seoul (KR); Young Hee Jung, Seoul (KR); Jae Yul Choi, Seoul (KR); Ji Yeon Song, Seoul (KR); Kyu Hang Lee, Yongin-si (KR); Jae Chul Lee, Suwon-si (KR); Eun Young Kim, Suwon-si (KR); Young Gil Ahn, Seongnam-si (KR); Maeng Sup Kim, Seoul (KR); Hwan Geun Choi, Seoul (KR); Tae Bo Sim, Seoul (KR); Young Jin Ham, Seoul (KR); Dong-sik Park, Busan (KR); Hwan Kim, Goyang-si (KR); Dong-Wook Kim, Seoul (KR)

(73) Assignees: Hanmi Science Co., Ltd, Hwaseong-si (KR); Korea Institute of Science and Technology, Seoul (KR); Catholic University Industry Academic Cooperation Foundation, Seoul (KR)

( * ) Notice: Subject to any disclaimer, the term of this patent is extended or adjusted under 35 U.S.C. 154(b) by 429 days.

(21) Appl. No.: 13/520,656

(22) PCT Filed: Jan. 31, 2011

(86) PCT No.: PCT/KR2011/000664
§ 371 (c)(1),
(2), (4) Date: Sep. 24, 2012

(87) PCT Pub. No.: WO2011/093684
PCT Pub. Date: Aug. 4, 2011

(65) Prior Publication Data
US 2013/0053370 A1    Feb. 28, 2013

(30) Foreign Application Priority Data
Jan. 29, 2010 (KR) .................. 10-2010-0008817

(51) Int. Cl.
*A61K 31/55* (2006.01)
*C07D 495/04* (2006.01)

(52) U.S. Cl.
CPC .................................. *C07D 495/04* (2013.01)

(58) Field of Classification Search
CPC .. C07D 401/12; C07D 243/08; C07D 401/14; C07D 487/04; C07D 403/12
USPC ...................... 514/218, 234.2, 260.1, 252.16; 544/117, 278
See application file for complete search history.

(56) References Cited

U.S. PATENT DOCUMENTS

| 2006/0004002 A1 | 1/2006 | Thrash et al. |
| 2007/0135455 A1 | 6/2007 | Jones et al. |
| 2009/0326224 A1 | 12/2009 | Gangjee |

FOREIGN PATENT DOCUMENTS

| JP | 2008-505186 A | 2/2008 |
| WO | 02/057271 A2 | 7/2002 |
| WO | 2007/084815 A2 | 7/2007 |
| WO | 2011025940 A1 | 3/2011 |

OTHER PUBLICATIONS

International Searching Authority, International Search Report for PCT/KR2011/000664 dated Oct. 25, 2011.
Japanese Patent Office, Communication dated Apr. 15, 2014 issued in counterpart Japanese Application No. 2012551097.
Buchanan et al., "C-Nucleoside Studies. Part 21 Synthesis of Some Hydroxyalkylated Pyrrolo-and Thieno-[3,2-d]pyrimidines Related to Known Antiviral Acyclonucleosides," J. Chem. Soc. Perkin Trans. 1, 1991, pp. 195-202.
Rheault et al., "Thienopyrimidine-based dual EGFR/ErbB-2 inhibitors," Bioorganic & Medicinal Chemistry Letters, 2009, vol. 19, No. 3, pp. 817-820.
European Patent Office, European Search Report issued in corresponding EP Application No. 11 733 323.3, dated Jul. 3, 2013.

*Primary Examiner* — Jason Sims
*Assistant Examiner* — Ibrahim D Bori
(74) *Attorney, Agent, or Firm* — Sughrue Mion, PLLC

(57) ABSTRACT

The present invention relates to a thieno[3,2-d]pyrimidine derivative of formula (I), or a pharmaceutically acceptable salt, hydrate or solvate thereof, which has an excellent inhibitory activity on protein kinases, and a pharmaceutical composition comprising the same is effective in preventing or treating abnormal cell growth diseases.

14 Claims, No Drawings

THIENO[3,2-D]PYRIMIDINE DERIVATIVES HAVING INHIBITORY ACTIVITY ON PROTEIN KINASES

CROSS REFERENCE TO RELATED APPLICATIONS

This application is a National Stage of International Application No. PCT/KR2011/000664 filed Jan. 31, 2011, claiming priority based on Korean Patent Application No. 10-2010-008817 filed Jan. 29, 2010, the contents of all of which are incorporated herein by reference in their entirety.

FIELD OF THE INVENTION

The present invention relates to novel thieno[3,2-d]pyrimidine derivatives having inhibitory activity on protein kinases and a pharmaceutical composition for preventing or treating abnormal cell growth diseases.

BACKGROUND OF THE INVENTION

Protein kinases, a catalyst enzyme for phosphorylation of hydroxyl groups in tyrosine, serine and threonine moieties of protein, play an important role in a growth factor signal transduction inducing growth, differentiation and proliferation on cells.

In order to maintain homeostasis in body, a signal transduction system in body should keep a balance between on and off. However, a mutation or an overexpression of particular protein kinases collapses the signal transduction system in a normal cell, e.g., by a continuous signal transduction in body, to induce various diseases such as cancer, inflammation, metabolic disease, and brain disease. Human protein kinases are estimated to exist in 518 species, about 1.7% of human whole genes (Manning et al., Science, 2002, 298, 1912), and largely divided into tyrosine protein kinases (at least 90 species) and serine/threonine protein kinases. Tyrosine protein kinases may be divided into receptor tyrosine kinases which are classified into 20 subtypes of 58 species and cytoplasm/non-receptors which are classified into 10 subtypes of 32 species. Receptor tyrosine kinases have domains on the cell surface for reception of growth factors, and active sites in the cytoplasm for phosphorylation of tyrosine moieties. When a growth factor binds to the growth factors receptor site on the cell surface of the receptor tyrosine kinase, the receptor tyrosine kinase forms a polymer and the tyrosine moieties of cytoplasm are autophosphorylated. Then, the signal transduction progresses inside nuclear by sequential phosphorylation of subfamily proteins, and finally, transcription factors inducing cancer are overexpressed.

A chromosome translocation between Bcr (breakpoint cluster region) genes located in chromosome 22 and Abl (V-abl Abelson murine leukemia viral oncogene homolog) genes located in chromosome 9 by chromosomal instability, generates oncogenes of Bcr-Abl genes. The Bcr-Abl chromosome translocation is called Philadelphia chromosome (Nowell and Hungerford, J. Natl. Cancer Inst., 1960; 25:85). In the Bcr-Abl gene, the Bcr part has oligomerization domains and the Abl part has tyrosine kinase domains. The size of the Bcr-Abl gene is determined by the cut position of the Bcr gene, and 3 subtypes (190, 210, 230 kDa) of Bcr-Abl genes have been reported. The Bcr-Abl gene is a leukemia-inducing factor, particularly p210-Bcr-Abl is a direct tumor factor inducing chronic myeloid leukemia (CML). The correlation between p210-Bcr-Abl and the CML induction is very high (>98%). Novartis developed Gleevec (imatinib mesylate) which can selectively inhibit Bcr-Abl, i.e., by inhibiting tyrosine kinases of Abl, and released in 2002. Gleevec, the first targeted antitumor agent, is being widely used as an initial standard therapy for treating CML due to its characteristic property and excellent stability. However, inactivation of Gleevec by the acquired resistance became a problem. The most important factor among various factors inducing the acquired resistance is point-mutation generated in the Abl kinase domains. There were attempts to overcome the acquired Gleevec-resistance by inhibiting such point-mutant species. Nilotinib and dasatinib, which are recently available, effectively inhibit many point-mutant species generated by the acquired Gleevec-resistance in Abl kinase domains. Among many point-mutant species generated by the acquired Gleevec-resistance in Abl kinase domains, the most important is T315I-Bcr-Abl mutant species wherein threonine 315 as a gate-keeper of Abl kinase is substituted with isoleucine. However, nilotinib and dasatinib are unable to inhibit T315I-Bcr-Abl mutant species. Accordingly, there are many attempts to develop a medicine inhibiting T315I-Bcr-Abl mutant species.

A vascular endothelial growth factors receptor (VEGFR) of a receptor tyrosine kinase (RTK) is an important modulator for angiogenesis. It is involved in generations of vascular and lymphatic vessel and in homeostasis as well as has an important effect on nerve cells. Vascular endothelial growth factors (VEGF) are predominantly produced by vascular endothelial, hematopoietic and stromal cells in response to hypoxia and upon stimulation with growth factors such as TGFs, interleukins or PDGF. VEGFs bind to VEGF receptor (VEGFR)-1, -2, and -3, and each VEGF isoform binds to a particular subset of these receptors giving rise to the formation of receptor homo- and heterodimers that activate discrete signaling pathways. Signal specificity of VEGF receptors is further modulated upon recruitment of coreceptors, such as neuropilins, heparan sulfate, integrins or cadherins.

The biological functions of VEGFs are mediated upon binding to type III RTKs, VEGFR-1 (Flt-1), VEGFR-2 (KDR/Flk-1) and VEGFR-3 (Flt-4). VEGFRs are closely related to Fms, Kit and PDGFRs, VEGF bind to each specific receptor, VEGF-A binds to VEGFR-1 and -2 and to receptor heterodimers, while VEGF-C and -D bind VEGFR-2 and -3. P1GF and VEGF-B exclusively bind VEGFR-1 and VEGF-E interacts only with VEGFR-2. VEGF-F variants interact with either VEGFR-1 or -2. VEGF-A, -B and P1GF are predominantly required for blood vessel formation, while VEGF-C and -D are essential for the formation of lymphatic vessels. Angiogenesis provides tumors with nutrients, oxygen, and path for cancer cell spread so as to be essential for proliferation and spread. Angiogenesis in normal body is balanced by co-regulation of angiogenic stimulators and angiogenic suppressors, while in off-balanced cancer cells VEGFR is activated by growth factors (VEGF) which have a great effect on vascular endothelial cells. Various inhibitors of VEGF receptor tyrosine kinases using low molecular synthetic materials are being developed, most of which are able to be used for solid tumors and to inhibit angiogenesis activated only in cancer cells and have an excellent medicinal effect with relatively low side effects.

Tie2, a kind of receptor tyrosine kinase, is deeply concerned with angiogenesis and vasculature. The domain structure of Tie2 is conserved in all vertebrates very well (Lyons et al., *Isolation of the zebrafish homologues for the tie-1 and tie-2 endothelium-specific receptor tyrosine kinases.*, Dev Dyn., 1998; 212:133-140). Tie2 ligands are angiopoietins (Ang). Ang2 does not induce Tie2 autophosphorylation and disturbs Tie2 activation induced by Ang1. In endothelial cells, Tie2 activation by Ang2 induces PI3K-Akt activation (Jones et al., *Identification of Tek/Tie2 binding partners. Binding to a multifunctional docking site mediates cell survival and migration.*, J Biol Chem., 1999; 274:3089630905). In mitogen-activated protein kinases (MAPK) signal transduction path as main signal transduction system of Tie2, adapter protein GRB2 and protein tyrosine phosphatase SHP2 play an important role in dimerization process by autophosphorylation of Tie2 receptor tyrosine kinases. Ang/Tie2 and vascular endothelial growth factors (VEGF) signal transduction path perform an important function in angiogenesis of cancer cells. Tie2 is manifested in vascular endothelial, particularly in the infiltration area of cancer cells. Tie2 overexpressions are found in breast cancer (Peters et al., *Expression of Tie2/Tek in breast tumour vasculature provides a new marker for evaluation of tumour angiogenesis.* Br J Cancer, 1998; 77:5156) and also in uterine cancer, liver cancer, and brain cancer.

RET (rearranged during transfection), a kind of receptor tyrosine kinases is expressed mostly in nerve cells and endocrine system. N-terminal intermolecular domains of RET consist of 4 N-cadherin-like repeats, calcium-binding sites, 9 N-glycosylation sites, and cysteine-rich regions (Aiaksinen et al., Nat. Rev. Neurosci., 2002; 3:383). The cytoplasm area of RET has at least 12 tyrosine autophosphorylation sites (Liu, J., Biol. Chem., 1996; 271:5309). For example, RET9 variants have 16 autophosphorylation sites in the kinase domain. When a GFL/GFR-alpha complex binds to the intermolecular domain of RET, RET is autophosphorylated and activated (Aiaksinen et al., Nat. Rev. Neurosci., 2002; 3:383). GFL, GNDF (glial-derived neurotropic factor)-family ligands, consists of GNDF, artemin, neurturin, and persephin. GFR-alpha having 4 subtypes of GFR-alpha1-4 is known as glycosylphosphatidylinositol-anchored co-receptor. RET plays an important role in parasympathetic, enteric nervous systems, and kidney generation of mouse (Pachnis et al., Development, 1993; 119:1005). RET defunctionalization by germline mutation induce Hirschsprung's disease which is identified as a congenital aganglionosis of distal intestines (Manie et al., Trends Genet., 2001; 17:580). However, mutations promoting the function of RET induce MEN2A (multiple endocrine neoplasia type 2A), MEN2B, and familial medullary thyroid carcinoma (FMTC). In particular, RET is proved to be a promising molecular target for development of a medicine of thyroid cancer (Cote and Gagel, N. Engl. J. Med., 2003; 349:1566).

SUMMARY OF THE INVENTION

Accordingly, it is an object of the present invention to provide novel thieno[3,2-d]pyrimidine derivatives having inhibitory activity on protein kinases.

It is another object of the present invention to provide a pharmaceutical composition for preventing or treating abnormal cell growth diseases.

In accordance with an aspect of the present invention, there is provided a thieno[3,2-d]pyrimidine derivative of formula (I), or a pharmaceutically acceptable salt, hydrate and solvate thereof:

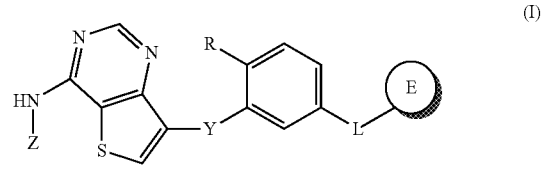

wherein,

Y is —CH=CR$^1$—, —CC—, or —C(=O)NR$^1$—;

L is —C(=O)NR$^2$—, —NR$^2$C(=O)—, or —NR$^2$C(=O)NR$^2$—;

R$^1$ and R$^2$ are each independently H, C$_{1-6}$alkyl, or C$_{3-8}$cycloalkyl;

R is H, halogen, methyl, or methoxy;

E is C$_{3-14}$aryl or C$_{2-13}$heteroaryl, which is unsubstituted or substituted by 1 to 3 substituents selected from the group consisting of halogen, —NO$_2$, —CN, —NH$_2$, —OH, —CF$_3$, C$_{1-6}$alkyl, hydroxy-C$_{1-6}$alkyl, C$_{3-8}$cycloalkyl, —(CH$_2$)$_n$—C$_{1-6}$alkylamino, —(CH$_2$)$_n$-diC$_{1-6}$alkylamino, —(CH$_2$)$_n$C$_{1-6}$alkoxy, —(CH$_2$)$_n$OS(=O)$_2$—C$_{1-6}$alkyl, —(CH$_2$)$_n$—C$_{3-14}$aryl, —(CH$_2$)$_n$—C$_{2-13}$heteroaryl and —(CH$_2$)$_n$—C$_{2-13}$heterocycloalkyl, wherein n is an integer number of 0 to 3, and the aryl, heteroaryl and heterocycloalkyl are each independently unsubstituted or substituted by a substituent selected from the group consisting of C$_{1-6}$alkyl, hydroxy-C$_{1-6}$alkyl, halogen, diC$_{1-6}$alkylamino, and C$_{1-6}$alkoxy; and Z is H, —C(=O)R$^3$, C$_{1-6}$alkyl, hydroxyC$_{1-6}$alkyl, C$_{3-8}$cycloalkyl, C$_{2-7}$heterocycloalkyl, C$_{3-14}$aryl, or C$_{2-13}$heteroaryl, wherein the aryl, heteroaryl, and heterocycloalkyl are each independently unsubstituted or substituted by C$_{1-6}$alkyl, C$_{1-6}$alkoxy, C$_{3-8}$cycloalkyl, R$^3$—C$_{2-7}$heterocycloalkyl or C$_{2-7}$heterocycloalkyl, and R$^3$ is C$_{1-6}$alkyl, C$_{3-6}$cycloalkyl, or phenyl.

In accordance with another aspect of the present invention, there is provided a pharmaceutical composition for preventing or treating abnormal cell growth diseases resulted from overexpression of a protein kinase, comprising the compound of formula (I), or a pharmaceutically acceptable salt, hydrate or solvate thereof.

The inventive thieno[3,2-d]pyrimidine derivatives, or a pharmaceutically acceptable salt, hydrate or solvate thereof has an excellent inhibitory activity on protein kinases, and a pharmaceutical composition comprising the same is effective in preventing or treating abnormal cell growth diseases.

DETAILED DESCRIPTION OF THE INVENTION

Hereinafter, the present invention is described in detail.

In the inventive compound of formula (I), E preferably is phenyl, pyridinyl, quinolinyl, isoquinolinyl, indolyl, isoxazlyl, or pyrazolyl, which is unsubstituted or substituted by 1 to 3 substituents selected from the group consisting of halogen, —NO$_2$, —CN, —NH$_2$, —OH, —CF$_3$, C$_{1-6}$alkyl, C$_{3-8}$cycloalkyl, —(CH$_2$)$_n$—C$_{1-6}$alkylamino, —(CH$_2$)$_n$-diC$_{1-6}$alkylamino, —(CH$_2$)$_n$C$_{1-6}$alkoxy, —(CH$_2$)$_n$OS(=O)$_2$—C$_{1-6}$alkyl, —(CH$_2$)$_n$—C$_{3-14}$aryl, —(CH$_2$)—C$_{2-13}$heteroaryl and —(CH$_2$)$_n$—C$_{2-13}$heterocycloalkyl, wherein n is an integer number of 0 to 3. More preferably, the aryl is phenyl; heteroaryl is pyrrolyl or imidazolyl; and heterocycloalkyl is pyrrolidinyl, piperidinyl, piperazinyl, morpholinyl, or diazepanyl, wherein said aryl, heteroaryl and heterocycloalkyl are each independently unsubstituted or substituted by $C_{1-6}$alkyl, halogen, di$C_{1-6}$alkylamino or $C_{1-6}$alkoxy.

In the inventive compound of formula (I), Z is preferably H, methyl, ethyl, 2-hydroxyethyl, 2-morpholinoethyl, isopropyl, cyclopropyl, cyclopentyl, cyclopropylcarbonyl, benzoyl, phenyl, 4-methoxyphenyl, 4-(4-methylpiperidine-1-yl)phenyl, 4-(4-ethylpiperazin-1-yl)phenyl, pyridine-4-yl, pyridine-2-yl, 5-methylpyridine-2-yl, or 6-methylpyridine-3-yl.

Preferable compound according to the present invention is a thieno[3,2-d]pyrimidine derivative selected from the group consisting of:

1) (E)-3-(2-(4-aminothieno[3,2-d]pyrimidine-7-yl)vinyl)-4-methyl-N-(3-(trifluoromethyl)phenyl)benzamide;
2) (E)-3-(2-(4-aminothieno[3,2-d]pyrimidine-7-yl)vinyl)-N-(4-((4-ethylpiperazine-1-yl)methyl)-3-(trifluoromethyl)phenyl)-4-methylbenzamide;
3) (E)-3-(2-(4-aminothieno[3,2-d]pyrimidine-7-yl)vinyl)-N-(3-(4-ethylpiperazine-1-yl)-5-(trifluoromethyl)phenyl)-4-methylbenzamide;
4) (E)-N-(3-(2-(4-aminothieno[3,2-d]pyrimidine-7-yl)vinyl)-4-methylphenyl)-3-(4-methyl-1H-imidazole-1-yl)-5-(trifluoromethyl)benzamide;
5) (E)-N-(3-(2-(4-aminothieno[3,2-d]pyrimidine-7-yl)vinyl)-4-methylphenyl)-4-(1-methylpiperidine-4-yloxy)-3-(trifluoromethyl)benzamide;
6) (E)-N-(3-(2-(4-aminothieno[3,2-d]pyrimidine-7-yl)vinyl)-4-methylphenyl)-3-(trifluoromethyl)benzamide;
7) (E)-N-(3-(2-(4-aminothieno[3,2-d]pyrimidine-7-yl)vinyl)-4-methylphenyl)-4-((4-ethylpiperazin-1-yl)methyl)-3-(trifluoromethyl)benzamide;
8) 4-amino-N-(2-methyl-5-(3-(trifluoromethyl)phenylcarbamoyl)phenyl)thieno[3,2-d]pyrimidine-7-carboxamide;
9) 4-amino-N-(5-(3-methoxyphenylcarbamoyl)-2-methylphenyl)thieno[3,2-d]pyrimidine-7-carboxamide;
10) 4-amino-N-(2-methyl-5-(3-(4-methyl-1H-imidazole-1-yl)-5-(trifluoromethyl)phenylcarbamoyl)phenyl)thieno[3,2-d]pyrimidine-7-carboxamide;
11) 4-amino-N-(5-(4-((4-ethylpiperazin-1-yl)methyl)-3-(trifluoromethyl)phenylcarbamoyl)-2-methylphenyl)thieno[3,2-d]pyrimidine-7-carboxamide
12) 4-amino-N-(5-(3,5-dimethoxyphenylcarbamoyl)-2-methylphenyl)thieno[3,2-d]pyrimidine-7-carboxamide;
13) 4-(4-methoxyphenylamino)-N-(2-methyl-5-(3-(trifluoromethyl)phenylcarbamoyl)phenyl)thieno[3,2-d]pyrimidine-7-carboxamide;
14) N-(2-methyl-5-(3-(trifluoromethyl)phenylcarbamoyl)phenyl)-4-(3,4,5-trimethoxyphenylamino)thieno[3,2-d]pyrimidine-7-carboxamide;
15) N-(2-methyl-5-(3-(trifluoromethyl)phenylcarbamoyl)phenyl)-4-(6-methylpyridine-3-ylamino)thieno[3,2-d]pyrimidine-7-carboxamide;
16) 4-(4-(4-ethylpiperazin-1-yl)phenylamino)-N-(2-methyl-5-(3-(trifluoromethyl)phenylcarbamoyl)phenyl)thieno[3,2-d]pyrimidine-7-carboxamide;
17) 4-(isopropylamino)-N-(2-methyl-5-(3-(trifluoromethyl)phenylcarbamoyl)phenyl)thieno[3,2-d]pyrimidine-7-carboxamide;
18) N-(2-methyl-5-(3-(trifluoromethyl)phenylcarbamoyl)phenyl)-4-(methylamino)thieno[3,2-d]pyrimidine-7-carboxamide;
19) 4-(2-hydroxyethylamino)-N-(2-methyl-5-(3-(trifluoromethyl)phenylcarbarnoyl)phenyl)thieno[3,2-d]pyrimidine-7-carboxamide;
20) N-(2-methyl-5-(3-(trifluoromethyl)phenylcarbamoyl)phenyl)-4-(2-morpholinoethylamino)thieno[3,2-d]pyrimidine-7-carboxamide;
21) 4-(cyclopropylamino)-N-(2-methyl-5-(3-(trifluoromethyl)phenylcarbamoyl)phenyl)thieno[3,2-d]pyrimidine-7-carboxamide;
22) 4-(cyclopropylamino)-N-(2-methyl-5-(3-(2-methyl-1H-imidazole-1-yl)-5-(trifluoromethyl)phenylcarbamoyl)phenyl)thieno[3,2-d]pyrimidine-7-carboxamide;
23) 4-(3-(4-(cyclopropylamino)thieno[3,2-d]pyrimidine-7-carboxamido)-4-methylbenzamido)-2-(trifluoromethyl)benzyl acetate;
24) 4-(cyclopropylamino)-N-(5-(4-(hydroxymethyl)-3-(trifluoromethyl)phenylcarbamoyl)-2-methylphenyl)thieno[3,2-d]pyrimidine-7-carboxamide;
25) 4-(3-(4-(cyclopropylamino)thieno[3,2-d]pyrimidine-7-carboxamido)-4-methylbenzamido)-2-(trifluoromethyl)benzyl methanesulfonate;
26) 4-(cyclopropylamino)-N-(2-methyl-5-(4-((4-methyl-1H-imidazole-1-yl)methyl)-3-(trifluoromethyl)phenylcarbamoyl)phenyl)thieno[3,2-d]pyrimidine-7-carboxamide;
27) 4-(cyclopropylamino)-N-(2-methyl-5-(3-(4-methyl-1H-imidazole-1-yl)-5-(trifluoromethyl)phenylcarbamoyl)phenyl)thieno[3,2-d]pyrimidine-7-carboxamide;
28) N-(5-(3-bromo-5-(trifluoromethylcarbamoyl)phenyl)-2-methylphenyl)-4-(cyclopropylamino)thieno[3,2-d]pyrimidine-7-carboxamide;
29) 4-(cyclopropylamino)-N-(2-methyl-5-(6-morpholinopyridine-3-ylcarbamoyl)phenyl)thieno[3,2-d]pyrimidine-7-carboxamide;
30) 4-(cyclopropylamino)-N-(5-(6-(4-ethylpiperazine-1-yl)pyridine-3-ylcarbamoyl)-2-methylphenyl)thieno[3,2-d]pyrimidine-7-carboxamide;
31) 4-(cyclopropylamino)-N-(5-(3-(2,4-dimethyl-1H-imidazole-1-yl)-5-(trifluoromethyl)phenylcarbamoyl)-2-methylphenyl)thieno[3,2-d]pyrimidine-7-carboxamide;
32) 4-(cyclopropylamino)-N-(2-methyl-5-(4-((4-methyl-1,4-diazepan-1-yl)methyl)-3-(trifluoromethyl)phenylcarbamoyl)phenyl)thieno[3,2-d]pyrimidine-7-carboxamide;
33) (S)-4-(cyclopropylamino)-N-(5-(4-((3-(dimethylamino)pyrrolidine-1-yl)methyl)-3-(trifluoromethyl)phenylcarbamoyl)-2-methylphenyl)thieno[3,2-d]pyrimidine-7-carboxamide;
34) 4-(cyclopropylamino)-N-(5-(3-(4-hydroxymethyl)-1H-imidazole-1-yl)-5-(trifluoromethyl)phenylcarbamoyl)-2-methylphenyl)thieno[3,2-d]pyrimidine-7-carboxamide;
35) 4-(cyclopropylamino)-N-(2-methyl-5-(4-(1-methylpiperidine-4-yloxy)-3-(trifluoromethyl)phenylcarbamoyl)phenyl)thieno[3,2-d]pyrimidine-7-carboxamide;
36) 4-(cyclopropylamino)-N-(2-methoxy-5-(3-(4-methyl-1H-imidazole-1-yl)-5-(trifluoromethyl)phenylcarbamoyl)phenyl)thieno[3,2-d]pyrimidine-7-carboxamide;
37) 4-(cyclopropylamino)-N-(2-methyl-5-(4-((4-methylpiperazine-1-yl)methyl)-3-(trifluoromethyl)phenylcarbamoyl)phenyl)thieno[3,2-d]pyrimidine-7-carboxamide;
38) 4-(cyclopropylamino)-N-(5-(4-((4-ethylpiperazine-1-yl)methyl)-3-(trifluoromethyl)phenylcarbamoyl)-2-methylphenyl)thieno[3,2-d]pyrimidine-7-carboxamide;
39) 4-amino-N-(2-methyl-5-(3-(trifluoromethyl)benzamido)phenyl)thieno[3,2-d]pyrimidine-7-carboxamide;
40) 4-(cyclopropylamino)-N-(2-methyl-5-(4-morpholino-3-(trifluoromethyl)benzamido)phenyl)thieno[3,2-d]pyrimidine-7-carboxamide;
41) 4-(cyclopropylamino)-N-(5-(3-(3-(dimethylamino)propylamino)-5-(trifluoromethyl)benzamido)-2-methylphenyl)thieno[3,2-d]pyrimidine-7-carboxamide;
42) 4-amino-N-(5-benzamido-2-methylphenyl)thieno[3,2-d]pyrimidine-7-carboxamide;

43) 4-amino-N-(5-(3,5-dimethoxybenzamido)-2-methylphenyl)thieno[3,2-d]pyrimidine-7-carboxamide;
44) N-(5-benzamido-2-methylphenyl)-4-(5-methylpyridin-2-ylamino)thieno[3,2-d]pyrimidine-7-carboxamide;
45) N-(5-(3-(1H-pyrrol-1-yl)-5-(trifluoromethyl)benzamido)-2-methylphenyl)-4-aminothieno[3,2-d]pyrimidine-7-carboxamide;
46) 4-amino-N-(5-(3-(dimethylamino)-5-(trifluoromethyl)benzamido)-2-methylphenyl)thieno[3,2-d]pyrimidine-7-carboxamide;
47) N-(5-(3-(1H-imidazol-1-yl)-5-(trifluoromethyl)benzamido)-2-methylphenyl)-4-aminothieno[3,2-d]pyrimidine-7-carboxamide;
48) 4-amino-N-(5-(3-fluoro-5-(trifluoromethyl)benzamido)-2-methylphenyl)thieno[3,2-d]pyrimidine-7-carboxamide;
49) 4-amino-N-(5-(4-((4-ethylpiperazine-1-yl)methyl)-3-(trifluoromethyl)benzamido)-2-methylphenyl)thieno[3,2-d]pyrimidine-7-carboxamide;
50) 1-(4-(3-(4-aminothieno[3,2-d]pyrimidine-7-carboxamido)-4-methylphenylcarbamoyl)-2-(trifluoromethyl)benzyl)piperidine-4-yl acetate;
51) N-(2-methyl-5-(3-(trifluoromethyl)benzamido)phenyl)-4-(phenylamino)thieno[3,2-d]pyrimidine-7-carboxamide;
52) N-(2-methyl-5-(3-(trifluoromethyl)benzamido)phenyl)-4-(pyridine-4-ylamino)thieno[3,2-d]pyrimidine-7-carboxamide;
53) N-(2-methyl-5-(3-(trifluoromethyl)benzamido)phenyl)-4-(pyridine-2-ylamino)thieno[3,2-d]pyrimidine-7-carboxamide;
54) 4-amino-N-(5-(isoquinoline-1-carboxyamido)-2-methylphenyl)thieno[3,2-d]pyrimidine-7-carboxamide;
55) 4-amino-N-(5-(isoquinoline-3-carboxyamido)-2-methylphenyl)thieno[3,2-d]pyrimidine-7-carboxamide;
56) 4-amino-N-(5-(4-methoxyquinoline-2-carboxyamido)-2-methylphenyl)thieno[3,2-d]pyrimidine-7-carboxamide;
57) N-(5-(1H-indole-2-carboxyamido)-2-methylphenyl)-4-aminothieno[3,2-d]pyrimidine-7-carboxamide;
58) 4-amino-N-(2-methyl-5-(picolinamido)phenyl)thieno[3,2-d]pyrimidine-7-carboxamide;
59) 4-amino-N-(2-methyl-5-(nicotinamido)phenyl)thieno[3,2-d]pyrimidine-7-carboxamide;
60) 4-amino-N-(5-(isonicotinamido)-2-methylphenyl)thieno[3,2-d]pyrimidine-7-carboxamide;
61) 4-amino-N-(2-methyl-5-(3-(2-methyl-1H-imidazole-1-yl)-5-(trifluoromethyl)benzamido)phenyl)thieno[3,2-d]pyrimidine-7-carboxamide;
62) 4-amino-N-(5-(3-fluorophenylamido)-2-methylphenyl)thieno[3,2-d]pyrimidine-7-carboxamide;
63) 4-amino-N-(2-methyl-5-(2-(trifluoromethyl)benzamido)phenyl)thieno[3,2-d]pyrimidine-7-carboxamide;
64) (R)-4-amino-N-(5-(3-(3-(dimethylamino)pyrrolidine-1-yl)-5-(trifluoromethyl)benzamido)-2-methylphenyl)thieno[3,2-d]pyrimidine-7-carboxamide;
65) 4-amino-N-(5-(3-methoxybenzamido)-2-methylphenyl)thieno[3,2-d]pyrimidine-7-carboxamide;
66) 4-amino-N-(2-methyl-5-(4-(trifluoromethyl)benzamido)phenyl)thieno[3,2-d]pyrimidine-7-carboxamide;
67) N-(3-(4-aminothieno[3,2-d]pyrimidine-7-carboxyamido)-4-methylphenyl)-5-cyclopropylisoxazol-3-carboxamide;
68) 4-amino-N-(5-(1-(4-fluorobenzyl)-3-methyl-1H-pyrazole-5-carboxyamido)-2-methylphenyl)thieno[3,2-d]pyrimidine-7-carboxamide;
69) N-(2-methyl-5-(3-(trifluoromethyl)benzamido)phenyl)-4-(methylamino)thieno[3,2-d]pyrimidine-7-carboxamide;
70) 4-(cycloamino)-N-(2-methyl-5-(3-(trifluoromethyl)benzamido)phenyl)thieno[3,2-d]pyrimidine-7-carboxamide;
71) 4-(cyclopentylamino)-N-(2-methyl-5-(3-(trifluoromethyl)benzamido)phenyl)thieno[3,2-d]pyrimidine-7-carboxamide;
72) N-(2-methyl-5-(3-(trifluoromethyl)benzamido)phenyl)-4-(6-methylpyridine-3-ylamino)thieno[3,2-d]pyrimidine-7-carboxamide;
73) 4-(4-(4-ethylpiperazine-1-yl)phenylamino)-N-(2-methyl-5-(3-(trifluoromethyl)benzamido)phenyl)thieno[3,2-d]pyrimidine-7-carboxamide;
74) 4-(cyclopropylamino)-N-(2-methyl-5-(3-(4-methyl-1H-imidazole-1-yl)-5-(trifluoromethyl)benzamido)phenyl)thieno[3,2-d]pyrimidine-7-carboxamide;
75) 4-(cyclopropylamino)-N-(2-methyl-5-(4-(4-methylpiperazin-1-yl)-3-(trifluoromethyl)benzamido)phenyl)thieno[3,2-d]pyrimidine-7-carboxamide;
76) (S)-4-(cyclopropylamino)-N-(5-(4-((3-(dimethylamino)pyrrolidin-1-yl)methyl)-3-(trifluoromethyl)benzoamido)-2-methylphenyl)thieno[3,2-d]pyrimidine-7-carboxamide;
77) 4-(cyclopropylamino)-N-(2-methyl-5-(4-((4-methyl-1H-imidazole-1-yl)methyl)-3-(trifluoromethyl)benzoamido)phenyl)thieno[3,2-d]pyrimidine-7-carboxamide;
78) N-(2-methyl-5-(3-(4-methyl-1H-imidazole-1-yl)-5-(trifluoromethyl)benzoamido)phenyl)-4-(methylamino)thieno[3,2-d]pyrimidine-7-carboxamide;
79) 4-(ethylamino)-N-(2-methyl-5-(3-(4-methyl-1H-imidazole-1-yl)-5-(trifluoromethyl)benzoamido)phenyl)thieno[3,2-d]pyrimidine-7-carboxamide;
80) 4-(cyclopentylamino)-N-(2-methyl-5-(3-(4-methyl-1H-imidazole-1-yl)-5-(trifluoromethyl)benzoamido)phenyl)thieno[3,2-d]pyrimidine-7-carboxamide;
81) N-(2-methyl-5-(3-(4-methyl-1H-imidazole-1-yl)-5-(trifluoromethyl)benzoamido)phenyl)-4-(4-(4-methylpiperazin-1-yl)phenylamino)thieno[3,2-d]pyrimidine-7-carboxamide;
82) 4-(cyclopropylamino)-N-(2-methyl-5-(4-(4-methyl-1H-imidazole-1-yl)-3-(trifluoromethyl)benzoamido)phenyl)thieno[3,2-d]pyrimidine-7-carboxamide;
83) 4-(cyclopropylamino)-N-(2-methyl-5-(3-(2-methyl-1H-imidazole-1-yl)-5-(trifluoromethyl)benzoamido)phenyl)thieno[3,2-d]pyrimidine-7-carboxamide;
84) (R)-4-(cyclopropylamino)-N-(5-(3-(3-(dimethylamino)pyrrolidine-1-yl)-5-(trifluoromethyl)benzoamido)-2-methylphenyl)thieno[3,2-d]pyrimidine-7-carboxamide;
85) 4-(cyclopropylamino)-N-(2-methyl-5-(3-(4-methylpiperazin-1-yl)-5-(trifluoromethyl)benzoamido)phenyl)thieno[3,2-d]pyrimidine-7-carboxamide;
86) 4-(cyclopropylamino)-N-(2-methyl-5-(3-(morpholino-5-(trifluoromethyl)benzoamido)phenyl)thieno[3,2-d]pyrimidine-7-carboxamide;
87) 4-(cyclopropylamino)-N-(2-methyl-5-(4-((4-methyl-1,4-diazepan-1-yl)methyl)-3-(trifluoromethyl)benzoamido)phenyl)thieno[3,2-d]pyrimidine-7-carboxamide;
88) 4-(cyclopropylamino)-N-(5-(4-(2,4-dimethyl-1H-imidazole-1-yl)-3-(trifluoromethyl)benzoamido)-2-methylphenyl)thieno[3,2-d]pyrimidine-7-carboxamide;
89) 4-(cyclopropylamino)-N-(2-fluoro-5-(3-(4-methyl-1,4-diazepane-1-yl)-5-(trifluoromethyl)benzoamido)phenyl)thieno[3,2-d]pyrimidine-7-carboxamide;
90) 4-(cyclopropylamino)-N-(5-(3-(2,4-dimethyl-1H-imidazole-1-yl)-5-(trifluoromethyl)benzoamido)-2-methylphenyl)thieno[3,2-d]pyrimidine-7-carboxamide;
91) N-(5-(3-(1H-imidazole-1-yl)-5-(trifluoromethyl)benzoamido)-2-methylphenyl)-4-(cyclopropylamino)thieno[3,2-d]pyrimidine-7-carboxamide;

92) (S)-4-(cyclopropylamino)-N-(5-(3-(3-(dimethylamino) pyrrolidin-1-yl)-5-(trifluoromethyl)benzoamido)-2-methylphenyl)thieno[3,2-d]pyrimidine-7-carboxamide;

93) 4-(cyclopropylamino)-N-(2-methyl-5-(3-(4-methyl-1,4-diazepan-1-yl)-5-(trifluoromethyl)benzoamido)phenyl) thieno[3,2-d]pyrimidine-7-carboxamide;

94) (R)-4-(cyclopropylamino)-N-(5-(4-(3-(dimethylamino) pyrrolidine-1-yl)-3-(trifluoromethyl)benzoamido)-2-methylphenyl)thieno[3,2-d]pyrimidine-7-carboxamide;

95) (S)-4-(cyclopropylamino)-N-(5-(4-(3-(dimethylamino) pyrrolidine-1-yl)-3-(trifluoromethyl)benzoamido)-2-methylphenyl)thieno[3,2-d]pyrimidine-7-carboxamide;

96) N-(2-methyl-5-(3-(4-methyl-1H-imidazole-1-yl)-5-(trifluoromethyl)benzoamido)phenyl)-4-(1-methylpiperidine-4-ylamino)thieno[3,2-d]pyrimidine-7-carboxamide;

97) 4-(cyclopropylamino)-N-(5-(4-(diethylamino)-3-(trifluoromethyl)benzoamido)-2-methylphenyl)thieno[3,2-d] pyrimidine-7-carboxamide;

98) 4-(cyclopropylamino)-N-(2-methyl-5-(4-(1-methylpiperidine-4-ylamino)-3-(trifluoromethyl)benzoamido)phenyl)thieno[3,2-d]pyrimidine-7-carboxamide;

99) N-(2-chloro-5-(3-(4-methyl-1H-imidazole-1-yl)-5-(trifluoromethyl)benzoamido)phenyl)-4-(cyclopropylamino) thieno[3,2-d]pyrimidine-7-carboxamide;

100) (R)-4-(cyclopropylamino)-N-(5-(4-(3-(dimethylamino) pyrrolidine-1-yl)-3-(trifluoromethyl)benzoamido)-2-fluorophenyl)thieno[3,2-d]pyrimidine-7-carboxamide;

101) N-(2-chloro-5-(3-(2,4-dimethyl-1H-imidazole-1-yl)-5-(trifluoromethyl)benzoamido)phenyl)-4-(cyclopropylamino)thieno[3,2-d]pyrimidine-7-carboxamide;

102) 4-(cyclopropylamino)-N-(2-methyl-5-(3-(morpholinoamino)-5-(trifluoromethyl)benzoamido)phenyl)thieno [3,2-d]pyrimidine-7-carboxamide;

103) N-(2-methyl-5-(3-(4-methyl-1H-imidazole-1-yl)-5-(trifluoromethyl)benzoamido)phenyl)-4-(phenylamino) thieno[3,2-d]pyrimidine-7-carboxamide;

104) 4-(cyclopropylamino)-N-(2-fluoro-5-(4-(4-methylpiperazine-1-yl)-3-(trifluoromethyl)benzoamido)phenyl) thieno[3,2-d]pyrimidine-7-carboxamide 105) 4-(cyclopropylamino)-N-(5-(3-(2-(dimethylamino) ethylamino)-5-(trifluoromethyl)benzoamido)-2-methylphenyl)thieno[3,2-d]pyrimidine-7-carboxamide;

106) (S)-4-(cyclopropylamino)-N-(5-(4-(3-(dimethylamino) pyrrolidine-1-yl)-3-(trifluoromethyl)benzoamido)-2-fluorophenyl)thieno[3,2-d]pyrimidine-7-carboxamide;

107) (S)-4-(cyclopropylamino)-N-(5-(3-(3-(dimethylamino) pyrrolidine-1-yl)-5-(trifluoromethyl)benzoamido)-2-fluorophenyl)thieno[3,2-d]pyrimidine-7-carboxamide;

108) 4-(cyclopropylamino)-N-(5-(3-(2,4-dimethyl-1H-imidazole-1-yl)-5-(trifluoromethyl)benzoamido)-2-fluorophenyl)thieno[3,2-d]pyrimidine-7-carboxamide;

109) 4-(cyclopropylamino)-N-(2-methyl-5-(3-(piperidine-1-yl)-5-(trifluoromethyl)benzoamido)phenyl)thieno[3,2-d] pyrimidine-7-carboxamide;

110) 4-(cyclopropylamino)-N-(5-(3-(4-ethylpiperazin-1-yl)-5-(trifluoromethyl)benzoamido)-2-methylphenyl)thieno [3,2-d]pyrimidine-7-carboxamide;

111) 4-(cyclopropylamino)-N-(2-methyl-5-(4-(1-methylpiperidine-4-yloxy)-3-(trifluoromethyl)benzoamido)phenyl) thieno[3,2-d]pyrimidine-7-carboxamide;

112) 4-(cyclopropylamino)-N-(2-methyl-5-(3-(pyrrolidine-1-yl)-5-(trifluoromethyl)benzoamido)phenyl)thieno[3,2-d]pyrimidine-7-carboxamide;

113) (R)-4-(cyclopropylamino)-N-(2-methyl-5-(3-(2-methylpyrrolidine-1-yl)-5-(trifluoromethyl)benzoamido)phenyl)thieno[3,2-d]pyrimidine-7-carboxamide;

114) 4-(cyclopropylamino)-N-(5-(3-(diethylamino)-5-(trifluoromethyl)benzoamido)-2-methylphenyl)thieno[3,2-d] pyrimidine-7-carboxamide;

115) 4-(cyclopropylamino)-N-(5-(3-(ethylamino)-5-(trifluoromethyl)benzoamido)-2-methylphenyl)thieno[3,2-d]pyrimidine-7-carboxamide;

116) 4-(cyclopropylamino)-N-(2-methyl-5-(3-(1-methylpiperidine-4-ylamino)-5-(trifluoromethyl)benzoamido)phenyl)thieno[3,2-d]pyrimidine-7-carboxamide;

117) 4-(cyclopropylamino)-N-(3-(3-(4-methyl-1H-imidazole-1-yl)-5-(trifluoromethyl)benzoamido)phenyl)thieno [3,2-d]pyrimidine-7-carboxamide;

118) 4-(cyclopropylamino)-N-(2-methoxy-5-(3-(4-methyl-1H-imidazole-1-yl)-5-(trifluoromethyl)benzoamido)phenyl)thieno[3,2-d]pyrimidine-7-carboxamide;

119) 4-(cyclopropylcarboxyamido)-N-(2-methyl-5-(3-(4-methyl-1H-imidazole-1-yl)-5-(trifluoromethyl)benzoamido)phenyl)thieno[3,2-d]pyrimidine-7-carboxamide;

120) 4-benzoamido-N-(2-methyl-5-(3-(4-methyl-1H-imidazole-1-yl)-5-(trifluoromethyl)benzoamido)phenyl)thieno [3,2-d]pyrimidine-7-carboxamide;

121) 4-(cyclopropylamino)-N-(2-fluoro-5-(3-(4-methyl-1H-imidazole-1-yl)-5-(trifluoromethyl)benzoamido)phenyl) thieno[3,2-d]pyrimidine-7-carboxamide;

122) 4-amino-N-(5-(3-(4-chloro-3-(trifluoromethyl)phenyl) ureido)-2-methylphenyl)thieno[3,2-d]pyrimidine-7-carboxamide;

123) 4-(cyclopropylamino)-N-(2-methyl-5-(3-(3-(4-methyl-1H-imidazole-1-yl)-5-(trifluoromethyl)phenyl)ureido) phenyl)thieno[3,2-d]pyrimidine-7-carboxamide;

124) 3-((4-(cyclopropylamino)thieno[3,2-d]pyrimidine-7-yl)ethynyl)-4-methyl-N-(3-(4-methyl-1H-imidazole-1-yl)-5-(trifluoromethyl)phenyl)benzamide;

125) N-(3-((4-(cyclopropylamino)thieno[3,2-d]pyrimidine-7-yl)ethynyl)-4-methylphenyl)-3-(4-methyl-1H-imidazole-1-yl)-5-(trifluoromethyl)benzamide;

126) 3-((4-(cyclopropylamino)thieno[3,2-d]pyrimidine-7-yl)ethynyl)-4-methyl-N-(4-((4-methylpiperazine-1-yl) methyl)-3-(trifluoromethyl)phenyl)benzamide;

127) 3-((4-(cyclopropylamino)thieno[3,2-d]pyrimidine-7-yl)ethynyl)-N-(4-((4-ethylpiperazine-1-yl)methyl)-3-(trifluoromethyl)phenyl)-4-methylbenzamide;

128) 3-((4-(cyclopropylamino)thieno[3,2-d]pyrimidine-7-yl)ethynyl)-4-methyl-N-(4-(1-methylpiperazine-1-yloxy)-3-(trifluoromethyl)phenyl)benzamide; and a pharmaceutically acceptable salt, hydrate and solvate thereof.

In preparation of the inventive compound of formula (I), the starting material or intermediate may be the compounds of formulas (II) to (V):

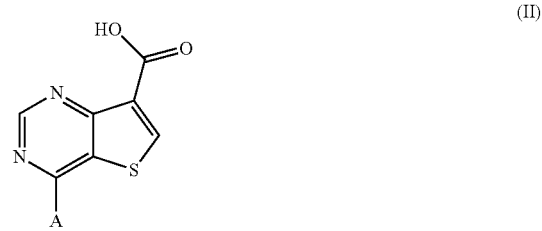

-continued

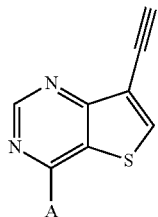
(III)

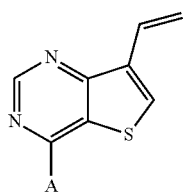
(IV)

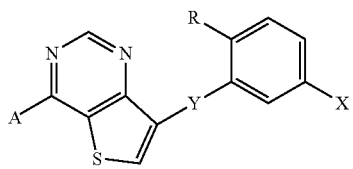
(V)

wherein,

A is halogen, —OR$^4$, —SR$^4$, —S(=O)R$^4$, —S(=O)$_2$R$^4$, —NR$^4$R$^5$, or —NR$^4$C(=O)R$^5$;

R$^4$ and R$^5$ are each independently H, C$_{1-6}$alkyl, C$_{3-8}$cycloalkyl, —C(=O)R$^6$, C$_{2-7}$heterocycloalkyl, C$_{3-14}$aryl, or C$_{2-13}$heteroaryl, wherein the aryl, heteroaryl and heterocycloalkyl are each independently unsubstituted or substituted by the substituent selected from the group consisting of C$_{1-6}$alkyl, C$_{2-7}$cycloalkyl, C$_{1-6}$alkoxy and C$_{2-7}$heterocycloalkyl;

R$^6$ is H, C$_{1-6}$alkyl or C$_{2-7}$cycloalkyl.

X is —NH$_2$ or —C(O)OH;

Y is —CHCR$^7$—, —CC—, or —C(O)NR$^7$—, wherein R$^7$ is H, C$_{1-6}$alkyl or C$_{3-8}$cycloalkyl; and R is H, halogen, methyl or methoxy.

The inventive compound of formula (I), or a pharmaceutically acceptable salt, hydrate or solvate thereof exhibits an excellent inhibitory activity on protein kinases.

Accordingly, the present invention provides a pharmaceutical composition for preventing or treating abnormal cell growth diseases resulted from overexpression of a protein kinase, comprising the compound of formula (I), or a pharmaceutically acceptable salt, hydrate or solvate thereof as an active ingredient.

The protein kinase may comprise Bcr-Abl, FGFR, Flt, KDR, PDGFR, Fms, Kit, Raf, Tie2, Src, and Ret. The pharmaceutical composition of the present invention has an excellent inhibitory activity on these kinases.

The abnormal cell growth disease may comprise stomach cancer, lung cancer, liver cancer, colorectal cancer, small intestinal cancer, pancreatic cancer, brain cancer, bone cancer, melanoma, breast cancer, sclerosing adenosis, uterine cancer, uterine cervical cancer, head and neck cancer, esophageal cancer, thyroid cancer, parathyroid cancer, renal cancer, sarcoma, prostate cancer, urethra cancer, bladder cancer, blood cancer, lymphoma, psoriasis and fibroadenoma.

For example, the blood cancer may be leukemia, multiple myeloma or myelodysplastic syndrome; and the lymphoma may be Hodgkin's disease or non-Hodgkin's lymphoma.

Accordingly, the present invention provides a method for preventing or treating abnormal cell growth diseases resulted from overexpression of a protein kinase, comprising administering the compound of formula (I), or a pharmaceutically acceptable salt, hydrate or solvate thereof to a subject requiring prevention or treatment of abnormal cell growth diseases resulted from overexpression of a protein kinase.

A proposed daily dose of the inventive compound for administration to a human (of approximately 70 kg body weight) may be in the range of 1 mg/day to 2,000 mg/day. The inventive compound may be administered in a single dose or in divided doses per day. It is understood that the daily dose should be determined in light of various relevant factors including the condition, age, body weight and sex of the subject to be treated, administration route, and disease severity; and, therefore, the dosage suggested above should not be construed to limit the scope of the present invention in anyway.

The present invention provides thieno[3,2-d]pyrimidine derivatives represented by formula (I) or a pharmaceutically acceptable salt thereof. The pharmaceutically acceptable salt should have a low toxicity in human and should not adversely affect the biological activity and physicochemical properties of the parent compound. The pharmaceutically acceptable salts comprise an acid addition salt of a pharmaceutically acceptable free acid and a base compound of formula (I); an alkali metal salt (e.g., sodium salt) and an alkaline earth metal salt (e.g., calcium salt); an organic base addition salt of an organic base and a carboxylic acid compound of formula (I); and an amino acid addition salt.

Preferable salt forms of inventive compound comprise a salt formed with an inorganic acid or an organic acid. Examples of the inorganic acid are hydrochloric acid, sulfuric acid, nitric acid, phosphoric acid, perchloric acid, and bromic acid. Examples of the organic acid are acetic acid, methanesulfonic acid, ethanesulfonic acid, p-toluenesulfonic acid, fumaric acid, malic acid, malonic acid, phthalic acid, succinic acid, lactic acid, citric acid, gluconic acid, tartaric acid, salicylic acid, maleic acid, oxalic acid, benzoic acid, aspartic acid, and glutamic acid. The organic base addition salt may be prepared using an organic base such as tris(hydroxymethyl) methylamine and dicyclohexylamine. The amino acid addition salt may be prepared using a natural amino acid such as alanine and glycine.

These salts may be prepared in a conventional manner. For example, the salts may be prepared by dissolving the compound of formula (I) in a water-miscible solvent such as methanol, ethanol, acetone and 1,4-dioxane; adding a free acid or free base thereto; and then crystallizing.

The pharmaceutical composition of the present invention comprising the bicyclic heteroaryl derivatives represented by formula (I), a pharmaceutically acceptable salt, solvate or hydrate thereof as an active ingredient, may further contain a conventional non-toxic pharmaceutically acceptable carrier, a reinforcing agent, or a diluent, to be formulated for parenteral administration or oral administration, e.g., in the form of a tablet, capsule, troches, solution or suspension.

The pharmaceutical composition of the present invention may comprise conventional additives such as a diluent, a sweetener, a binder, a solubilizing agent, a solubilizing co-agent, a wetting agent, an emulsifier, an isoosmotic agent, an absorbent, a disintegrator, an antioxidant, a preservative, a lubricant, a filler, and an aromatics. Examples of the additives are lactose, dextrose, sucrose, mannitol, sorbitol, cellulose, glycine, silica, talc, stearic acid, sterin, magnesium stearate, magnesium aluminum silicate, starch, gelatin, tragacanth gum, alginic acid, sodium alginate, methyl cellulose, sodium carboxymethyl cellulose, agar, water, ethanol, polyethylene glycol, polyvinyl pyrrolidone, sodium chloride, calcium chloride, orange essence, strawberry essence, vanilla essence, etc.

Examples of the carrier employed in the injectable composition of the present invention are distilled water, a saline solution, a glucose solution, a glucose-like solution, alcohol, glycol ether (e.g., polyethylene glycol 400), oil, fatty acid, fatty acid ester, glyceride, a surfactant, a suspension agent and an emulsifier.

The following Examples are intended to further illustrate the present invention without limiting its scope.

The compound of Preparation Example 1 was prepared according to Reaction Scheme 1 below:

Reaction Scheme 1

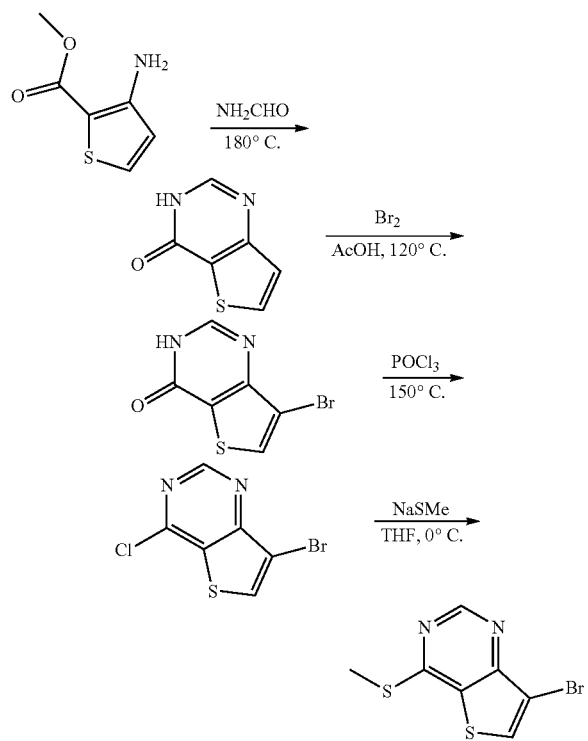

Preparation Example 1

7-Bromo-4-(methylthio)thieno[3,2-d]pyrimidine

Step 1: Thieno[3,2-d]pyrimidine-4(3H)-one

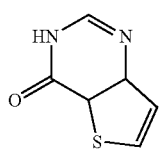

Methyl-3-aminothiophene-2-carboxylate (15 g, 98.57 mmol) (Matrix, Cat #018289, CAS [22288-78-4]) was dissolved in formamide (50 mL), and the mixture was stirred at 180° C. for 5 hours. The reaction mixture was further stirred at room temperature for 2 hours and then filtered to obtain the title compound.

$^1$H NMR (400 MHz, DMSO-$d_6$) δ 12.48 (br, 1H), 8.18 (d, J=5.1 Hz, 1H), 8.14 (s, 1H), 7.40 (d, J=5.1 Hz, 1H).

Step 2: 7-Bromothieno[3,2-d]pyrimidine-4(3H)-one

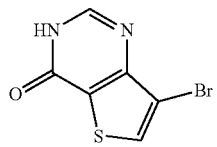 [SMILES: O=c1[nH]cnc2c(Br)csc12]

Thieno[3,2-d]pyrimidine-4(3H)-one (4.9 g) was dissolved in acetic acid (20 mL) and then brome (5 mL) was added thereto. In a sealed reactor, the reaction mixture was stirred at 120° C. for 10 hours. The reaction mixture was cooled to room temperature and distilled under reduced pressure to remove acetic acid. The resulting mixture was added to ice water and the resulting solid was filtered and then dried to obtain the title compound without further purification.

$^1$H NMR (400 MHz, DMSO-$d_6$) δ 12.75 (brs, 1H), 8.36 (s, 1H), 8.24 (s, 1H).

Step 3: 7-Bromo-4-chlorothieno[3,2-d]pyrimidine

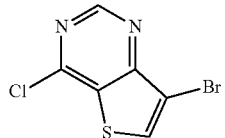 [SMILES: Clc1ncnc2c(Br)csc12]

7-Bromothieno[3,2-d]pyrimidine-4(3H)-one (5.9 g) was dissolved in POCl$_3$ (20 mL) and then stirred at 150° C. for 3 hours. After cooling down to room temperature, the remaining POCl$_3$ was concentrated and added to ice water to obtain a solid. The solid was washed with sat. NaHCO$_3$ solution and dried with N$_2$ gas to obtain the title compound.

$^1$H NMR (400 MHz, DMSO-$d_6$) δ 9.16 (s, 1H), 8.79 (s, 1H).

Step 4: 7-Bromo-4-(methylthio)thieno[3,2-d]pyrimidine

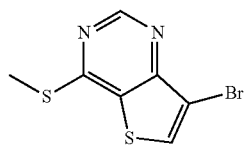

7-Bromo-4-chlorothieno[3,2-d]pyrimidine (2 g, 8.07 mmol) was dissolved in THF (27 mL) and then NaSMe (650 mg, 9.28 mmol) was added at 0° C. thereto. After stirring for 15 hours, ice water was added thereto. The resulting solid was filtered and dried with N$_2$ gas to obtain the title compound without further purification.

$^1$H NMR (400 MHz, DMSO-$d_6$) δ 9.09 (s, 1H), 8.57 (s, 1H), 2.76 (s, 3H).

The compound of Example 1 was prepared according to Reaction Scheme 2 below:

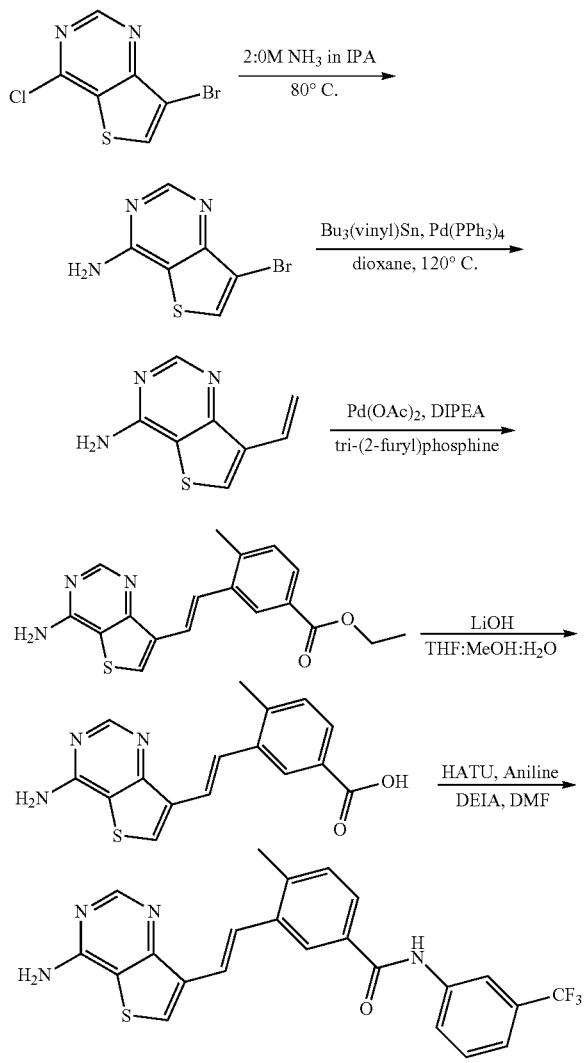

Reaction Scheme 2

Example 1

(E)-3-(2-(4-aminothieno[3,2-d]pyrimidine-7-yl)vinyl)-4-methyl-N-(3-(trifluoromethyl)phenyl)benzamide Step 1: 7-Bromothieno[3,2-d]pyrimidine-4-amine

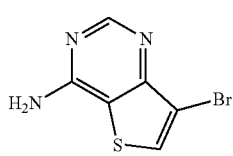

7-Bromo-4-chlorothieno[3,2-d]pyrimidine (5 g, 20.17 mmol) obtained in Step 3 of Preparation Example 1 and 2.0M NH$_3$ dissolved in isopropanol solution (50 mL) were added to a sealed reaction vessel and stirred at 100° C. for 12 hours. The reaction mixture was cooled to room temperature and filtered to obtain a solid. The solid was washed with water and dried with N$_2$ gas to obtain the title compound (3.8 g, 83%) without further purification.

MS m/z [M+1] 229.97, 231.98.

Step 2: 7-Vinylthieno[3,2-d]pyrimidine-4-amine

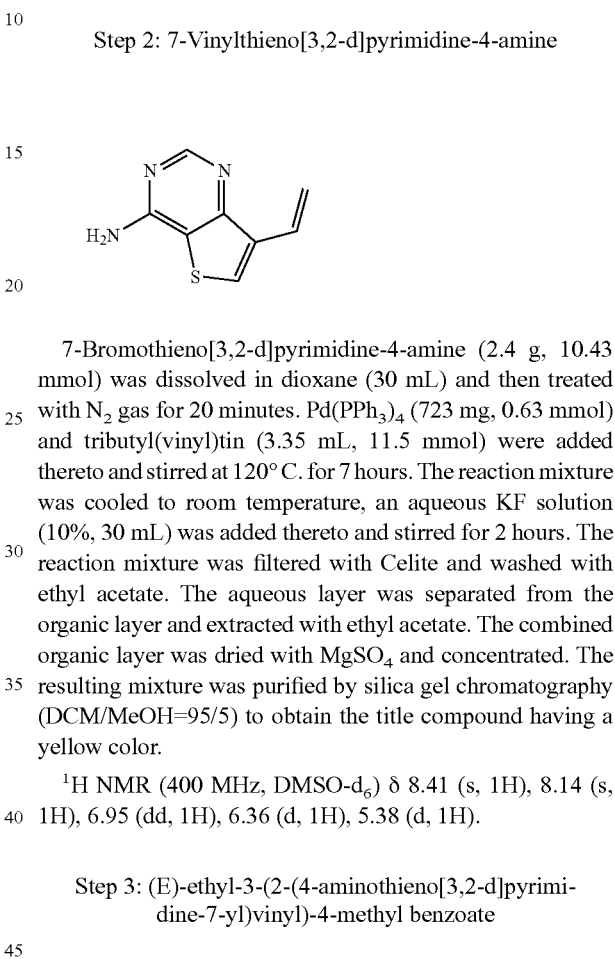

7-Bromothieno[3,2-d]pyrimidine-4-amine (2.4 g, 10.43 mmol) was dissolved in dioxane (30 mL) and then treated with N$_2$ gas for 20 minutes. Pd(PPh$_3$)$_4$ (723 mg, 0.63 mmol) and tributyl(vinyl)tin (3.35 mL, 11.5 mmol) were added thereto and stirred at 120° C. for 7 hours. The reaction mixture was cooled to room temperature, an aqueous KF solution (10%, 30 mL) was added thereto and stirred for 2 hours. The reaction mixture was filtered with Celite and washed with ethyl acetate. The aqueous layer was separated from the organic layer and extracted with ethyl acetate. The combined organic layer was dried with MgSO$_4$ and concentrated. The resulting mixture was purified by silica gel chromatography (DCM/MeOH=95/5) to obtain the title compound having a yellow color.

$^1$H NMR (400 MHz, DMSO-d$_6$) δ 8.41 (s, 1H), 8.14 (s, 1H), 6.95 (dd, 1H), 6.36 (d, 1H), 5.38 (d, 1H).

Step 3: (E)-ethyl-3-(2-(4-aminothieno[3,2-d]pyrimidine-7-yl)vinyl)-4-methyl benzoate

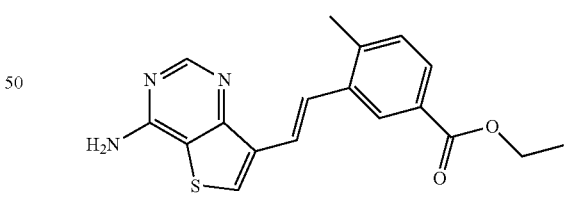

7-Vinylthieno[3,2-d]pyrimidine-4-amine (2.5 g, 14.12 mmol), ethyl-3-iodo-4-methyl benzoate (4.1 g, 14.12 mmol), Pd(OAc)$_2$ (190 mg, 0.85 mmol), tri-(2-furyl)phosphine (295 mg, 1.27 mmol), and DIEA (4.7 mL, 28.24 mmol) were dissolved in DMF (47 mL) and then stirred at 120° C. for 18 hr. The reaction mixture was filtered and extracted with ethyl acetate. The organic layer was washed with brine, dried with MgSO$_4$, filtered and concentrated. The resulting mixture was purified by silica gel chromatography to obtain the title compound (3.3 g, yield 69%).

¹H NMR (400 MHz, DMSO-d₆) δ 8.48 (s, 1H), 8.34 (s, 1H), 8.19 (s, 1H), 8.14 (d, 1H), 7.75 (d, 1H), 7.50 (s, 2H), 7.39 (d, 1H), 7.36 (d, 1H), 4.32 (q, 2H), 2.49 (s, 3H), 1.32 (t, 3H); MS m/z [M+1] 340.28.

Step 4: (E)-3-(2-(4-aminothieno[3,2-d]pyrimidine-7-yl)vinyl)-4-methylbenzoic acid

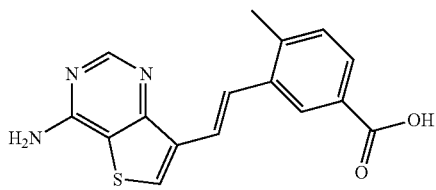 [SMILES: Cc1ccc(C(=O)O)cc1/C=C/c1csc2c(N)ncnc12]

(E)-ethyl-3-(2-(4-aminothieno[3,2-d]pyrimidine-7-yl)vinyl)-4-methyl benzoate (3.0 g, 8.84 mmol) was dissolved in a mixture of methanol (15 mL) and THF (15 mL) and LiOH (1.8 g, 44.19 mmol) dissolved in water (15 mL) was added thereto. The reaction mixture was stirred at room temperature for 18 hours. The organic layer was concentrated and 1N HCl solution was added dropwise thereto to obtain a solid. The solid was filtered and dried with N₂ gas to obtain the title compound (2.45 g, 89% yield) without further purification.
MS m/z [M+1] 312.17.

Step 5: (E)-3-(2-(4-aminothieno[3,2-d]pyrimidine-7-yl)vinyl)-4-methyl-N-(3-(trifluoromethyl)phenyl)benzamide

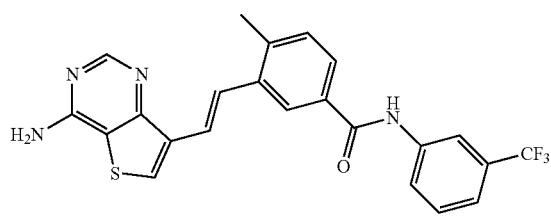 [SMILES: Cc1ccc(C(=O)Nc2cccc(C(F)(F)F)c2)cc1/C=C/c1csc2c(N)ncnc12]

(E)-3-(2-(4-aminothieno[3,2-d]pyrimidine-7-yl)vinyl)-4-methylbenzoic acid (30 mg, 0.096 mmol) was dissolved in DMF (1 mL), 3-(trifluoromethyl)benzeneamine (16 mg, 0.096 mmol), HATU (110 mg, 0.289 mmol) and TEA (67 μL, 0.48 mmol) was added thereto and stirred at room temperature for 18 hours. The reaction mixture was diluted with ethyl acetate and washed with brine. The organic layer was dried with MgSO₄, filtered and concentrated. The resulting mixture was purified by silica gel chromatography to obtain the title compound (36 mg, 82% yield).
MS m/z [M+1] 455.20.

Example 2

(E)-3-(2-(4-aminothieno[3,2-d]pyrimidine-7-yl)vinyl)-N-(4-((4-ethylpiperazine-1-yl)methyl)-3-(trifluoromethyl)phenyl)-4-methylbenzamide The procedure of Step 5 of Example 1 was repeated except for using (E)-3-(2-(4-aminothieno[3,2-d]pyrimidine-7-yl)vinyl)-4-methylbenzoic acid and 4-((4-ethylpiperazine-1-yl)methyl)-3-(trifluoromethyl)aniline to obtain the title compound (see Table 1).

Example 3

(E)-3-(2-(4-aminothieno[3,2-d]pyrimidine-7-yl)vinyl)-N-(3-(4-ethylpiperazine-1-yl)-5-(trifluoromethyl)phenyl)-4-methylbenzamide The procedure of Step 5 of Example 1 was repeated except for using (E)-3-(2-(4-aminothieno[3,2-d]pyrimidine-7-yl)vinyl)-4-methylbenzoic acid and 3-(4-ethylpiperazine-1-yl)-5-(trifluoromethyl)aniline to obtain the title compound (see Table 1).

The compound of Example 4 was prepared according to Reaction Scheme 3 below:

Reaction Scheme 3

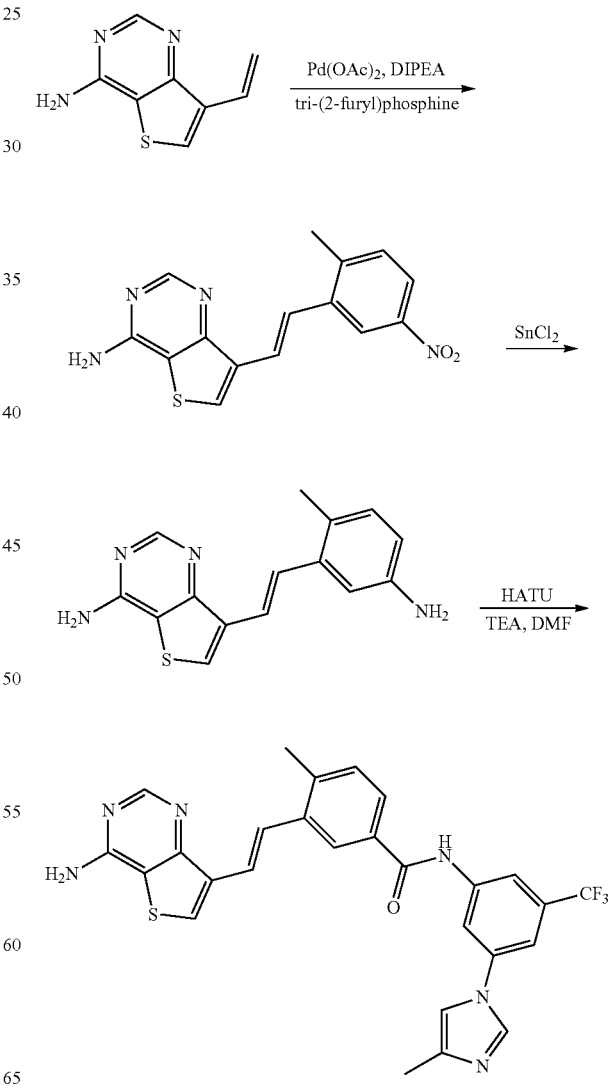

Example 4

(E)-N-(3-(2-(4-aminothieno[3,2-d]pyrimidine-7-yl)vinyl)-4-methylphenyl)-3-(4-methyl-1H-imidazole-1-yl)-5-(trifluoromethyl)benzamide Step 1: (E)-7-(2-methyl-5-nitrostyryl)thieno[3,2-d]pyrimidine-4-amine

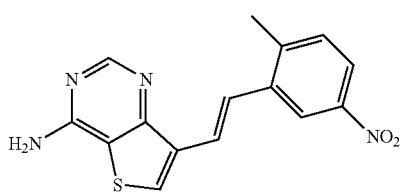 [SMILES: Cc1ccc([N+](=O)[O-])cc1/C=C/c1csc2c(N)ncnc12]

The procedure of Step 3 of Example 1 was repeated except for using 2-iodo-1-methyl-4-nitrobenzene (TCI Laboratory Chemicals, Cat. #10706, CAS [7745-92-8]) instead of ethyl-3-iodo-4-methyl benzoate to obtain the title compound.

$^1$H NMR (400 MHz, DMSO-$d_6$) δ 8.50 (s, 1H), 8.44 (d, 1H), 8.37 (s, 1H), 8.25 (d, 1H), 8.04 (d, 1H), 7.56 (d, 1H), 7.52 (d, 1H), 7.45 (s, 2H), 2.58 (s, 3H); MS m/z [M+1] 313.25.

Step 2: (E)-7-(5-amino-2-methylstyryl)thieno[3,2-d]pyrimidine-4-amine

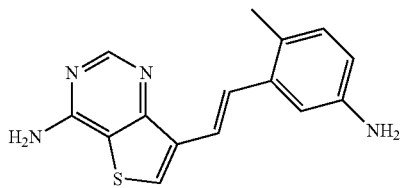 [SMILES: Cc1ccc(N)cc1/C=C/c1csc2c(N)ncnc12]

(E)-7-(2-methyl-5-nitrostyryl)thieno[3,2-d]pyrimidine-4-amine (0.3 g, 0.96 mmol) was dissolved in ethyl acetate (5 mL) and then SnCl$_2$.2H$_2$O (1 g, 4.81 mmol) and conc. HCl (0.5 mL) were added thereto, and the reaction mixture was stirred at room temperature for 18 hours. After the reaction was completed NH$_4$OH solution was added thereto to pH 5. Then, anhydrous Na$_2$CO$_3$ was added thereto to pH 7. The reaction mixture was filtered with Celite and washed with ethyl acetate several times. The filtrate was concentrated under reduced pressure to obtain the title compound (260 mg, 84% yield) without further purification.

$^1$H NMR (400 MHz, DMSO-$d_6$) δ 8.54 (s, 1H), 8.05 (s, 1H), 8.02 (s, 1H), 7.59 (d, 1H), 7.28 (d, 2H), 7.14 (d, 1H), 6.57 (d, 2H), 2.98 (m, 1H), 0.80 (m, 2H), 0.65 (m, 2H); MS m/z 309.32 [M+1].

Step 3: (E)-N-(3-(2-(4-aminothieno[3,2-d]pyrimidine-7-yl)vinyl)-4-methylphenyl)-3-(4-methyl-1H-imidazole-1-yl)-5-(trifluoromethyl)benzamide

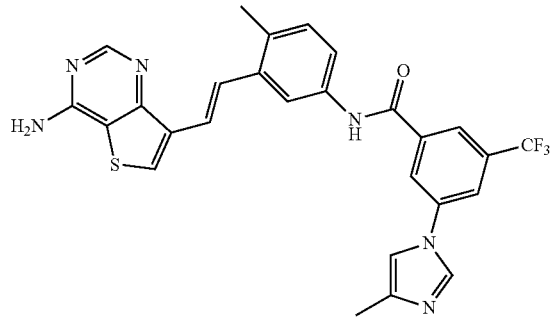 [SMILES: Cc1cn(-c2cc(C(=O)Nc3ccc(C)c(/C=C/c4csc5c(N)ncnc45)c3)cc(C(F)(F)F)c2)cn1]

(E)-7-(5-amino-2-methylstyryl)thieno[3,2-d]pyrimidine-4-amine (100 mg, 0.354 mmol) and 3-(4-methyl-1H-imidazole-1-yl)-5-(trifluoromethyl)benzoic acid (96 mg, 0.354 mmol) were dissolved in DMF (1.5 mL), HATU (404 mg, 1.063 mmol) and TEA (0.248 mL, 1.7728 mmol) were added thereto and stirred at room temperature for 18 hours. The reaction mixture was diluted with ethyl acetate and washed with brine. The organic layer was dried with MgSO$_4$, filtered and concentrated. The resulting mixture was purified by silica gel chromatography to obtain the title compound (142 mg, 75% yield).

MS m/z [M+1] 535.15.

Example 5

(E)-N-(3-(2-(4-aminothieno[3,2-d]pyrimidine-7-yl)vinyl)-4-methylphenyl)-4-(1-methylpiperidine-4-yloxy)-3-(trifluoromethyl)benzamide The procedure of Step 3 of Example 4 was repeated except for using 4-(1-methylpiperidine-4-yloxy)-3-(trifluoromethyl)benzoic acid instead of 3-(4-methyl-1H-imidazole-1-yl)-5-(trifluoromethyl)benzoic acid to obtain the title compound (see Table 1).

Example 6

(E)-N-(3-(2-(4-aminothieno[3,2-d]pyrimidine-7-yl)vinyl)-4-methylphenyl)-3-(trifluoromethyl)benzamide (E)-7-(5-amino-2-methylstyryl)thieno[3,2-d]pyrimidine-4-amine (100 mg, 0.354 mmol) was dissolved in anhydrous THF, TEA (0.1 mL, 0.709 mmol) and 3-(trifluoromethyl)benzoyl chloride (81 mg, 0.390 mmol) were added thereto at room temperature and stirred for 4 hours. The reaction mixture was diluted with ethyl acetate and washed with brine. The organic layer was dried with MgSO$_4$, filtered and concentrated. The resulting mixture was purified by silica gel chromatography to obtain the title compound (138 mg, 86% yield) (see Table 1).

Example 7

(E)-N-(3-(2-(4-aminothieno[3,2-d]pyrimidine-7-yl)vinyl)-4-methylphenyl)-4-((4-ethylpiperazin-1-yl)methyl)-3-(trifluoromethyl)benzamide The procedure of Step 3 of Example 4 was repeated except for using 4-((4-ethylpiperazine-1-yl)methyl)-3-(trifluoromethyl)benzoic acid instead of 3-(4-methyl-1H-imidazole-1-yl)-5-(trifluoromethyl)benzoic acid to obtain the title compound (see Table 1).

The compound of Preparation Example 2 was prepared according to Reaction Scheme 4 below:

Reaction Scheme 4

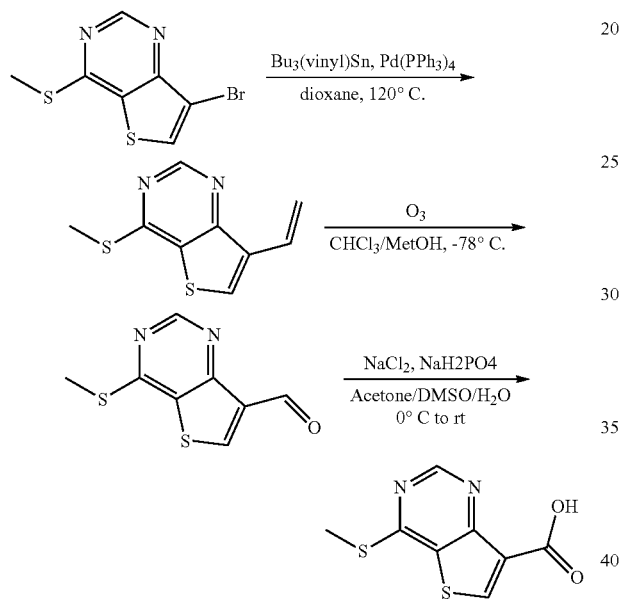

Preparation Example 2

4-(Methylthio)thieno[3,2-d]pyrimidine-7-carboxylic acid

Step 1:
4-(Methylthio)-7-vinylthieno[3,2-d]pyrimidine

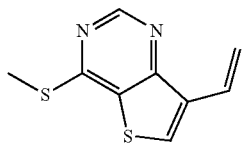

The procedure of Step 2 of Example 1 was repeated except for using 7-bromo-4-(methylthio)thieno[3,2-d]pyrimidine (500 mg, 1.92 mmol) obtained in Step 4 of Preparation Example 1 to obtain the title compound.

$^1$H NMR (400 MHz, DMSO-d$_6$) δ 9.05 (s, 1H), 8.40 (s, 1H), 7.02 (dd, 1H), 6.45 (d, 1H), 5.49 (d, 1H), 2.74 (s, 3H).

Step 2: 4-(Methylthio)thieno[3,2-d]pyrimidine-7-carbaldehyde

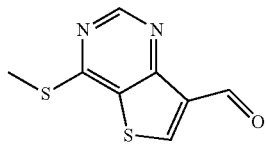

4-(Methylthio)-7-vinylthieno[3,2-d]pyrimidine (350 mg, 1.68 mmol) was dissolved in CHCl$_3$/MeOH (2 mL/2 mL) and treated with ozone at 78° C. for 30 minutes. When the starting material was disappeared, the reaction mixture was treated with N$_2$ gas at the same temperature for 5 minutes, heated to room temperature, and dimethylsulfide (0.37 mL, 5.04 mmol) was added thereto. The reaction mixture was concentrated to obtain a yellow solid. The solid was filtered, washed with diethyl ether and dried with N$_2$ gas to obtain the title compound without further purification.

$^1$H NMR (400 MHz, DMSO-d$_6$) δ 10.30 (s, 1H), 9.21 (s, 1H), 9.13 (s, 1H), 2.77 (s, 3H).

Step 3:
4-(Methylthio)thieno[3,2-d]pyrimidine-7-carboxylic acid

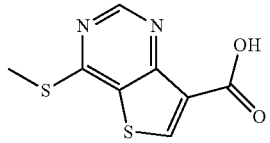

NaH$_2$PO$_4$.2H$_2$O (513 mg, 3.29 mmol) was dissolved in water (2 mL) and then 4-(methylthio)thieno[3,2-d]pyrimidine-7-carbaldehyde (300 mg, 1.68 mmol) dissolved in acetone (3 mL) and DMSO (3 mL) was added thereto at 0° C. NaClO$_2$ (194 mg, 2.15 mmol) dissolved in water (2 mL) was added at the same temperature to the reaction mixture, which was stirred for 2 hours. After the reaction was completed water (10 mL) was further added to the reaction mixture, which was stirred for 2 hours and filtered to obtain a solid. The solid was washed with water several times and dried with N$_2$ gas to obtain the title compound as a white solid.

$^1$H NMR (400 MHz, DMSO-d$_6$) δ 8.98 (s, 1H), 8.49 (s, 1H), 2.72 (s, 1H).

The compound of Example 8 was prepared according to Reaction Scheme 5 below:

Reaction Scheme 5

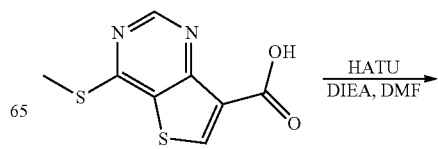

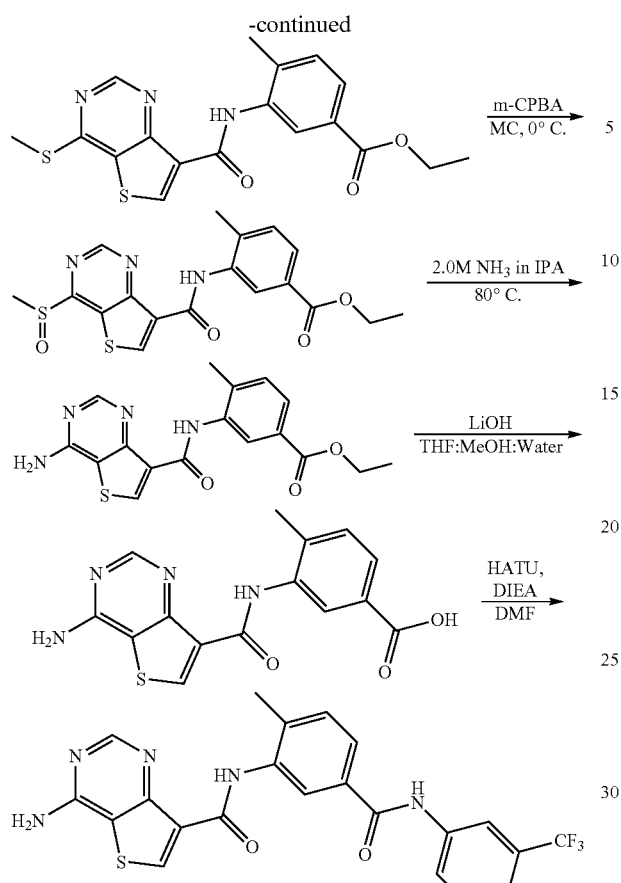

Example 8

4-Amino-N-(2-methyl-5-(3-(trifluoromethyl)phenyl-carbamoyl)phenyl)thieno[3,2-d]pyrimidine-7-carboxamide

Step 1: Ethyl 4-methyl-3-(4-(methylthio)thieno[3,2-d]pyrimidine-7-carboxamido)benzoate

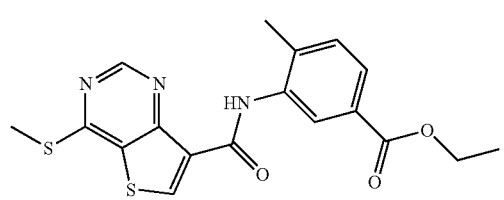 [SMILES: CCOC(=O)c1ccc(C)c(NC(=O)c2csc3c(SC)ncnc23)c1]

4-(Methylthio)thieno[3,2-d]pyrimidine-7-carboxylic acid (2 g, 10.2 mmol) obtained in Step 3 of Preparation Example 2 was dissolved in DMF (40 mL), methyl 3-amino-4-methyl benzoate (1.2 g, 7.3 mmol), HATU (8.3 g, 22 mmol) and DIPEA (6.4 mL, 36.6 mmol) were added thereto and stirred at 45° C. for 18 hours. The reaction mixture was diluted with ethyl acetate and washed with an aqueous sodium bicarbonate solution and brine, sequentially. The organic layer was dried with MgSO₄, filtered and concentrated. The resulting mixture was purified by silica gel chromatography to obtain the title compound (2.5 g).

MS m/z [M+1] 388.09.

Step 2: Ethyl 4-methyl-3-(4-(methylsulfinyl)thieno[3,2-d]pyrimidine-7-carboxamido)benzoate

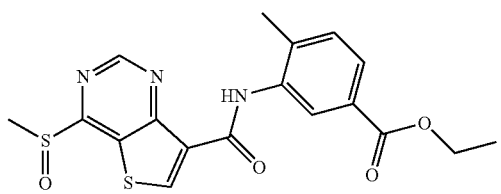 [SMILES: CCOC(=O)c1ccc(C)c(NC(=O)c2csc3c(S(C)=O)ncnc23)c1]

Ethyl 4-methyl-3-(4-(methylthio)thieno[3,2-d]pyrimidine-7-carboxamido)benzoate (500 mg, 1.29 mmol) was dissolved in DCM (6 mL) and m-CPBA (290 mg, 1.67 mmol) was added thereto at 0° C. The reaction mixture was stirred at room temperature for 2 hours, diluted with DCM (30 mL) and washed with sat. NaHCO₃ solution. The organic layer was dried with anhydrous MgSO₄, filtered with Celite and concentrated to obtain the title compound without further purification.

MS m/z [M+1] 404.07.

Step 3: Ethyl 3-(4-aminothieno[3,2-d]pyrimidine-7-carboxamido)-4-methyl benzoate

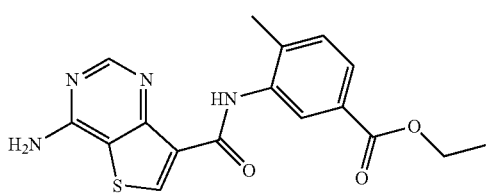 [SMILES: CCOC(=O)c1ccc(C)c(NC(=O)c2csc3c(N)ncnc23)c1]

The procedure of Step 1 of Example 1 was repeated except for using the compound obtained in Step 2 of Example 8 to obtain the title compound.

¹H NMR (400 MHz, DMSO-d₆) δ 11.89 (s, 1H), 8.98 (s, 1H), 8.96 (s, 1H), 8.59 (s, 1H), 7.95 (s, 2H), 7.66 (d, 1H), 7.44 (d, 1H), 4.32 (q, 2H), 2.54 (s, 3H), 1.33 (t, 3H); MS m/z [M+1] 356.9.

Step 4: 3-(4-Aminothieno[3,2-d]pyrimidine-7-carboxamido)-4-methylbenzoic acid

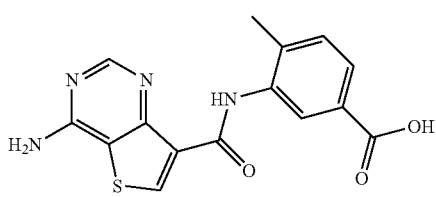 [SMILES: Cc1ccc(C(=O)O)cc1NC(=O)c1csc2c(N)ncnc12]

The procedure of Step 4 of Example 1 was repeated except for using the compound obtained in Step 3 of Example 8 to obtain the title compound.

MS m/z [M+1] 329.1.

Step 5: 4-Amino-N-(2-methyl-5-(3-(trifluoromethyl)phenylcarbamoyl)phenyl)thieno[3,2-d]pyrimidine-7-carboxamide

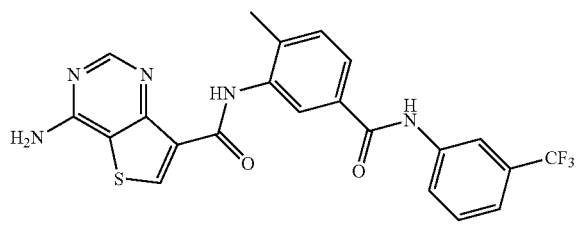 [SMILES: Cc1ccc(C(=O)Nc2cccc(C(F)(F)F)c2)cc1NC(=O)c1csc2c(N)ncnc12]

The procedure of Step 5 of Example 1 was repeated except for using the compound obtained in Step 4 of Example 8 to obtain the title compound.
$^1$H NMR (300 MHz, DMSO-$d_6$) δ 11.80 (s, 1H), 10.47 (s, 1H), 8.89 (s, 1H), 8.80 (d, 1H, J=1.6 Hz), 8.52 (s, 1H), 8.20-8.17 (m, 1H), 8.00-7.97 (m, 2H), 7.95-8.95 (bs, 2H), 7.63-7.60 (m, 1H), 7.52 (t, 1H, J=8.0 Hz), 7.40-7.36 (m, 2H), 2.51 (s, 3H).

Example 9

4-Amino-N-(5-(3-methoxyphenylcarbamoyl)-2-methylphenyl)thieno[3,2-d]pyrimidine-7-carboxamide The procedure of Step 5 of Example 1 was repeated except for using 3-(4-aminothieno[3,2-d]pyrimidine-7-carboxamido)-4-methylbenzoic acid obtained in Step 4 of Example 8 and 3-methoxyaniline to obtain the title compound (see Table 1).

Example 10

4-Amino-N-(2-methyl-5-(3-(4-methyl-1H-imidazole-1-yl)-5-(trifluoromethyl)phenylcarbamoyl)phenyl)thieno[3,2-d]pyrimidine-7-carboxamide The procedure of Step 5 of Example 1 was repeated except for using 3-(4-aminothieno[3,2-d]pyrimidine-7-carboxamido)-4-methylbenzoic acid obtained in Step 4 of Example 8 and 3-(4-methyl-1H-imidazole-1-yl)-5-(trifluoromethyl)aniline to obtain the title compound (see Table 1).

Example 11

4-Amino-N-(5-(4-((4-ethylpiperazin-1-yl)methyl)-3-(trifluoromethyl)phenylcarbamoyl)-2-methylphenyl)thieno[3,2-d]pyrimidine-7-carboxamide The procedure of Step 5 of Example 1 was repeated except for using 3-(4-aminothieno[3,2-d]pyrimidine-7-carboxamido)-4-methylbenzoic acid obtained in Step 4 of Example 8 and 4-((4-ethylpiperazin-1-yl)methyl)-3-(trifluoromethyl)benzenamine to obtain the title compound (see Table 1).

Example 12

4-Amino-N-(5-(3,5-dimethoxyphenylcarbamoyl)-2-methylphenyl)thieno[3,2-d]pyrimidine-7-carboxamide The procedure of Step 5 of Example 1 was repeated except for using 3-(4-aminothieno[3,2-d]pyrimidine-7-carboxamido)-4-methylbenzoic acid obtained in Step 4 of Example 8 and 3,5-dimethoxyaniline to obtain the title compound (see Table 1).

The compound of Example 13 was prepared according to Reaction Scheme 6 below:

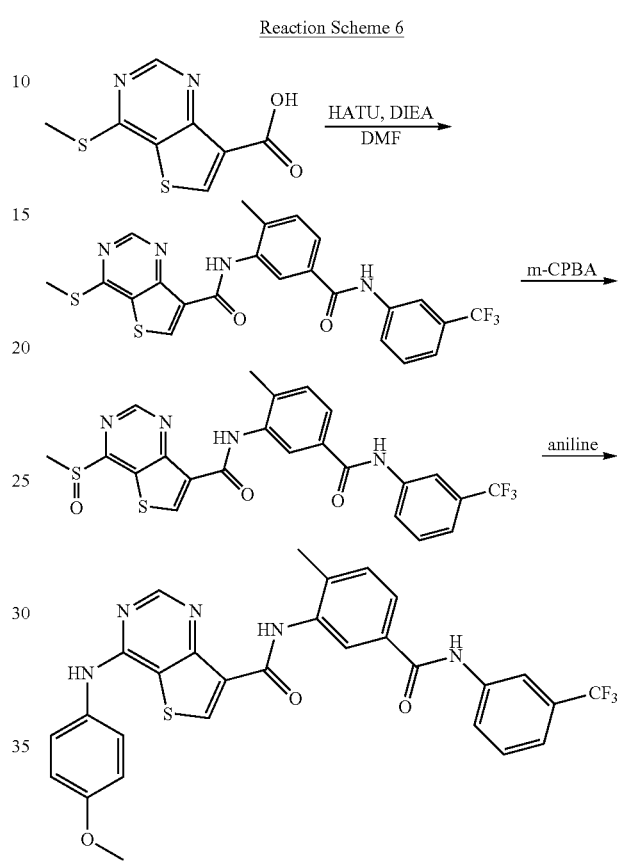

Example 13

4-(4-Methoxyphenylamino)-N-(2-methyl-5-(3-(trifluoromethyl)phenylcarbamoyl)phenyl)thieno[3,2-d]pyrimidine-7-carboxamide Step 1: N-(2-methyl-5-(3-(trifluoromethyl)phenylcarbamoyl)phenyl)-4-(methylthio)thieno[3,2-d]pyrimidine-7-carboxamide

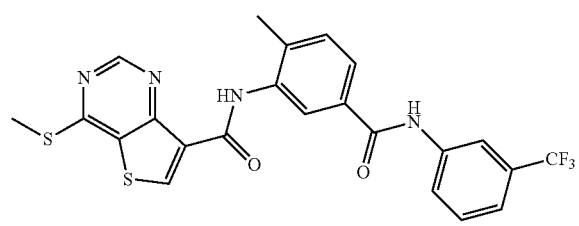 [SMILES: CSc1ncnc2c(C(=O)Nc3cc(C(=O)Nc4cccc(C(F)(F)F)c4)ccc3C)csc12]

The procedure of Step 1 of Example 8 was repeated except for using the compound obtained in Preparation Example 2 and 3-amino-4-methyl-N-(3-(trifluoromethyl)phenyl)benzamide to obtain the title compound.
MS m/z [M+1] 503.09.

Step 2: N-(2-methyl-5-(3-(trifluoromethyl)phenyl-carbamoyl)phenyl)-4-(methylsulfinyl)thieno[3,2-d]pyrimidine-7-carboxamide

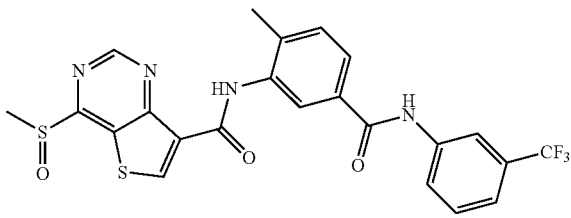 [SMILES: Cc1ccc(C(=O)Nc2cccc(C(F)(F)F)c2)cc1NC(=O)c1csc2c(S(C)=O)ncnc12]

The procedure of Step 2 of Example 8 was repeated except for using the compound obtained in Step 1 of Example 13 to obtain the title compound.
MS m/z [M+1] 519.08.

Step 3: 4-(4-Methoxyphenylamino)-N-(2-methyl-5-(3-(trifluoromethyl)phenylcarbamoyl)phenyl)thieno[3,2-d]pyrimidine-7-carboxamide

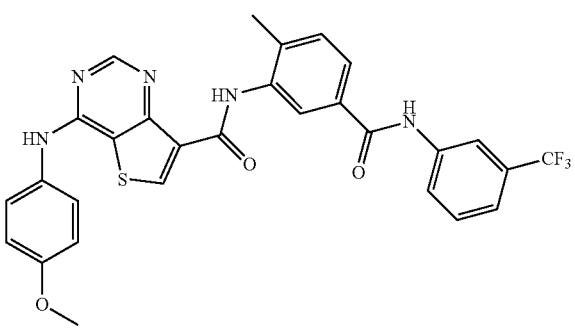 [SMILES: COc1ccc(Nc2ncnc3c(C(=O)Nc4cc(C(=O)Nc5cccc(C(F)(F)F)c5)ccc4C)csc23)cc1]

N-(2-methyl-5-(3-(trifluoromethyl)phenylcarbamoyl)phenyl)-4-(methylsulfinyl)thieno[3,2-d]pyrimidine-7-carboxamide (30 mg, 0.060 mmol) was dissolved in dioxane (1 mL) and DIPEA (20 µL, 0.119 mmol) and 4-methoxybenzeneamine (37 mg, 0.298 mmol) were added thereto. The reaction mixture was stirred at 120° C. for 18 hours, cooled to room temperature, diluted with ethyl acetate and washed with a brine. The organic layer was dried with MgSO$_4$, filtered and concentrated under reduced pressure. The resulting mixture was purified by silica gel chromatography to obtain the title compound (28 mg, 81% yield).
$^1$H NMR (400 MHz, DMSO-d$_6$) δ 11.85 (s, 1H), 10.56 (s, 1H), 10.06 (s, 1H), 9.00 (s, 1H), 8.87 (s, 1H), 8.73 (s, 1H), 8.26 (s, 1H), 8.08 (d, 1H), 7.72 (d, 1H), 7.63-7.57 (m, 3H), 7.47 (d, 2H), 7.01 (d, 2H), 3.79 (s, 3H), 2.54 (s, 3H); MS m/z [M+1] 578.07.

Example 14

N-(2-methyl-5-(3-(trifluoromethyl)phenylcarbamoyl)phenyl)-4-(3,4,5-trimethoxyphenylamino)thieno[3,2-d]pyrimidine-7-carboxamide The procedure of Step 3 of Example 13 was repeated except for using the compound obtained in Step 2 of Example 13 and 3,4,5-trimethoxyaniline to obtain the title compound (see Table 1).

Example 15

N-(2-methyl-5-(3-(trifluoromethyl)phenylcarbamoyl)phenyl)-4-(6-methylpyridine-3-ylamino)thieno[3,2-d]pyrimidine-7-carboxamide The procedure of Step 3 of Example 13 was repeated except for using the compound obtained in Step 2 of Example 13 and 6-methylpyridine-3-amine to obtain the title compound (see Table 1).

Example 16

4-(4-(4-Ethylpiperazin-1-yl)phenylamino)-N-(2-methyl-5-(3-(trifluoromethyl)phenylcarbamoyl)phenyl)thieno[3,2-d]pyrimidine-7-carboxamide The procedure of Step 3 of Example 13 was repeated except for using the compound obtained in Step 2 of Example 13 and 4-(4-ethylpiperazine-1-yl)aniline to obtain the title compound (see Table 1).

Example 17

4-(Isopropylamino)-N-(2-methyl-5-(3-(trifluoromethyl)phenylcarbamoyl)phenyl)thieno[3,2-d]pyrimidine-7-carboxamide The procedure of Step 3 of Example 13 was repeated except for using the compound obtained in Step 2 of Example 13 and isopropylamine to obtain the title compound (see Table 1).

Example 18

N-(2-methyl-5-(3-(trifluoromethyl)phenylcarbamoyl)phenyl)-4-(methylamino)thieno[3,2-d]pyrimidine-7-carboxamide The procedure of Step 3 of Example 13 was repeated except for using the compound obtained in Step 2 of Example 13 and methylamine hydrochloride to obtain the title compound (see Table 1).

Example 19

4-(2-Hydroxyethylamino)-N-(2-methyl-5-(3-(trifluoromethyl)phenylcarbamoyl)phenyl)thieno[3,2-d]pyrimidine-7-carboxamide The procedure of Step 3 of Example 13 was repeated except for using the compound obtained in Step 2 of Example 13 and 2-aminoethanol to obtain the title compound (see Table 1).

Example 20

N-(2-Methyl-5-(3-(trifluoromethyl)phenylcarbamoyl)phenyl)-4-(2-morpholinoethylamino)thieno[3,2-d]pyrimidine-7-carboxamide The procedure of Step 3 of Example 13 was repeated except for using the compound obtained in Step 2 of Example 13 and 2-morpholino ethaneamine to obtain the title compound (see Table 1).

The compound of Preparation Example 3 was prepared according to Reaction Scheme 7 below:

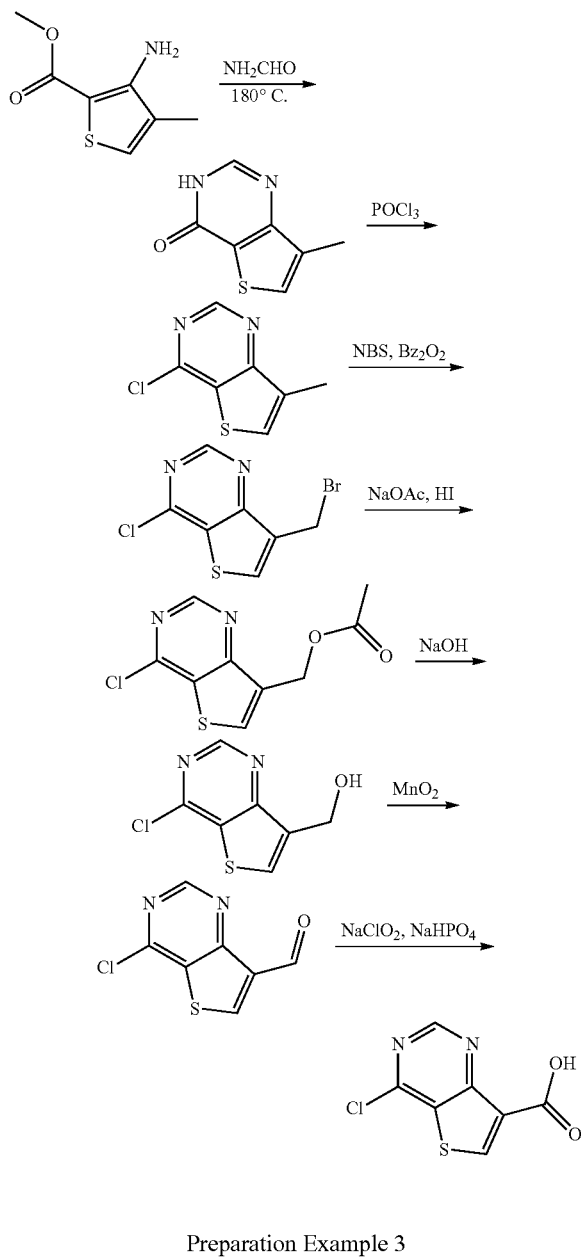

Preparation Example 3

4-Chlorothieno[3,2-d]pyrimidine-7-carboxylic acid

Step 1: 7-Methylthieno[3,2-d]pyrimidine-4(3H)-one

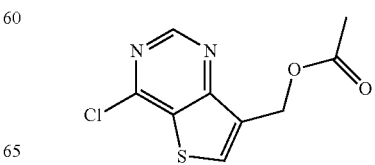

Methyl 3-amino-4-methylthiophene-2-carboxylate (3.0 g) was added to formamide (5 mL), and the mixture was stirred at 200° C. for 3 hours. After cooling to room temperature water (50 mL) was added thereto and then stirred for 15 hours at room temperature to obtain a solid. The solid was filtered, washed with water and dried with $N_2$ gas to obtain the title compound as a white solid without further purification.

$^1$H NMR (400 MHz, DMSO-$d_6$) δ 12.50 (br, 1H), 8.16 (s, 1H), 7.86 (s, 1H), 2.30 (s, 3H).

Step 2: 4-Chloro-7-methylthieno[3,2-d]pyrimidine

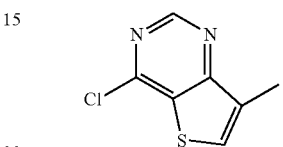

7-Methylthieno[3,2-d]pyrimidine-4(3H)-one (1.5 g) was added to POCl$_3$ (10 mL), and the mixture was stirred at 110° C. for 2 hours. The reaction mixture was cooled to room temperature, concentrated and diluted with DCM, and sat. NaHCO$_3$ solution was added thereto. The aqueous layer was extracted with DCM to combine organic layers. The organic layer was dried with MgSO$_4$ and filtered to obtain the title compound as a white solid.

$^1$H NMR (400 MHz, DMSO-$d_6$) δ 9.06 (s, 1H), 8.24 (s, 1H), 2.43 (s, 3H).

Step 3: 7-(Bromomethyl)-4-chlorothieno[3,2-d]pyrimidine

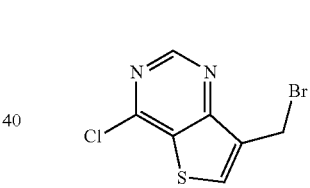

4-Chloro-7-methylthieno[3,2-d]pyrimidine (6.62 g, 33.0 mmol) and NBS (5.87 g, 33.0 mmol) were dissolved in CCl$_4$ (100 mL) and benzoylperoxide (1.0 g, 80% purity) was added thereto. The reaction mixture was stirred at 100° C. for an hour, cooled to room temperature, filtered with Celite and concentrated to obtain the title compound having a yellow color without further purification.

$^1$H NMR (400 MHz, DMSO-$d_6$) δ 9.15 (s, 1H), 8.75 (s, 1H), 4.93 (s, 2H).

Step 4: (4-Chlorothieno[3,2-d]pyrimidine-7-yl)methyl acetate 7-(Bromomethyl)-4-chlorothieno[3,2-d]pyrimidine (9.17 g, 33.0 mmol) was dissolved in DMF (54 mL) and then sodium acetate (27 g, 330 mmol) and potassium iodide (10.96 g, 66.0 mmol) were added thereto. The reaction mixture was stirred at 35° C. for 4 hours, diluted with ethyl acetate and washed with sat. sodium thiosulfate solution 5 times. The reaction mixture was dried with MgSO₄, filtered, concentrated and purified by silica gel chromatography to obtain to obtain the title compound as a white solid.

$^1$H NMR (400 MHz, DMSO-d$_6$) δ 9.06 (s, 1H), 8.60 (s, 1H), 5.38 (s, 2H), 2.06 (s, 3H).

Step 5:
(4-Chlorothieno[3,2-d]pyrimidine-7-yl)methanol

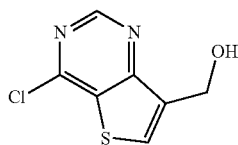 [SMILES: OCc1csc2c(Cl)ncnc12]

(4-Chlorothieno[3,2-d]pyrimidine-7-yl)methyl acetate (3.12 g, 12.06 mmol) was dissolved in THF (240 mL) and then 1N NaOH solution (100 mL) was added thereto at room temperature. The reaction mixture was stirred for 30 minutes, diluted with ethyl acetate, and the aqueous layer was extracted with ethyl acetate. The organic layer was dried with MgSO₄, filtered and concentrated to obtain the title compound as a white solid without further purification.

$^1$H NMR (400 MHz, DMSO-d$_6$) δ 9.09 (s, 1H), 8.33 (s, 1H), 5.47 (t, 1H), 4.84 (d, 2H).

Step 6:
4-Chlorothieno[3,2-d]pyrimidine-7-carbaldehyde

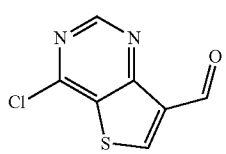

(4-Chlorothieno[3,2-d]pyrimidine-7-yl)methanol (215 mg, 0.99 mmol) and MnO₂ (863 mg, 9.9 mmol, 10 eq) were dissolved in chloroform (10 mL) and stirred at 70° C. for 2 hours. The reaction mixture was cooled to room temperature, filtered with Celite and concentrated to obtain the title compound as a white solid without further purification.

$^1$H NMR (400 MHz, DMSO-d$_6$) δ 10.30 (s, 1H), 9.40 (s, 1H), 9.20 (s, 1H).

Step 7:
4-Chlorothieno[3,2-d]pyrimidine-7-carboxylic acid

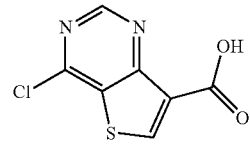 [SMILES: O=C(O)c1csc2c(Cl)ncnc12]

NaH₂PO₄·2H₂O (170 mg, 1.07 mmol) was dissolved in water (0.6 mL) and 4-chlorothieno[3,2-d]pyrimidine-7-carbaldehyde (100 mg, 0.47 mmol) dissolved in DMSO (4.8 mL) was added thereto at 10° C. The reaction mixture was cooled to 0° C. and NaClO₂ (170 mg, 1.88 mmol) dissolved in water (0.6 mL) was added thereto at 0° C. The reaction mixture was heated to room temperature, stirred for 2 hours, and water (10 mL) was added thereto. The reaction mixture was stirred for 2 hours and then filtered. The filtrate was concentrated to obtain the title compound as a white solid.

$^1$H NMR (400 MHz, DMSO-d$_6$) δ 9.07 (s, 1H), 8.87 (s, 1H).

The compound of Example 21 was prepared according to Reaction Scheme 8 below:

Reaction Scheme 8

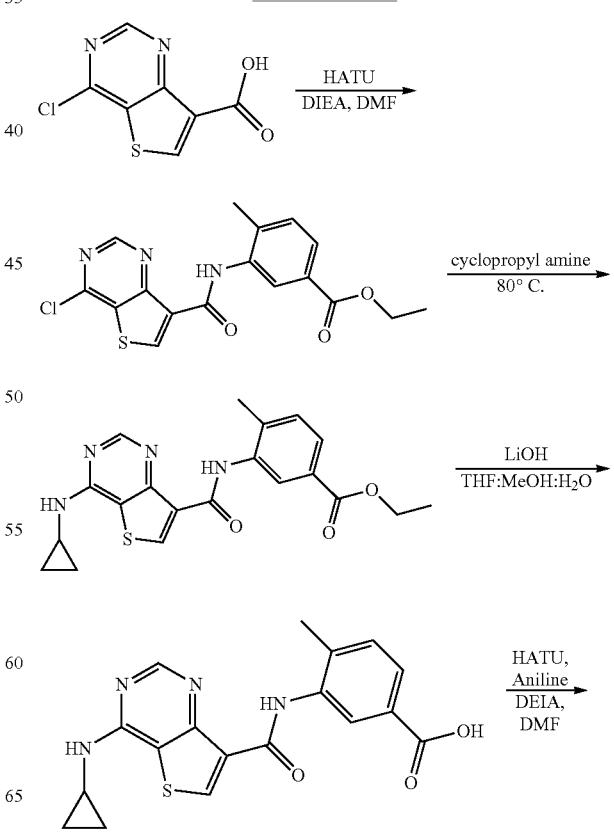

Example 21

4-(Cyclopropylamino)-N-(2-methyl-5-(3-(trifluoromethyl)phenylcarbamoyl)phenyl)thieno[3,2-d]pyrimidine-7-carboxamide

Step 1: Ethyl 3-(4-chlorothieno[3,2-d]pyrimidine-7-carboxamido)-4-methyl benzoate

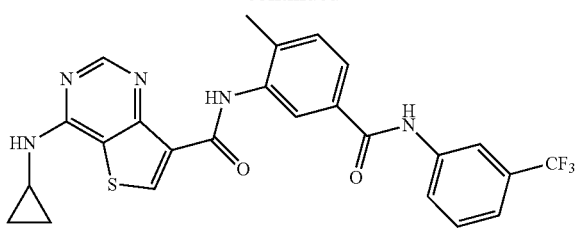

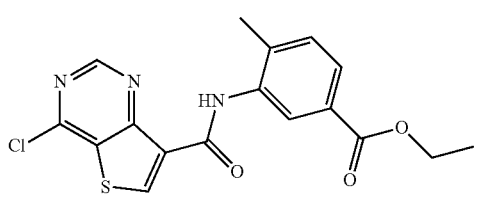 [SMILES: CCOC(=O)c1ccc(C)c(NC(=O)c2csc3c(Cl)ncnc23)c1]

The procedure of Step 1 of Example 8 was repeated except for using the compound obtained in Preparation Example 3 as a starting material to obtain the title compound.

MS m/z [M+1] 376.05.

Step 2: Ethyl 3-(4-(cyclopropylamino)thieno[3,2-d]pyrimidine-7-carboxamido)-4-methyl benzoate

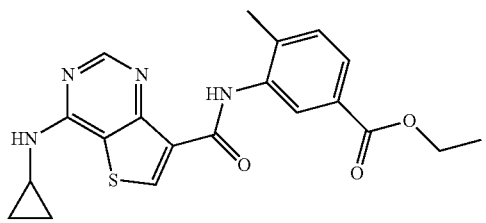 [SMILES: CCOC(=O)c1ccc(C)c(NC(=O)c2csc3c(NC4CC4)ncnc23)c1]

The procedure of Step 3 of Example 13 was repeated except for using the compound obtained in Step 1 of Example 21 as a starting material to obtain the title compound.

¹H NMR (400 MHz, DMSOd₆) δ 11.91 (s, 1H), 8.97 (s, 1H), 8.66 (s, 1H), 8.51 (s, 1H), 7.66 (d, 1H), 7.44 (d, 1H), 4.32 (q, 2H), 3.08-3.03 (m, 1H), 2.54 (s, 3H), 1.33 (t, 3H), 0.86 (br s, 2H), 0.70 (br s 2H); MS m/z [M+1] 397.93.

Step 3: 3-(4-(Cyclopropylamino)thieno[3,2-d]pyrimidine-7-carboxamido)-4-methylbenzoic acid

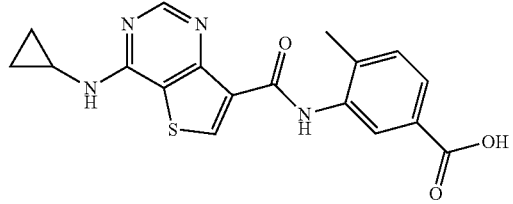 [SMILES: Cc1ccc(C(=O)O)cc1NC(=O)c1csc2c(NC3CC3)ncnc12]

The procedure of Step 4 of Example 1 was repeated except for using the compound obtained in Step 2 of Example 21 as a starting material to obtain the title compound.

¹H NMR (400 MHz, DMSO-d₆) δ 13.02-12.80 (m, 1H), 11.90 (s, 1H), 8.96 (s, 1H), 8.93 (s, 1H), 8.66 (s, 1H), 8.53 (s, 1H), 7.64 (dd, 1H), 7.40 (d, 1H), 3.07-3.03 (m, 1H), 2.54 (s, 3H), 0.86 (br s, 2H), 0.70 (br s, 2H).

Step 4: 4-(Cyclopropylamino)-N-(2-methyl-5-(3-(trifluoromethyl)phenylcarbamoyl)phenyl)thieno[3,2-d]pyrimidine-7-carboxamide

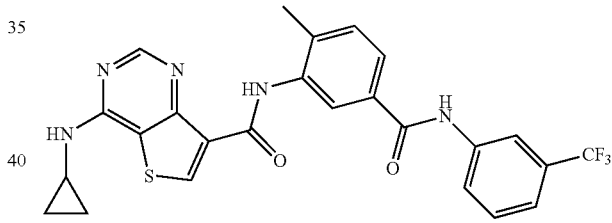

The procedure of Step 5 of Example 1 was repeated except for using the compound obtained in Step 3 of Example 21 as a starting material to obtain the title compound.

MS m/z [M+1] 512.06

The compound of Preparation Example 4 was prepared according to Reaction Scheme 9 below:

Reaction Scheme 9

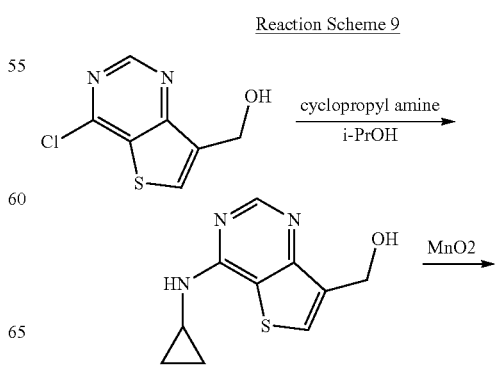

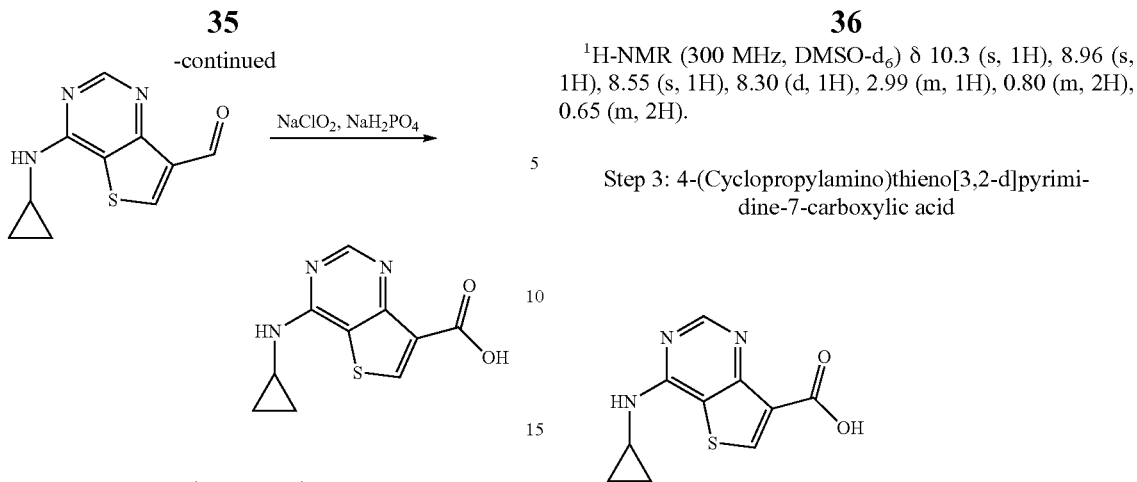

NaClO₂, NaH₂PO₄

¹H-NMR (300 MHz, DMSO-d₆) δ 10.3 (s, 1H), 8.96 (s, 1H), 8.55 (s, 1H), 8.30 (d, 1H), 2.99 (m, 1H), 0.80 (m, 2H), 0.65 (m, 2H).

Step 3: 4-(Cyclopropylamino)thieno[3,2-d]pyrimidine-7-carboxylic acid

Preparation Example 4

4-(Cyclopropylamino)thieno[3,2-d]pyrimidine-7-carboxylic acid

Step 1: (4-(Cyclopropylamino)thieno[3,2-d]pyridine-7-yl)methanol

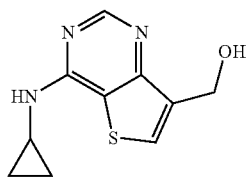 [SMILES: OCc1csc2c(NC3CC3)ncnc12]

Isopropanol (590 mL) and cyclopropylamine (102 mL, 1.5 mol) were added to the compound (59 g, 29.3 mmol) obtained in Step 5 of Preparation Example 3, and stirred for 12 hours with reflux. The reaction mixture was cooled to room temperature, concentrated, diluted with ethyl acetate (1 L), washed with a sat. aqueous sodium hydrogen carbonate solution (800 mL×3) and then concentrated. The resulting mixture was crystallized using a methanol/diethyl ether/hexane mixture (1:10:10, v/v/v) to obtain the title compound (46.5 g).

¹H-NMR (300 MHz, DMSO-d₆) δ 8.42 (s, 1H), 7.93 (d, 1H), 7.84 (s, 1H), 5.23-5.19 (t, 1H), 4.70 (d, 2H), 2.96 (m, 1H), 0.78 (m, 2H), 0.62 (m, 2H).

Step 2: 4-(Cyclopropylamino)thieno[3,2-d]pyrimidine-7-carbaldehyde

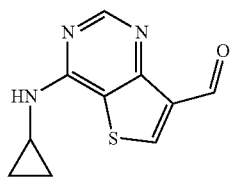 [SMILES: O=Cc1csc2c(NC3CC3)ncnc12]

The compound (46.5 g, 210 mmol) obtained in Step 1 of Preparation Example 4 was dissolved in chloroform (2.0 L), manganese dioxide (183 g, 2.1 mol) was added thereto and stirred for 12 hours with reflux. The reaction mixture was cooled to room temperature, manganese dioxide was filtered with Celite, and the filtrate was concentrated and dried to obtain the title compound (40.9 g) without further purification.

NaH₂PO₄·2H₂O (67 g, 429 mmol) was dissolved in water (220 mL), the compound (41 g, 187 mmol) obtained in Step 2 of Preparation Example 4 dissolved in a acetone/dimethyl sulfoxide mixture (1:1, v/v) (640 mL) was added thereto slowly, cooled to 0° C. and stirred for 30 minutes. NaClO₂ (25.3 g, 280 mmol) dissolved in water (220 mL) was added to the reaction mixture slowly at 0° C. and stirred at room temperature for 5 hours. Water (400 mL) was added to the reaction mixture to remove gel therein, and the resulting solid was filtered and washed sequentially with water, ethyl acetate and dimethyl ether. Ethyl acetate (400 mL) was added thereto and stirred to remove the remaining dimethyl sulfoxide solvent. The solid was filtered and washed with diethyl ether to obtain the title compound (32 g).

¹H-NMR (300 MHz, DMSO-d₆) δ 8.97 (s, 1H), 8.75 (br. s, 1H), 8.59 (s, 1H), 3.05 (m, 1H), 0.86 (m, 2H), 0.69 (m, 2H).

The compound of Preparation Example 5 was prepared according to Reaction Scheme 10 below:

Reaction Scheme 10

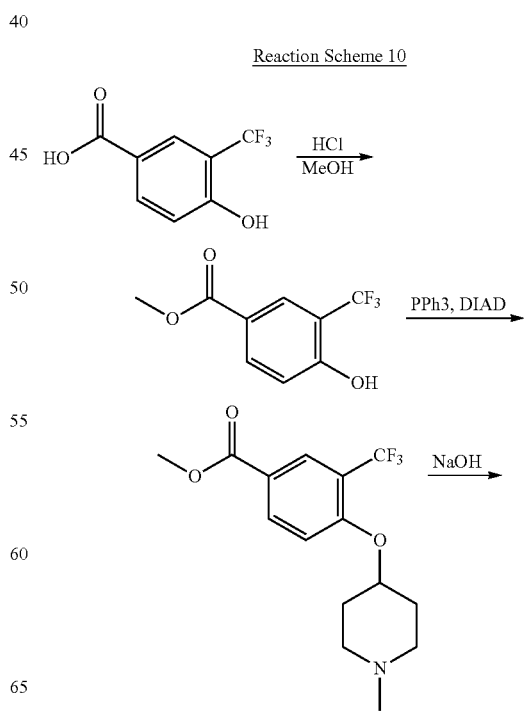

-continued

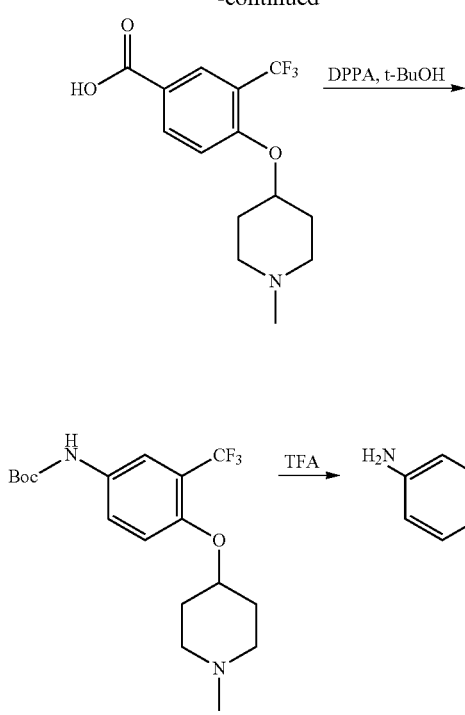

Preparation Example 5

4-(1-Methylpiperidine-4-yloxy)-3-(trifluoromethyl)benzeneamine

Step 1: Methyl 4-hydroxy-3-(trifluoromethyl)benzoate

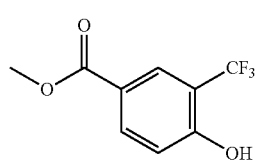

4-Hydroxy-3-(trifluoromethyl)benzoic acid (2 g, 9.7 mmol) was dissolved in methanol (40 mL) and 12N HCl (10 drops) was added thereto. The reaction mixture was stirred at 90° C. for 48 hours, cooled to room temperature and concentrated, and then ethyl acetate (100 mL) was added thereto. The reaction mixture was washed with sat. NaHCO$_3$ Solution, and the organic layer was dried with Na$_2$SO$_4$, filtered and concentrated to obtain the title compound (2.07 g, 91%) without further purification.

$^1$H NMR (300 MHz, DMSO-d$_6$) δ 11.60 (s, 1H), 8.02 (m, 2H), 7.10 (d, 1H), 4.26 (q, 2H), 1.28 (t, 3H).

Step 2: Methyl 4-(1-methylpiperidine-4-yloxy)-3-(trifluoromethyl)benzoate

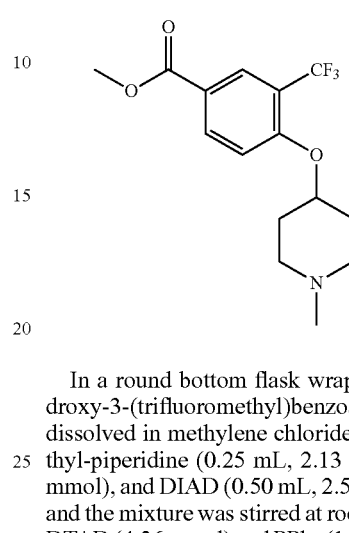

In a round bottom flask wrapped with foil, methyl 4-hydroxy-3-(trifluoromethyl)benzoate (500 mg, 2.13 mmol) was dissolved in methylene chloride (10 mL). 4-Hydroxy-1-methyl-piperidine (0.25 mL, 2.13 mmol), PPh$_3$ (670 mg, 2.56 mmol), and DIAD (0.50 mL, 2.56 mmol) were added thereto, and the mixture was stirred at room temperature for 23 hours. DTAD (4.26 mmol) and PPh$_3$ (1.12 g, 4.26 mmol) were added at 0° C. to the reaction mixture, which was stirred at room temperature for 24 hours. The resulting mixture was concentrated and then purified by silica gel chromatography (Hex/EA=1/1→DCM/MeOH=10/1) to obtain the title compound (512 mg, 76%).

$^1$H NMR (300 MHz, DMSO-d$_6$) δ 8.14 (dd, 1H), 8.08 (d, 1H), 7.43 (d, 1H), 4.77 (m, 1H), 4.30 (q, 2H), 2.35 (m, 2H), 2.24 (m, 2H), 2.19 (s, 3H), 1.93 (m, 2H), 1.73 (m, 2H), 1.27 (t, 3H).

Step 3: 4-(1-Methylpiperidine-4-yloxy)-3-(trifluoromethyl)benzoic acid

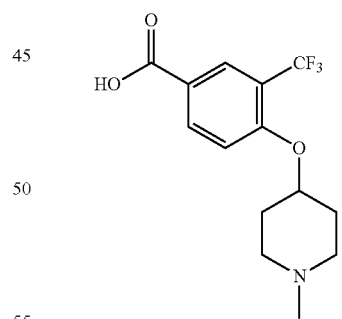

Methyl 4-(1-methylpiperidine-4-yloxy)-3-(trifluoromethyl)benzoate (512 mg, 1.61 mmol) was dissolved in a mixture of THF (1.5 mL), MeOH (1.5 mL) and H$_2$O (1.5 mL), and then NaOH (193 mg, 4.84 mmol) was added thereto. The reaction mixture was stirred at 90° C. for 22 hours and cooled to room temperature, and 1N HCl was added dropwise thereto to pH 4. The reaction mixture was concentrated, and a mixed solvent (DCM/MeOH=5/1) was added thereto. The remaining solid was filtered, and the filtrate was concentrated to obtain the title compound (391 mg, 80%) without further purification.

¹H NMR (300 MHz, DMSO-d₆) δ 8.16 (dd, 1H), 8.11 (d, 1H), 7.46 (d, 1H), 4.93 (m, 1H), 3.03 (m, 4H), 2.63 (s, 3H), 2.15 (m, 2H), 1.95 (m, 2H).

Step 4: t-Butyl 4-(1-methylpiperidine-4-yloxy)-3-(trifluoromethyl)phenylcarbamate

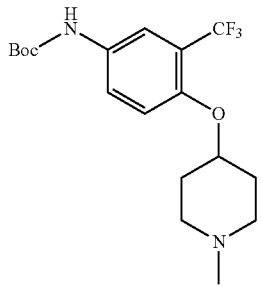 [SMILES: CN1CCC(Oc2ccc(NC(=O)OC(C)(C)C)cc2C(F)(F)F)CC1]

4-(1-Methylpiperidine-4-yloxy)-3-(trifluoromethyl)benzoic acid (200 mg, 0.659 mmol) was dissolved in t-BuOH (6 mL) and then DPPA (0.21 mL, 0.989 mmol) and TEA (0.14 mL, 0.989 mmol) was added thereto. The reaction mixture was stirred at 90° C. for 23 hours, cooled to room temperature, and sat. NaHCO₃ solution was added thereto. The aqueous layer was washed with ethyl acetate, and the combined organic layer was dried with Na₂SO₄, filtered and concentrated. The resulting mixture was purified by silica gel chromatography (DCM/MeOH=10/1) to obtain the title compound (82 mg, 45%).

¹H NMR (300 MHz, DMSO-d₆) δ 9.44 (s, 1H), 7.79 (s, 1H), 7.56 (d, 1H), 7.20 (d, 1H), 4.55 (m, 1H), 2.66 (m, 2H), 2.38 (m, 2H), 2.31 (s, 3H), 1.93 (m, 2H), 1.74 (m, 2H), 1.46 (s, 9H).

Step 5: 4-(1-Methylpiperidine-4-yloxy)-3-(trifluoromethyl)benzeneamine

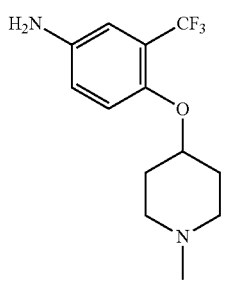 [SMILES: CN1CCC(Oc2ccc(N)cc2C(F)(F)F)CC1]

t-Butyl 4-(1-methylpiperidine-4-yloxy)-3-(trifluoromethyl)phenylcarbamate (82 mg, 0.299 mmol) was dissolved in methylene chloride (1 mL), and TFA (1 mL) was added thereto. The reaction mixture was stirred at room temperature for 2 hours and then concentrated. The reaction mixture was diluted with ethylene chloride and washed with sat. NaHCO₃ solution. The organic layer was dried with Na₂SO₄, filtered and concentrated to obtain the title compound (63 mg, 77%) without further purification.

¹H NMR (300 MHz, DMSO-d₆) δ 6.97 (dd, 1H), 6.79 (d, 1H), 6.73 (d, 1H), 5.00 (s, 2H), 4.26 (m, 1H), 2.50 (m, 2H), 2.13 (s, 3H), 2.10 (m, 2H), 1.86 (m, 2H), 1.61 (m, 2H).

The compound of Preparation Example 6 was prepared according to Reaction Scheme 11 below:

Reaction Scheme 11

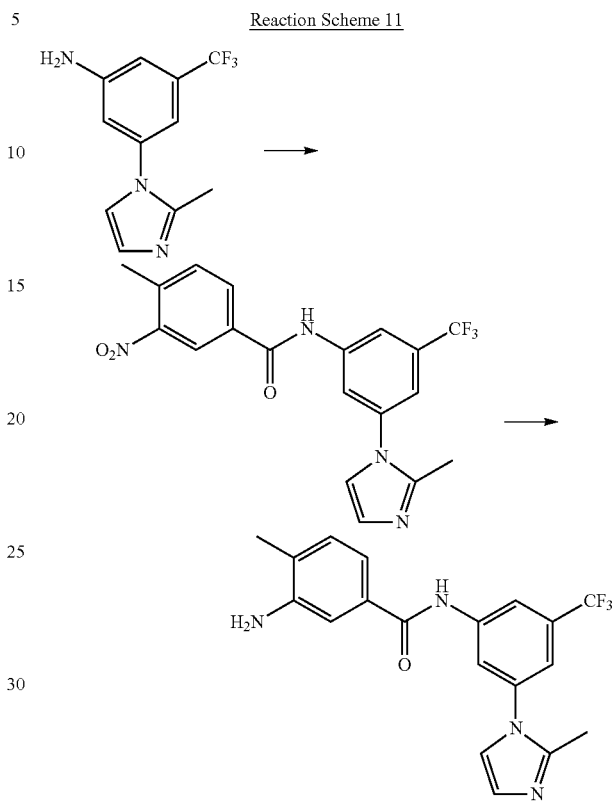

Preparation Example 6

3-Amino-4-methyl-N-(3-(2-methyl-1H-imidazole-1-yl)-5-(trifluoromethyl)phenyl)benzamide Step 1: 3-(2-Methyl-1H-imidazole-1-yl)-5-(trifluoromethyl)aniline

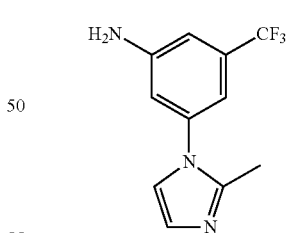

3-Bromo-5-(trifluoromethyl)aniline (1.2 mL, 8.60 mmol) and 2-methylimidazole (847 mg, 10.3 mmol) were dissolved in dimethyl sulfoxide (8.6 mL), and CuI (490 mg, 2.58 mmol), 8-quinolinol (370 mg, 2.58 mmol) and potassium carbonate (2.38 g, 17.2 mmol) were added thereto. The reaction mixture was treated with N₂ gas for 10 minutes to remove gas and subjected to a reaction at 120° C. for 12 hours. The reaction mixture was cooled to room temperature, and 14% aqueous ammonium hydroxide solution was added thereto. The reaction mixture was stirred for 1 hours at room temperature, diluted with ethyl acetate (30 mL) and washed with an aqueous sodium hydrogen carbonate solution (30 mL). The organic layer was washed with water, dried with sodium sulfate, and the solvent was distilled under reduced pressure. The concentrated mixture was filtered with a silica column using ethyl acetate to remove copper impurities, and the filtrate was distilled under reduced pressure. The concentrated mixture was crystallized with ethyl acetate (3 mL) and n-hexane (30 mL) to obtain the title compound (1.31 g) as a bright green solid.

$^1$H NMR (300 MHz, DMSO-d$_6$) δ 7.27 (s, 1H), 6.90 (s, 2H), 6.78 (s, 2H), 5.93 (s, 2H), 2.26 (s, 3H).

Step 2: 4-Methyl-N-(3-(2-methyl-1H-imidazole-1-yl)-5-(trifluoromethyl)phenyl)-3-nitrobenzamide

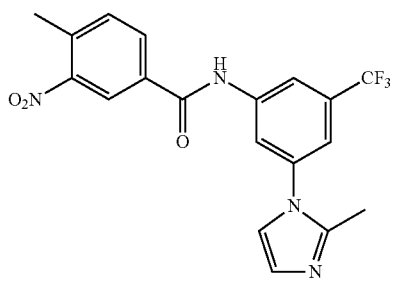 [SMILES: Cc1ccc(C(=O)Nc2cc(-n3ccnc3C)cc(C(F)(F)F)c2)cc1[N+](=O)[O-]]

3-Nitro-4-methyl benzoic acid (14.8 g, 81.5 mmol) was dissolved in DMF (150 mL), and HATU (62 g, 163 mmol) and DIPEA (57 mL, 326 mmol) were added thereto at room temperature. The reaction mixture was stirred for 15 minutes, 3-(2-methyl-1H-imidazole-1-yl)-5-(trifluoromethyl)aniline (13.1 g, 54.3 mmol) was added thereto and stirred at 45° C. for 16 hours. The reaction mixture was cooled to room temperature, diluted with ethyl acetate and washed with sat. NaHCO$_3$ solution. The organic layer was dried with anhydrous MgSO$_4$, filtered with Celite and concentrated. The residue was crystallized with ethyl acetate and hexane to obtain the title compound (27 g).

$^1$H NMR (300 MHz, DMSO-d$_6$) δ 10.9 (s, 1H), 8.61 (s, 1H), 8.25-8.22 (m, 2H), 8.16 (s, 1H), 7.74-7.71 (d, 1H), 7.62 (s, 1H), 7.41 (s, 1H), 6.95 (s, 1H), 2.55 (s, 3H), 2.34 (s, 3H).

Step 3: 3-Amino-4-methyl-N-(3-(2-methyl-1H-imidazole-1-yl)-5-(trifluoromethyl)phenyl)benzamide

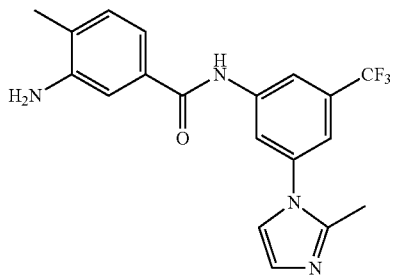

The compound (27 g, 72.1 mmol) obtained in Step 2 of Preparation Example 6 was dissolved in ethanol (300 mL), SnCl$_2$.2H$_2$O (81 g, 360 mmol) was added thereto and stirred at 80° C. for 3 hours. The reaction mixture was cooled to room temperature and diluted with ethyl acetate. The organic layer was washed with sat. NaHCO$_3$ solution several times. The organic layer was dried with anhydrous MgSO$_4$, filtered and concentrated to obtain the title compound without further purification.

MS m/z [M+1] 375.25.

Example 22

4-(Cyclopropylamino)-N-(2-methyl-5-(3-(2-methyl-1H-imidazole-1-yl)-5-(trifluoromethyl)phenylcarbamoyl)phenyl)thieno[3,2-d]pyrimidine-7-carboxamide

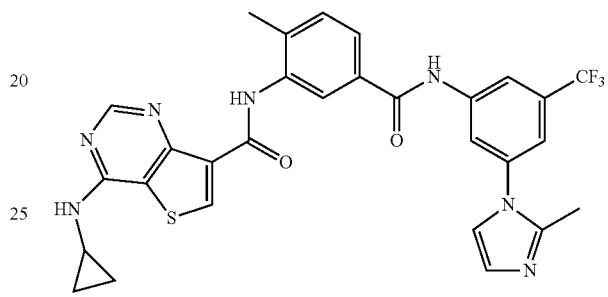

The compound (7.2 g, 31 mmol) obtained in Step 3 of Preparation Example 4 was dissolved in DMF (100 mL) and then HATU (25 g, 65.4 mmol) and DIPEA (23 mL, 131 mmol) were added thereto at room temperature. The reaction mixture was stirred for 15 minutes, 3-amino-4-methyl-N-(3-(2-methyl-1H-imidazole-1-yl)-5-(trifluoromethyl)phenyl)benzamide (8.2 g, 22 mmol) obtained in Step 3 of Preparation Example 6 was added thereto and stirred at 45° C. for 16 hours. The reaction mixture was cooled to room temperature, diluted with ethyl acetate and washed with sat. NaHCO$_3$ solution. The organic layer was dried with anhydrous MgSO$_4$, filtered with Celite and concentrated. The residue was crystallized with ethyl acetate and hexane to obtain the title compound (5 g).

$^1$H NMR (DMSO-d$_6$) δ 11.9 (s, 1H), 10.8 (s, 1H), 8.98 (s, 1H), 8.90 (s, 1H), 8.67 (s, 1H), 8.52 (s, 1H), 8.31 (s, 1H), 8.18 (s, 1H), 7.73 (d, 1H), 7.58 (s, 1H), 7.50 (d, 1H), 7.42 (s, 1H), 6.95 (s, 1H), 3.04 (m, 1H), 2.55 (s, 3H), 2.35 (s, 3H), 0.84 (m, 2H), 0.69 (m, 2H).

The compound of Preparation Example 7 was prepared according to Reaction Scheme 12 below:

Reaction Scheme 12

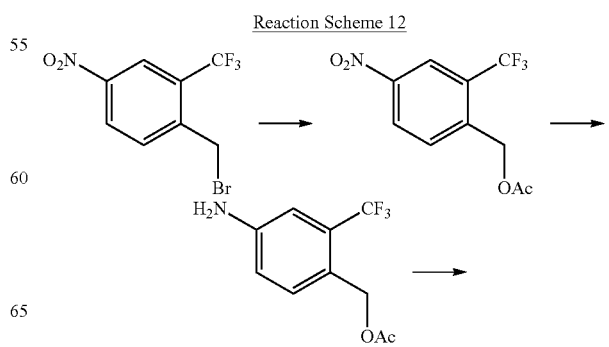

43
-continued

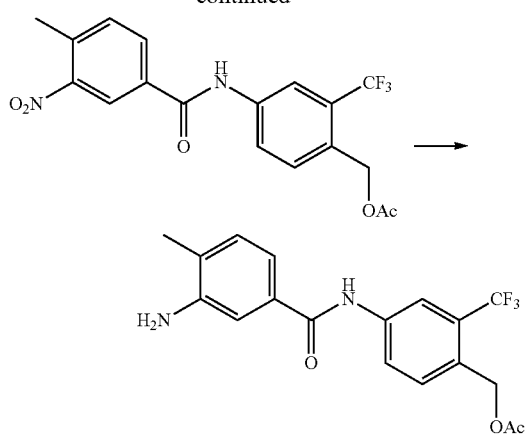

Preparation Example 7

4-(3-Amino-4-methylbenzamido)-2-(trifluoromethyl)benzyl acetate

Step 1:
1-(Bromomethyl)-4-nitro-2-(trifluoromethyl)benzene

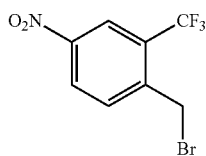 [SMILES: O=[N+]([O-])c1ccc(CBr)c(C(F)(F)F)c1]

The procedure of Step 3 of Preparation Example 3 was repeated except for using 1-methyl-4-nitro-2-(trifluoromethyl)benzene as a starting material to obtain the title compound.

MS m/z [M+1] 283.09, 285.97.

Step 2: 4-Nitro-2-(trifluoromethyl)benzyl acetate

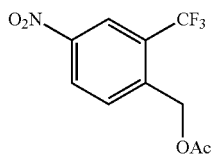

The procedure of Step 4 of Preparation Example 3 was repeated except for using the compound obtained in Step 1 of Preparation Example 7 as a starting material to obtain the title compound.

MS m/z [M+1] 264.05.

44

Step 3: 4-Amino-2-(trifluoromethyl)benzyl acetate

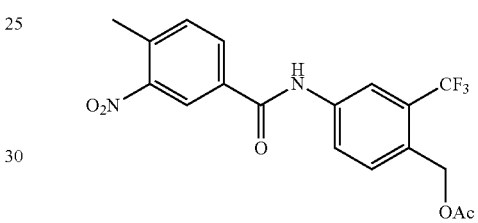

The procedure of Step 2 of Example 1 was repeated except for using the compound obtained in Step 2 of Preparation Example 7 as a starting material to obtain the title compound.

$^1$H NMR (400 MHz, DMSO-d$_6$) δ 7.24 (d, 1H), 6.91 (d, 1H), 6.76 (dd, 1H), 5.71 (s, 2H), 4.99 (s, 2H), 2.00 (s, 3H)

Step 4: 4-(4-Methyl-3-nitrobenzamido)-2-(trifluoromethyl)benzyl acetate

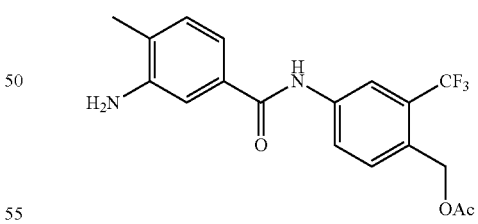

The procedure of Step 2 of Preparation Example 6 was repeated except for using the compound obtained in Step 3 of Preparation Example 7 as a starting material to obtain the title compound.

MS m/z [M+1] 397.10.

Step 5: 4-(3-Amino-4-methylbenzamido)-2-(trifluoromethyl)benzyl acetate

The procedure of Step 3 of Preparation Example 6 was repeated except for using the compound obtained in Step 4 of Preparation Example 7 as a starting material to obtain the title compound.

$^1$H NMR (400 MHz, DMSO-d$_6$) δ 10.36 (s, 1H), 8.27 (s, 1H), 8.08 (d, 1H), 7.62 (d, 1H), 7.18 (s, 1H), 7.08 (q, 2H), 5.17 (s, 2H), 5.11 (s, 2H), 2.12 (s, 3H), 2.07 (s, 3H); MS m/z [M+1] 368.98.

The compounds of Examples 23 to 26 were prepared according to Reaction Scheme 13 below:

Reaction Scheme 13

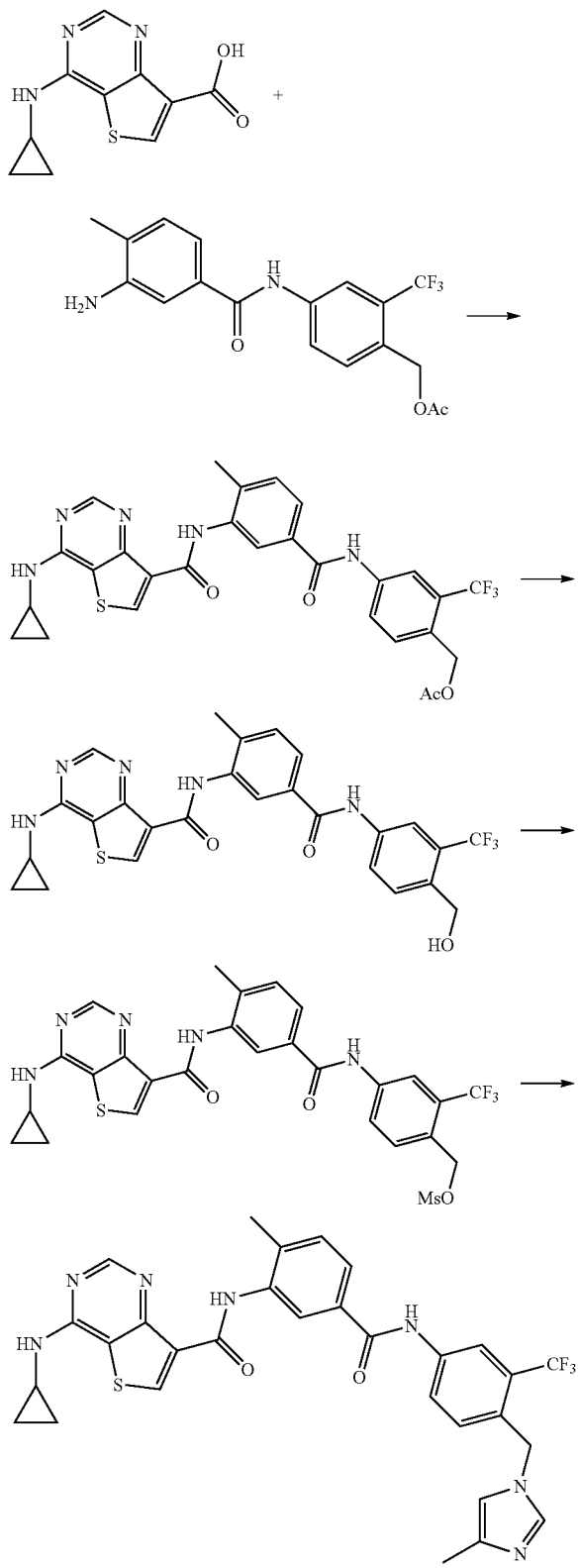

Example 23

4-(3-(4-(Cyclopropylamino)thieno[3,2-d]pyrimidine-7-carboxamido)-4-methylbenzamido)-2-(trifluoromethyl)benzyl acetate

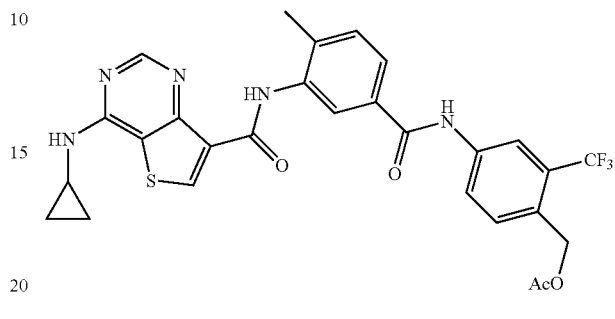

The procedure of Example 22 was repeated except for using the compound obtained in Preparation Example 7 instead of 3-amino-4-methyl-N-(3-(2-methyl-1H-imidazole-1-yl)-5-(trifluoromethyl)phenyl)benzamide to obtain the title compound.

$^1$H NMR (400 MHz, DMSO-$d_6$) δ 11.91 (s, 1H), 10.60 (s, 1H), 8.99 (br s, 1H), 8.89 (s, 1H), 8.69 (br s, 1H), 8.53 (br s, 1H), 8.29 (s, 1H), 8.12 (d, 1H), 7.71 (d, 1H), 7.65 (d, 1H), 7.18 (d, 1H), 5.19 (s, 2H), 3.06-3.04 (m, 1H), 2.89 (s, 3H), 2.08 (s, 3H), 0.85-0.80 (m, 2H), 0.70-0.64 (m, 2H); MS m/z [M+1] 584.04.

Example 24

4-(Cyclopropylamino)-N-(5-(4-(hydroxymethyl)-3-(trifluoromethyl)phenylcarbamoyl)-2-methylphenyl)thieno[3,2-d]pyrimidine-7-carboxamide

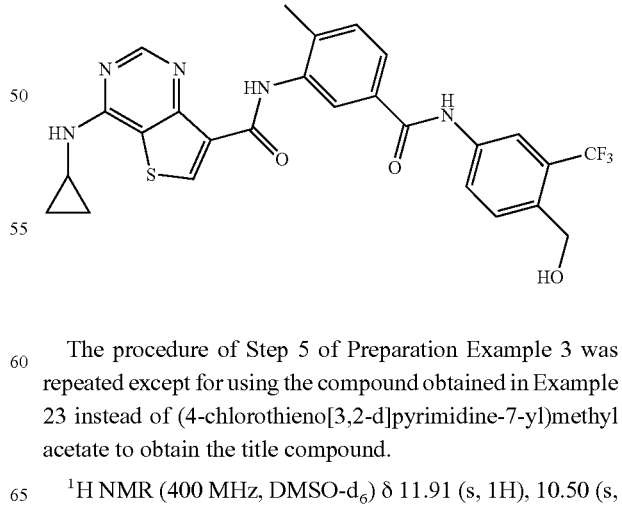

The procedure of Step 5 of Preparation Example 3 was repeated except for using the compound obtained in Example 23 instead of (4-chlorothieno[3,2-d]pyrimidine-7-yl)methyl acetate to obtain the title compound.

$^1$H NMR (400 MHz, DMSO-$d_6$) δ 11.91 (s, 1H), 10.50 (s, 1H), 8.99 (br s, 1H), 8.88 (s, 1H), 8.68 (br s, 1H), 8.52 (br s, 1H), 8.20 (s, 1H), 8.08 (d, 1H), 7.72 (dd, 2H), 7.47 (d, 1H), 5.44 (br s, 1H), 4.64 (d, 2H), 3.09-3.05 (m, 1H), 2.70 (s, 3H), 0.92-0.80 (m, 2H), 0.76-0.65 (m, 2H); MS m/z [M+1] 541.96.

Example 25

4-(3-(4-(Cyclopropylamino)thieno[3,2-d]pyrimidine-7-carboxamido)-4-methylbenzamido)-2-(trifluoromethyl)benzyl methanesulfonate

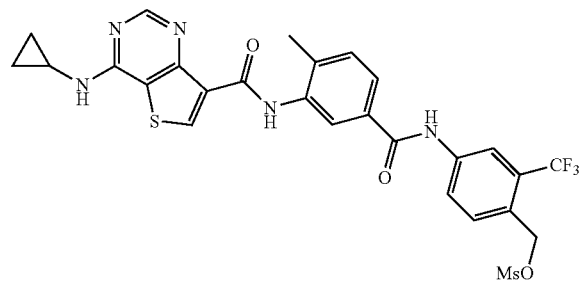 [SMILES: Cc1ccc(C(=O)Nc2ccc(COS(C)(=O)=O)c(C(F)(F)F)c2)cc1NC(=O)c1csc2c(NC3CC3)ncnc12]

4-(Cyclopropylamino)-N-(5-(4-(hydroxymethyl)-3-(trifluoromethyl)phenylcarbamoyl)-2-methylphenyl)thieno[3,2-d]pyrimidine-7-carboxamide (300 mg, 0.554 mmol) was dissolved in DCM (2.5 mL), and TEA (0.15 mL, 1.11 mmol) was added thereto. Methanesulfonyl chloride (66 μL, 0.83 mmol) was added to the reaction mixture at 0° C. The reaction mixture was stirred for 6 hours and diluted with DCM (10 mL). The organic layer was washed with brine, dried with MgSO$_4$, filtered and concentrated under reduced pressure to obtain the title compound without further purification.

$^1$H NMR (400 MHz, DMSO-d$_6$) δ 11.92 (s, 1H), 10.63 (s, 1H), 8.99 (br s, 1H), 8.89 (s, 1H), 8.68 (br s, 1H), 8.52 (br s, 1H), 8.28 (s, 1H), 8.14 (d, 1H), 7.72 (dd, 2H), 7.49 (d, 1H), 4.86 (s, 2H), 3.12-3.05 (m, 1H), 2.67 (s, 3H), 1.20 (s, 3H), 0.92-0.87 (m, 2H), 0.74-0.60 (m, 2H); MS m/z [M+1] 619.98

Example 26

4-(Cyclopropylamino)-N-(2-methyl-5-(4-((4-methyl-1H-imidazole-1-yl)methyl)-3-(trifluoromethyl)phenylcarbamoyl)phenyl)thieno[3,2-d]pyrimidine-7-carboxamide

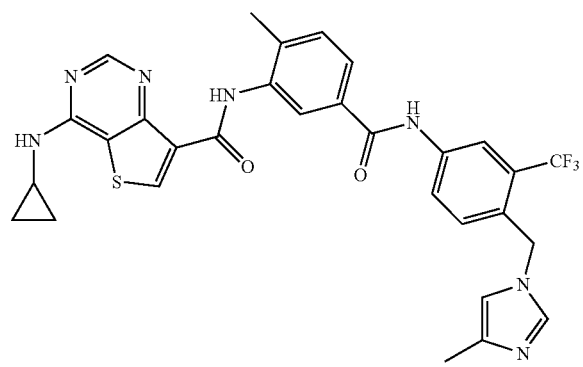 [SMILES: Cc1cn(Cc2ccc(NC(=O)c3ccc(C)c(NC(=O)c4csc5c(NC6CC6)ncnc45)c3)cc2C(F)(F)F)cn1]

4-(3-(4-(Cyclopropylamino)thieno[3,2-d]pyrimidine-7-carboxamido)-4-methylbenzamido)-2-(trifluoromethyl)benzyl methanesulfonate (30 mg, 0.048 mmol) was dissolved in DMF (1 mL), K$_2$CO$_3$ (20 mg, 0.145 mmol) and 4-methyl-1H-imidazole (20 mg, 0.242 mmol) were added thereto and stirred at room temperature for 18 hours. The reaction mixture was diluted with ethyl acetate (10 mL) and washed with brine. The organic layer was dried with MgSO$_4$, filtered and concentrated under reduced pressure. The resulting mixture was purified by silica gel chromatography (MeOH/DCM=5/95) to obtain the title compound (23 mg, 78% yield).

$^1$H NMR (400 MHz, DMSO-d$_6$) δ 11.94 (s, 1H), 10.74 (s, 1H), 8.99 (br s, 1H), 8.93 (s, 1H), 8.68 (br s, 1H), 8.53 (br s, 1H), 8.41 (s, 1H), 8.21 (s, 1H), 7.82 (s, 1H), 7.74 (d, 2H), 7.51 (d, 1H), 4.47 (s, 2H), 3.09-3.02 (m, 1H), 2.24 (s, 3H), 1.17-1.00 (m, 2H), 0.85-0.78 (m, 2H).

Example 27

4-(Cyclopropylamino)-N-(2-methyl-5-(3-(4-methyl-1H-imidazole-1-yl)-5-(trifluoromethyl)phenylcarbamoyl)phenyl)thieno[3,2-d]pyrimidine-7-carboxamide The procedure of Step 5 of Example 1 was repeated except for using 3-(4-(cyclopropylamino)thieno[3,2-d]pyrimidine-7-carboxamido)-4-methylbenzoic acid obtained in Step 3 of Example 21 and 3-(4-methyl-1H-imidazole-1-yl)-5-(trifluoromethyl)aniline to obtain the title compound (see Table 1).

Example 28

N-(5-(3-bromo-5-(trifluoromethylcarbamoyl)phenyl)-2-methylphenyl)-4-(cyclopropylamino)thieno[3,2-d]pyrimidine-7-carboxamide The procedure of Step 5 of Example 1 was repeated except for using 3-(4-(cyclopropylamino)thieno[3,2-d]pyrimidine-7-carboxamido)-4-methylbenzoic acid obtained in Step 3 of Example 21 and 3-bromo-5-(trifluoromethyl)aniline to obtain the title compound (see Table 1).

Example 29

4-(Cyclopropylamino)-N-(2-methyl-5-(6-morpholinopyridine-3-ylcarbamoyl)phenyl)thieno[3,2-d]pyrimidine-7-carboxamide The procedure of Step 5 of Example 1 was repeated except for using 3-(4-(cyclopropylamino)thieno[3,2-d]pyrimidine-7-carboxamido)-4-methylbenzoic acid obtained in Step 3 of Example 21 and 6-morpholinopyridine-3-amine to obtain the title compound (see Table 1).

Example 30

4-(Cyclopropylamino)-N-(5-(6-(4-ethylpiperazine-1-yl)pyridine-3-ylcarbamoyl)-2-methylphenyl)thieno[3,2-d]pyrimidine-7-carboxamide The procedure of Step 5 of Example 1 was repeated except for using 3-(4-(cyclopropylamino)thieno[3,2-d]pyrimidine-7-carboxamido)-4-methylbenzoic acid obtained in Step 3 of Example 21 and 6-(4-ethylpiperazine-1-yl)pyridine-3-amine to obtain the title compound (see Table 1).

Examples 31, and 34 to 38

The procedure of Example 22 was repeated except for using an appropriate starting compound (see Table 1).

Examples 32 and 33

The procedure of Example 26 was repeated except for using an appropriate starting compound (see Table 1).

The compound of Example 39 was prepared according to Reaction Scheme 14 below:

Reaction Scheme 14

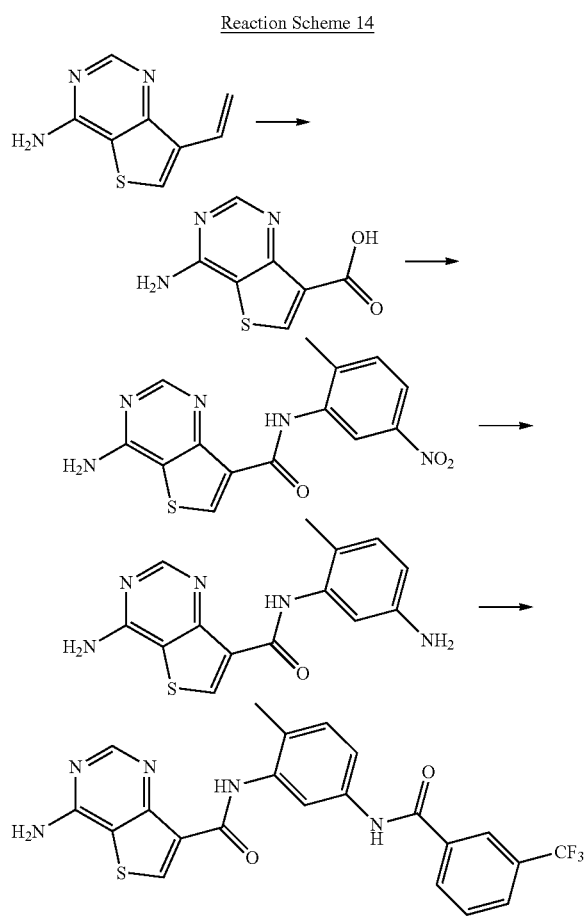

Example 39

4-Amino-N-(2-methyl-5-(3-(trifluoromethyl)benzamido)phenyl)thieno[3,2-d]pyrimidine-7-carboxamide Step 1:
4-Aminothieno[3,2-d]pyrimidine-7-carboxylic acid

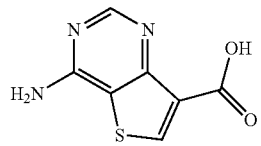

The procedures of Steps 2 and 3 of Preparation Example 2 was repeated except for using the compound obtained in Step 2 of Example 1 as a starting material to obtain the title compound.
MS m/z [M+1] 196.03.

Step 2: 4-Amino-N-(2-methyl-5-nitrophenyl) thieno[3,2-d]pyrimidine-7-carboxamide

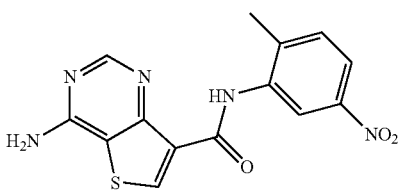 [SMILES: Cc1ccc([N+](=O)[O-])cc1NC(=O)c1csc2c(N)ncnc12]

The procedure of Example 8 was repeated except for using the compound obtained in Step 1 of Example 39 as a starting material to obtain the title compound.
$^1$H NMR (300 MHz, DMSO-$d_6$) δ 12.12 (s, 1H), 9.26 (d, 1H), 8.95 (s, 1H), 8.61 (s, 1H), 7.85 (dd, 1H), 7.84 (br s, 2H), 7.55 (d, 1H), 2.60 (s, 3H). MS m/z [M+1] 330.06.

Step 3: 4-Amino-N-(5-amino-2-methylphenyl) thieno[3,2-d]pyrimidine-7-carboxamide

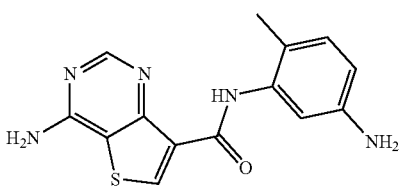 [SMILES: Cc1ccc(N)cc1NC(=O)c1csc2c(N)ncnc12]

The compound (1 g, 3.0 mmol) obtained in Step 2 of Example 39 was added to methanol (15 mL) and Pd/C (200 mg), and stirred under $H_2$ atmosphere for 14 hours at room temperature. The reaction mixture was filtered using Celite and concentrated to obtain the title compound (152 mg).
$^1$H NMR (300 MHz, DMSO-$d_6$) δ 11.48 (s, 1H), 8.86 (s, 1H), 8.54 (s, 1H), 7.88 (br s, 2H), 7.59 (d, 1H), 6.88 (d, 1H), 6.27 (dd, 1H), 4.92 (br s, 2H), 2.27 (s, 3H). MS m/z [M+1] 300.09.

Step 4: 4-Amino-N-(2-methyl-5-(3-(trifluoromethyl) benzamido)phenyl)thieno[3,2-d]pyrimidine-7-carboxamide

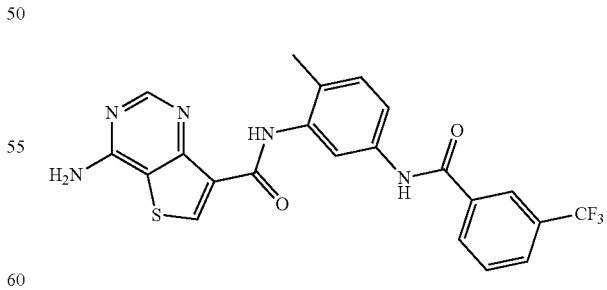

4-Amino-N-(5-amino-2-methylphenyl)thieno[3,2-d]pyrimidine-7-carboxamide (30 mg, 0.1 mmol) was dissolved in THF (1 mL) and TEA (42 μL, 0.30 mmol) was added thereto. 3-(trifluoromethyl)benzoyl chloride (19 μL, 0.13 mmol) was added to reaction mixture at 0° C. and stirred at room temperature for 6 hours. The reaction mixture was diluted with ethyl acetate (10 mL) and washed with brine. The organic layer was dried with MgSO₄, filtered and concentrated under reduced pressure. The resulting mixture was purified by silica gel chromatography (3/97 MeOH/DCM) to obtain the title compound (35 mg, 74% yield).

¹H NMR (300 MHz, DMSO-d₆) δ 11.74 (s, 1H), 10.51 (s, 1H), 8.92 (s, 1H), 8.67 (s, 1H), 8.58 (s, 1H), 8.31 (s, 1H), 8.28 (d, 1H), 7.96 (d, 1H), 7.94 (s, 2H), 7.77 (t, 1H), 7.58 (d, 1H), 7.27 (d, 1H), 2.44 (s, 3H).

The compound of Preparation Example 8 was prepared according to Reaction Scheme 15 below:

Reaction Scheme 15

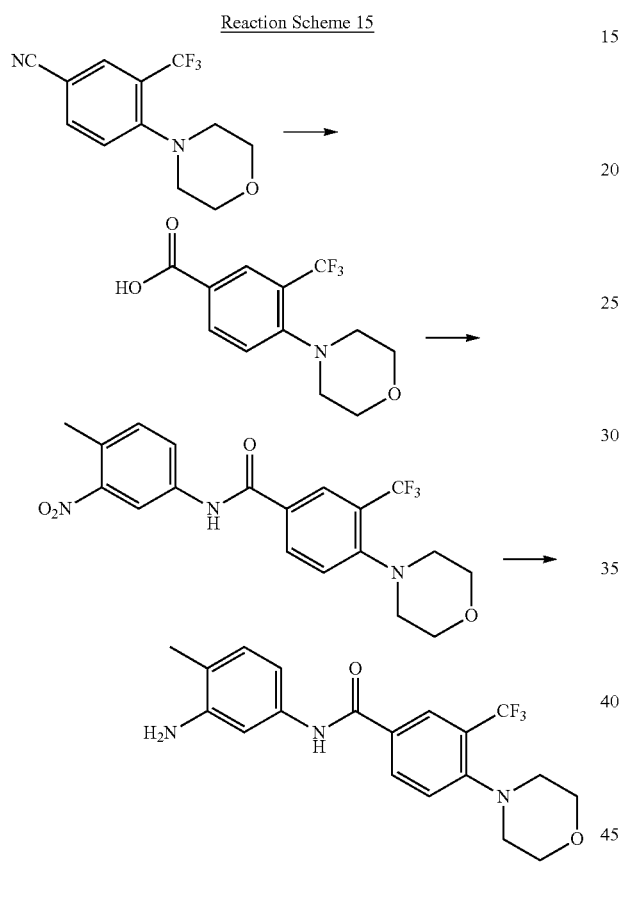

Preparation Example 8

N-(3-amino-4-methylphenyl)-4-morpholino-3-(trifluoromethyl)benzamide

Step 1: 4-Morpholino-3-(trifluoromethyl)benzonitrile

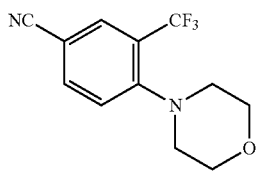

4-Fluoro-3-(trifluoromethyl)benzonitrile (2.0 g, 10.58 mmol) was dissolved in dimethyl acetamide (35 mL), mor-pholine (2.88 mL, 31.73 mmol) was added thereto, and the mixture was subjected to a reaction at 145° C. for 19 hours. The reaction mixture was cooled to room temperature, diluted with ethyl acetate (50 mL), and the organic layer was washed with an aqueous sodium hydrogen carbonate solution (50 mL). The organic layer was washed with water, dried with sodium sulfate, and the solvent was distilled under reduced pressure. The concentrated mixture was crystallized with ethyl acetate (10 mL) and n-hexane (80 mL) to obtain the title compound as a brown solid (2.1 g).

¹H NMR (DMSO-d₆) δ 8.17 (s, 1H), 8.08 (d, 1H), 7.58 (d, 1H), 3.71 (m, 4H), 2.99 (m, 4H).

Step 2: 4-Morpholino-3-(trifluoromethyl)benzoic acid

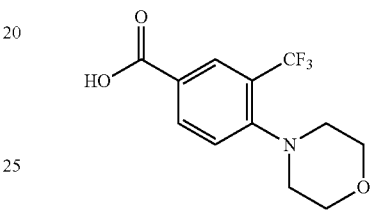

4-Morpholino-3-(trifluoromethyl)benzonitrile (2.1 g, 8.016 mmol) was dissolved in a mixture of tetrahydrofurane/methanol/water (1:1:1, v/v/v, 20 mL), sodium hydroxide (1.9 g, 48.10 mmol) was added thereto and stirred for 40 hours with reflux. The reaction mixture was cooled to room temperature and 1N hydrochloride was added slowly thereto to pH 3~4. The resulting solid was filtered, washed with water and dimethyl ether and then dried to obtain the title compound (694 mg).

¹H NMR (300 MHz, DMSO-d₆) δ 8.15 (d, 2H), 7.57 (d, 1H), 3.70 (m, 4H), 2.95 (m, 4H).

Step 3: N-(4-methyl-3-nitrophenyl)-4-morpholino-3-(trifluoromethyl)benzamide

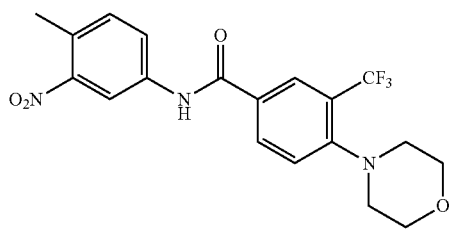 [SMILES: Cc1ccc(NC(=O)c2ccc(N3CCOCC3)c(C(F)(F)F)c2)cc1[N+](=O)[O-]]

4-Morpholino-3-(trifluoromethyl)benzoic acid (694 mg, 2.523 mmol) was dissolved in dimethylformamide (5.6 mL), HATU (1.92 g, 5.047 mmol) and N,N-diisopropylethylamine (1.37 mL, 7.851 mmol) were added thereto and stirred at room temperature for 30 minutes. 4-Methyl-3-nitroaniline (256 mg, 1.682 mmol) was added to the reaction mixture and subjected to a reaction at 45° C. for 19 hours. After cooling to room temperature the reaction mixture was diluted with ethyl acetate (10 mL) and washed with an aqueous sodium hydrogen carbonate solution (10 mL). The organic layer was washed with water, dried with sodium sulfate, and the solvent was distilled under reduced pressure. The concentrated mixture was crystallized using ethyl acetate (3 mL) n-hexane (30 mL) to obtain the title compound (673 mg) as a brown solid.

$^1$H NMR (300 MHz, DMSO-d$_6$) δ=10.7 (s, 1H), 8.50 (s, 1H), 8.25 (m, 2H), 7.98 (d, 1H), 7.65 (d, 1H), 7.49 (d, 1H), 3.72 (m, 4H), 2.96 (m, 4H).

Step 4: N-(3-amino-4-methylphenyl)-4-morpholino-3-(trifluoromethyl)benzoamide

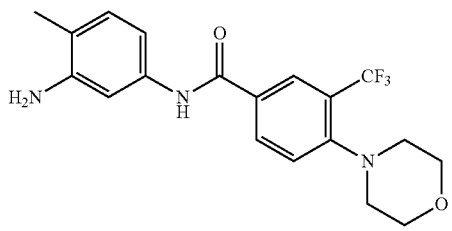

N-(4-methyl-3-nitrophenyl)-4-morpholino-3-(trifluoromethyl)benzoamide (68 mg, 0.17 mmol) was dissolved in ethanol (1.7 mL), tin chloride (190 mg, 0.83 mmol) was added thereto, and the mixture was subjected to a reaction with reflux for 3 hours. The reaction mixture was cooled to room temperature, diluted with ethyl acetate and then washed with an aqueous sodium hydrogen carbonate solution. The organic layer was washed with distilled water (10 mL×3), dried with sodium sulfate, and the solvent was distilled under reduced pressure. The concentrated solution was crystallized using ethyl acetate (2 mL) and n-hexane (20 mL) to obtain the title compound as a bright yellow solid (26 mg).

$^1$H NMR (300 MHz, DMSO-d$_6$) δ 10.0 (s, 1H), 8.21 (m, 2H), 7.61 (d, 1H), 7.07 (s, 1H), 6.87 (d, 1H), 6.81 (d, 1H), 4.84 (s, 2H), 3.72 (m, 4H), 2.94 (m, 4H), 2.04 (s, 3H).

Example 40

4-(Cyclopropylamino)-N-(2-methyl-5-(4-morpholino-3-(trifluoromethyl)benzamido)phenyl)thieno pyrimidine-7-carboxamide

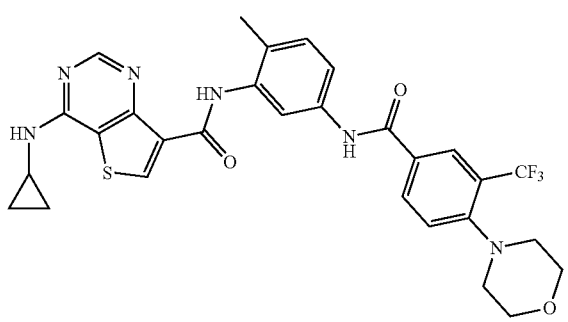 [SMILES: Cc1ccc(NC(=O)c2ccc(N3CCOCC3)c(C(F)(F)F)c2)cc1NC(=O)c1csc2c(NC3CC3)ncnc12]

4-(Cyclopropylamino)thieno[3,2-d]pyrimidine-7-carboxylic acid (23 mg, 0.10 mmol) was dissolved in dimethylformamide 1.0 mL, HATU (76 mg, 0.20 mmol) and N,N-diisopropylethylamine (0.081 mL, 0.47 mmol) was added thereto, and the mixture was stirred at room temperature for 30 minutes. N-(3-amino-4-methylphenyl)-4-morpholino-3-(trifluoromethyl)benzoamide (25 mg, 0.066 mmol) was added to the reaction mixture and subjected to a reaction at 45° C. for 17 hours. After cooling to room temperature the reaction mixture was diluted with ethyl acetate (5 mL) and washed with an aqueous sodium hydrogen carbonate solution (5 mL). The organic layer was washed with brine (5 mL×3), dried with sodium sulfate, and the solvent was distilled under reduced pressure. The concentrated reactant was crystallized using ethyl acetate (1 mL) and n-hexane (10 mL) to obtain the title compound as a bright brown solid (34 mg).

$^1$H NMR (300 MHz, DMSO-d$_6$) δ 11.8 (s, 1H), 10.4 (s, 1H), 8.95 (s, 1H), 8.66 (d, 2H), 8.50 (s, 1H), 8.26 (d, 2H), 7.65 (d, 1H), 7.50 (d, 1H), 7.27 (d, 1H), 3.74 (m, 4H), 3.03 (m, 1H), 2.98 (m, 4H), 2.48 (s, 3H), 0.85 (m, 2H), 0.68 (m, 2H).

The compound of Preparation Example 9 was prepared according to Reaction Scheme 16 below:

Reaction Scheme 16

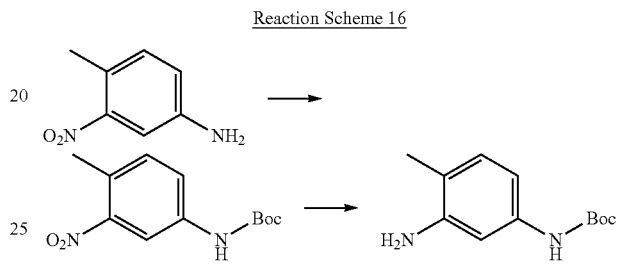

Preparation Example 9 t-Butyl 3-amino-4-methylphenylcarbamate

Step 1: t-Butyl 4-methyl-3-nitrophenylcarbamate

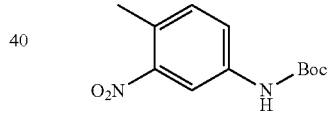

4-Methyl-3-nitroaniline (5.0 g, 32.86 mmol) was dissolved in anhydrous THF (25 mL). t-Butyl bicarbonate (7.5 mL, 32.86 mmol) dissolved in anhydrous THF (25 mL) was added slowly to the reaction mixture, which was stirred at 65° C. for 18 hours. After the reaction was completed the remaining organic solvent was distilled under reduced pressure, and water was added thereto. The resulting yellow solid was filtered and dried to obtain the title compound without further purification.

$^1$H NMR (400 MHz, DMSO-d$_6$) δ9.76 (s, 1H), 8.23 (d, 1H), 7.57 (dd, 1H), 7.39 (d, 1H), 2.43 (s, 3H), 1.48 (s, 9H).

Step 2: t-Butyl 3-amino-4-methylphenylcarbamate

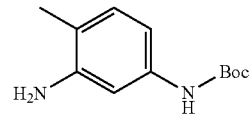

t-Butyl 4-methyl-3-nitrophenylcarbamate (7.6 g, 30.13 mmol) was dissolved in ethanol (167 mL) and subjected to a reaction under 50 psi H₂ gas. The reaction mixture was stirred for 2 hours and then concentrated by filtering with Celite to obtain the title compound without further purification.

¹H NMR (400 MHz, DMSO-d₆) δ 8.92 (s, 1H), 6.82 (s, 1H), 6.64 (d, 1H), 6.48 (d, 1H), 4.73 (s, 2H), 1.88 (s, 3H), 1.44 (s, 9H).

The compound of Example 82 was prepared according to Reaction Scheme 17 below:

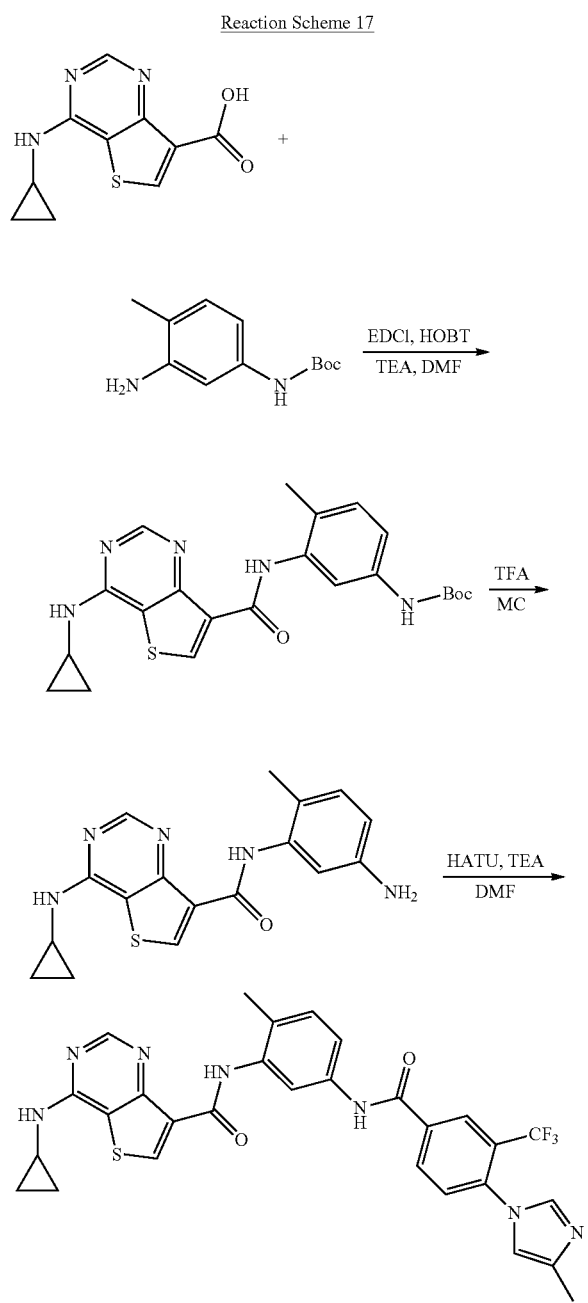

Reaction Scheme 17

Example 82

4-(Cyclopropylamino)-N-(2-methyl-5-(4-(4-methyl-1H-imidazole-1-yl)-3-(trifluoromethyl)benzoamido)phenyl)thieno[3,2-d]pyrimidine-7-carboxamide Step 1: t-Butyl 3-(4-(cyclopropylamino)thieno[3,2-d]pyrimidine-7-carboxamido)-4-methylphenylcarbamate

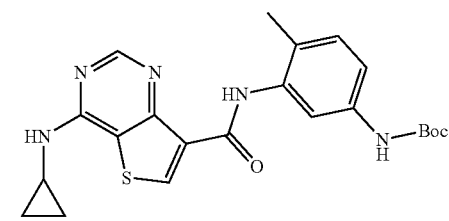 [SMILES: Cc1ccc(NC(=O)OC(C)(C)C)cc1NC(=O)c1csc2c(NC3CC3)ncnc12]

4-(Cyclopropylamino)thieno[3,2-d]pyrimidine-7-carboxylic acid (5.3 g, 22.49 mmol) obtained in Step 3 of Preparation Example 4 was dissolved in DMF (60 mL). t-Butyl 3-amino-4-methylphenylcarbamate (6 g, 26.99 mmol) obtained in Step 2 of Preparation Example 9, EDCI (6.5 g, 33.74 mmol), HOBT (6.1 g, 44.98 mmol) and TEA (4.7 mL, 33.74 mmol) were sequentially added to the reaction mixture, which was stirred at room temperature for 24 hours. After the reaction was completed water (120 mL) was added thereto, and the resulting yellow solid was filtered and dried to obtain the title compound without further purification.

MS m/z [M+1] 439.84.

Step 2: N-(5-amino-2-methylphenyl)-4-(cyclopropylamino)thieno[3,2-d]pyrimidine-7-carboxamide

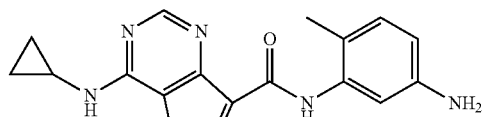

t-Butyl 3-(4-(cyclopropylamino)thieno[3,2-d]pyrimidine-7-carboxamido)-4-methylphenylcarbamate (7 g, 15.93 mmol) was dissolved in DCM (80 mL), TFA (12 mL, 159.3 mmol) was added thereto, and the mixture was stirred at room temperature for 8 hours. After the reaction was completed, the reaction mixture was concentrated under reduced pressure to remove the organic solvent and the remaining TFA, and water (20 mL) was added thereto. The reaction mixture was neutralized with 2.0 N NaOH solution, and the resulting yellow solid was filtered and dried to obtain the title compound without further purification.

MS m/z [M+1] 339.87

Step 3: 4-(Cyclopropylamino)-N-(2-methyl-5-(4-(4-methyl-1H-imidazole-1-yl)-3-(trifluoromethyl)benzoamido)phenyl)thieno[3,2-d]pyrimidine-7-carboxamide

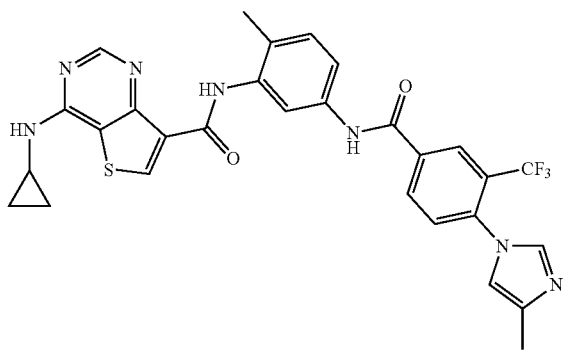 [SMILES: Cc1cn(-c2ccc(C(=O)Nc3ccc(C)c(NC(=O)c4csc5c(NC6CC6)ncnc45)c3)cc2C(F)(F)F)cn1]

The procedure of Step 5 of Example 1 was repeated except for using N-(5-amino-2-methylphenyl)-4-(cyclopropylamino)thieno[3,2-d]pyrimidine-7-carboxamide and 4-(4-methyl-1H-imidazole-1-yl)-3-(trifluoromethyl)benzoic acid to obtain the title compound.

$^1$H NMR (300 MHz, DMSO-$d_6$) δ 11.8 (s, 1H), 10.6 (s, 1H), 8.93 (s, 1H), 8.67 (d, 2H), 8.47 (s, 2H), 8.39 (d, 1H), 7.94 (s, 1H), 7.75 (d, 1H), 7.60 (m, 1H), 7.29 (m, 1H), 7.11 (s, 1H), 3.05 (m, 1H), 2.18 (s, 3H), 0.84 (m, 2H), 0.66 (m, 2H)

Examples 41 to 81 and Examples 83 to 121

The procedure of Example 39, 40 or 82 was repeated except for using an appropriate starting compound (see Table 1).

Example 122

4-Amino-N-(5-(3-(4-chloro-3-(trifluoromethyl)phenyl)ureido)-2-methylphenyl)thieno[3,2-d]pyrimidine-7-carboxamide

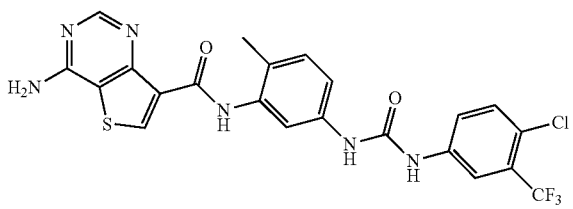 [SMILES: Cc1ccc(NC(=O)Nc2ccc(Cl)c(C(F)(F)F)c2)cc1NC(=O)c1csc2c(N)ncnc12]

4-Amino-N-(5-amino-2-methylphenyl)thieno[3,2-d]pyrimidine-7-carboxamide (50 mg, 0.167 mmol) obtained in Step 3 of Example 39 was dissolved in anhydrous THF (1 mL), TEA (47 μL, 0.334 mmol) and triphosgene (17 mg, 0.059 mmol) were added thereto at 0° C., and the mixture was stirred for 2 hours. 4-Chloro-3-(trifluoromethyl)benzeneamine (49 mg, 0.251 mmol) was added to the reaction mixture, which was stirred at room temperature for 10 hours. The reaction mixture was diluted with ethyl acetate (10 mL) and washed with brine. The organic layer was dried with MgSO$_4$, filtered and then concentrated under reduced pressure. The resulting mixture was purified by silica gel chromatography (MeOH/DCM=3/97) to obtain the title compound (54 mg, 60%).

$^1$H NMR (300 MHz, DMSO-$d_6$) δ 11.70 (s, 1H), 9.01 (s, 1H), 8.91 (s, 1H), 8.87 (s, 1H), 8.56 (s, 1H), 8.40 (s, 1H), 8.11 (s, 1H), 7.89 (br s, 2H), 7.60 (m, 2H), 7.28 (d, 1H), 7.18 (d, 1H), 2.40 (s, 3H).

Example 123

4-(Cyclopropylamino)-N-(2-methyl-5-(3-(3-(4-methyl-1H-imidazole-1-yl)-5-(trifluoromethyl)phenyl)ureido)phenyl)thieno[3,2-d]pyrimidine-7-carboxamide

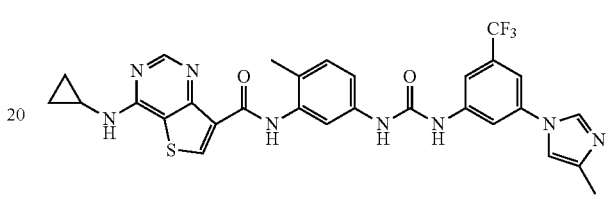

The procedure of Example 122 was repeated except for using the compound obtained in Step 2 of Example 82 instead of N-(5-amino-2-methylphenyl)-4-(cyclopropylamino)thieno[3,2-d]pyrimidine-7-carboxamide to obtain the title compound.

$^1$H NMR (300 MHz, DMSO-$d_6$) δ 11.76 (br, 2H), 9.06 (d, 1H), 8.94 (s, 1H), 8.64 (m, 2H), 8.51 (s, 1H), 8.40 (d, 1H), 8.21 (s, 1H), 7.94 (d, 1H), 7.53 (d, 1H), 7.32 (m, 2H), 7.19 (m, 1H), 3.04 (m, 1H), 2.37 (s, 3H), 2.18 (s, 3H), 0.85 (m, 2H), 0.69 (m, 2H).

The compound of Example 124 was prepared according to Reaction Scheme 17 below:

Reaction Scheme 17

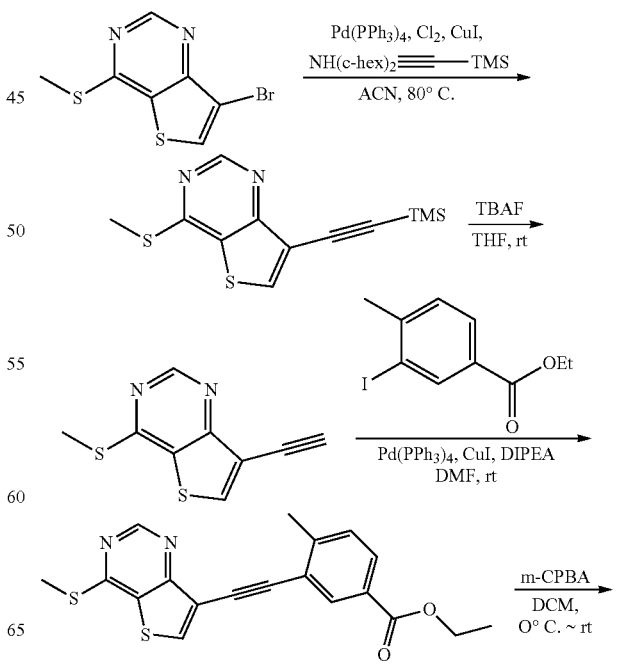

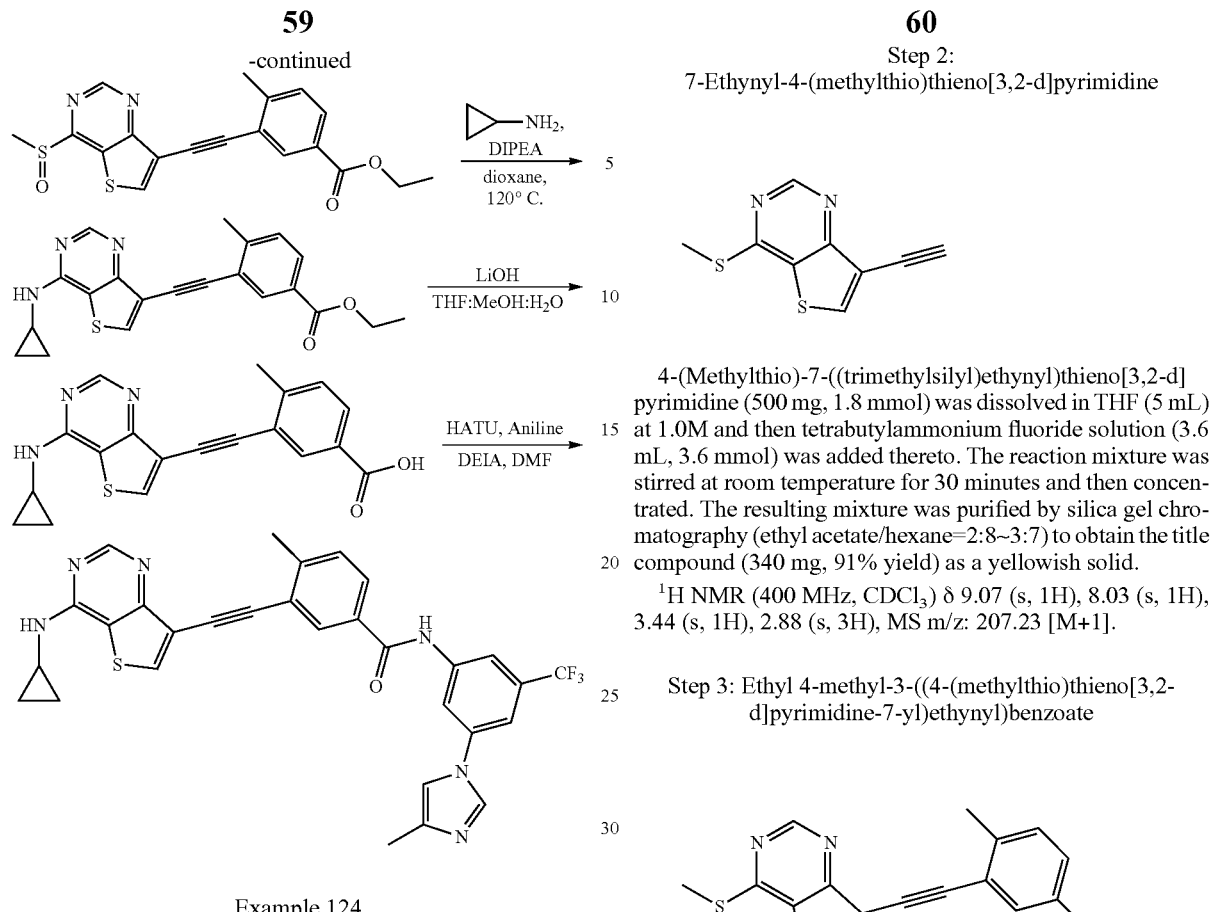

Example 124

3-((4-(Cyclopropylamino)thieno[3,2-d]pyrimidine-7-yl)ethynyl)-4-methyl-N-(3-(4-methyl-1H-imidazole-1-yl)-5-(trifluoromethyl)phenyl)benzamide Step 1: 4-(Methylthio)-7-((trimethylsilyl)ethynyl) thieno[3,2-d]pyrimidine 7-Bromo-4-(methylthio)thieno[3,2-d]pyrimidine (3 g, 11.49 mmol) was dissolved in acetonitrile (30 mL) and then bis(triphenylphosphine)palladium(II) dichloride (204 mg, 0.29 mmol), CuI (76 mg, 0.40 mmol), dicyclohexylamine (2.5 mL, 12.64 mmol) and ethynyltrimethylsilane (3.2 mL, 22.98 mmol) were added thereto. The reaction mixture was treated with $N_2$ gas for 15 minutes and stirred at 80° C. for 14 hours. The reaction mixture was cooled to room temperature, filtered using Celite and washed with ethyl acetate (50 mL). The filtrate was washed with brine and concentrated by drying with $MgSO_4$. The resulting mixture was purified by silica gel chromatography (ethyl acetate/hexane=1:9~2:8) to obtain the title compound (2.1 g, 65% yield) as a yellowish solid.

$^1$H NMR (400 MHz, $CDCl_3$) δ 9.05 (s, 1H), 7.99 (s, 1H), 2.74 (s, 3H), 0.30 (s, 9H),
MS m/z: 279.34 [M+1].

Step 2: 7-Ethynyl-4-(methylthio)thieno[3,2-d]pyrimidine 4-(Methylthio)-7-((trimethylsilyl)ethynyl)thieno[3,2-d] pyrimidine (500 mg, 1.8 mmol) was dissolved in THF (5 mL) at 1.0M and then tetrabutylammonium fluoride solution (3.6 mL, 3.6 mmol) was added thereto. The reaction mixture was stirred at room temperature for 30 minutes and then concentrated. The resulting mixture was purified by silica gel chromatography (ethyl acetate/hexane=2:8~3:7) to obtain the title compound (340 mg, 91% yield) as a yellowish solid.

$^1$H NMR (400 MHz, $CDCl_3$) δ 9.07 (s, 1H), 8.03 (s, 1H), 3.44 (s, 1H), 2.88 (s, 3H), MS m/z: 207.23 [M+1].

Step 3: Ethyl 4-methyl-3-((4-(methylthio)thieno[3,2-d]pyrimidine-7-yl)ethynyl)benzoate 7-Ethynyl-4-(methylthio)thieno[3,2-d]pyrimidine (850 mg, 4.12 mmol) was dissolved in DMF (9 mL) and then ethyl 3-iodo-4-methyl benzoate (902 mg, 4.12 mmol), $Pd(PPh_3)_4$ (242 mg, 0.21 mmol), CuI (59 mg, 0.31 mmol) and DIEA (1.0 mL, 6.18 mmol) were added thereto. The reaction mixture was stirred at room temperature for 16 hours and concentrated by filtering with Celite. The resulting mixture was purified by silica gel chromatography (ethyl acetate/hexane=1:9→2:8) to obtain the title compound (1.1 g, 72% yield) as a yellowish solid.

$^1$H NMR (400 MHz, $CDCl_3$) δ 9.11 (s, 1H), 8.75 (s, 1H), 8.07 (s, 1H), 7.90 (d, 1H), 7.52 (d, 1H), 4.33 (q, 2H), 2.78 (s, 3H), 2.61 (s, 3H), 1.34 (t, 3H), MS m/z: 369.44 [M+1].

Step 4: Ethyl 3-((4-(cyclopropylamino)thieno[3,2-d] pyrimidine-7-yl)ethynyl)-4-methyl benzoate Ethyl-4-methyl-3-((4-(methylthio)thieno[3,2-d]pyrimidine-7-yl)ethynyl)benzoate (440 mg, 1.19 mmol) was dissolved in methylene chloride (6 mL) and then m-CPBA (616 mg, 3.57 mmol) was added thereto at 0° C. The reaction mixture was stirred at 0° C. for 30 minutes and methylene chloride (20 mL) was added thereto. The reaction mixture was washed with a sat. aqueous NaHCO₃ solution (30 mL×3). The organic layer was dried with MgSO₄, filtered with Celite and concentrated to obtain the title compound without further purification.

¹H NMR (400 MHz, CDCl₃) δ 9.58 (s, 1H), 9.13 (s, 1H), 8.10 (s, 1H), 7.94 (d, 1H), 7.70 (d, 1H), 4.33 (q, 2H), 3.54 (s, 3H), 2.63 (s, 3H), 1.34 (t, 3H), MS m/z: 385.50 [M+1].

Step 5: Ethyl-3-((4-(cyclopropylamino)thieno[3,2-d]pyrimidine-7-yl)ethynyl)-4-methyl benzoate

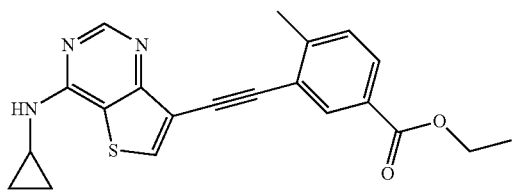 [SMILES: CCOC(=O)c1ccc(C)c(C#Cc2csc3c(NC4CC4)ncnc23)c1]

Ethyl-3-((4-(cyclopropylamino)thieno[3,2-d]pyrimidine-7-yl)ethynyl)-4-methyl benzoate (50 mg, 0.13 mmol) was dissolved in dioxane (1 mL) and then cyclopropylamine (37 mg, 0.65 mmol) and DIEA (0.1 mL, 0.65 mmol) were added thereto. The reaction mixture was stirred at 120° C. for 8 hours and cooled to room temperature. Ethyl acetate (5 mL) was added thereto and the reaction mixture was washed with brine. The organic layer was dried with MgSO₄, filtered with Celite and concentrated. The resulting mixture was purified by silica gel chromatography (ethyl acetate/hexane=2:8~4:6) to obtain the title compound (32 mg, 65% yield).

¹H NMR (400 MHz, DMSO-d₆) δ 8.52 (s, 1H), 8.47 (s, 1H), 8.09 (m, 1H), 8.03 (s, 1H), 7.89 (dd, 1H), 7.51 (d, 1H), 4.32 (q, 2H), 3.58 (m, 4H), 2.58 (s, 3H), 1.32 (t, 3H), MS m/z: 382.59 [M+1].

Step 6

3-((4-(Cyclopropylamino)thieno[3,2-d]pyrimidine-7-yl)ethynyl)-4-methylbenzoic acid

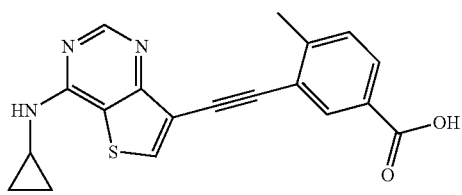 [SMILES: Cc1ccc(C(=O)O)cc1C#Cc1csc2c(NC3CC3)ncnc12]

The procedure of Step 4 of Example 1 was repeated except for using the compound obtained in Step 5 of Example 123 as a starting material to obtain the title compound.

MS m/z: 350.09 [M+1].

Step 7: 3-((4-(Cyclopropylamino)thieno[3,2-d]pyrimidine-7-yl)ethynyl)-4-methyl-N-(3-(4-methyl-1H-imidazole-1-yl)-5-(trifluoromethyl)phenyl)benzamide

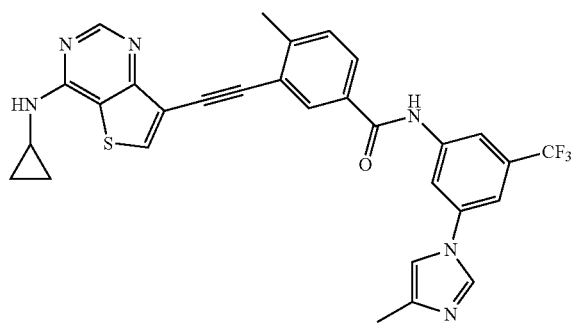 [SMILES: Cc1cn(-c2cc(NC(=O)c3ccc(C)c(C#Cc4csc5c(NC6CC6)ncnc45)c3)cc(C(F)(F)F)c2)cn1]

The procedure of Step 5 of Example 1 was repeated except for using the compound obtained in Step 6 in Example 124 as a starting material to obtain the title compound.

MS m/z: 573.17 [M+1].

Example 125

N-(3-((4-(cyclopropylamino)thieno[3,2-d]pyrimidine-7-yl)ethynyl)-4-methylphenyl)-3-(4-methyl-1H-imidazole-1-yl)-5-(trifluoromethyl)benzamide

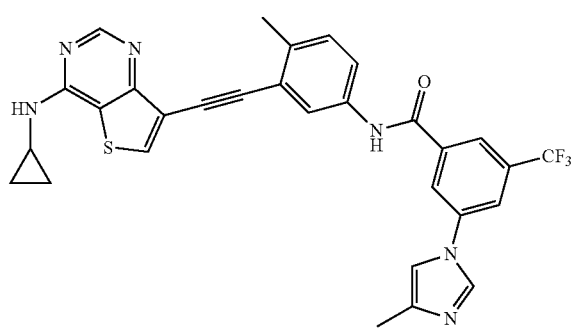 [SMILES: Cc1cn(-c2cc(C(=O)Nc3ccc(C)c(C#Cc4csc5c(NC6CC6)ncnc45)c3)cc(C(F)(F)F)c2)cn1]

The procedure of Step 3 of Example 124 was repeated except for using 2-iodo-1-methyl-4-nitrobenzene (TCI Laboratory Chemicals, Cat. #10706, CAS [7745-92-8]) instead of 3-iodo-4-methyl benzoate to obtain the product and then the procedure of Steps 1 to 3 of Example 4 was repeated using the product to obtain the title compound.

MS m/z: 573.19 [M+1].

Example 126

3-((4-(Cyclopropylamino)thieno[3,2-d]pyrimidine-7-yl)ethynyl)-4-methyl-N-(4-((4-methylpiperazine-1-yl)methyl)-3-(trifluoromethyl)phenyl)benzamide

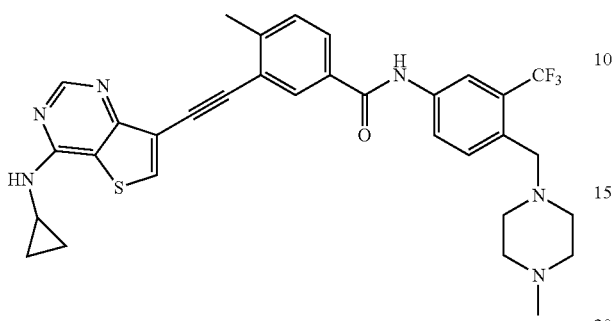

The procedure of Step 5 of Example 1 was repeated except for using 3-((4-(cyclopropylamino)thieno[3,2-d]pyrimidine-7-yl)ethynyl)-4-methylbenzoic acid obtained in Step 6 of Example 124 and (4-((4-methylpiperazine-1-yl)methyl)-3-(trifluoromethyl)aniline to obtain the title compound.
MS m/z: 605.15 [M+1].

Example 127

3-((4-(Cyclopropylamino)thieno[3,2-d]pyrimidine-7-yl)ethynyl)-N-(4-((4-ethylpiperazine-1-yl)methyl)-3-(trifluoromethyl)phenyl)-4-methylbenzamide

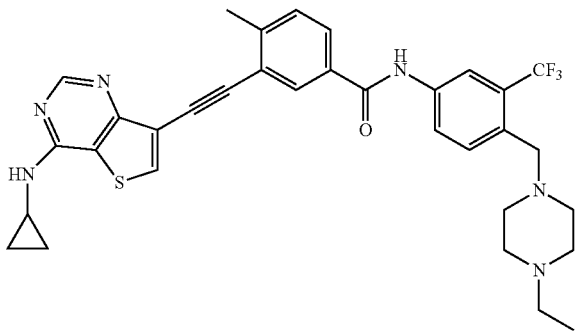 [SMILES: CCN1CCN(Cc2ccc(NC(=O)c3ccc(C)c(C#Cc4csc5c(NC6CC6)ncnc45)c3)cc2C(F)(F)F)CC1]

The procedure of Step 5 of Example 1 was repeated except for using 3-((4-(cyclopropylamino)thieno[3,2-d]pyrimidine-7-yl)ethynyl)-4-methylbenzoic acid obtained in Step 6 of Example 124 and (4-((4-ethylpiperazine-1-yl)methyl)-3-(trifluoromethyl)aniline to obtain the title compound.

$^1$H NMR (DMSO, 300 MHz) δ 10.54 (s, 1H), 8.54 (s, 1H), 8.48 (s, 1H), 8.19 (m, 3H), 8.05 (d, 1H), 7.91 (d, 1H), 7.70 (d, 1H), 7.51 (d, 1H), 3.55 (s, 2H), 2.98 (m, 1H), 2.59 (s, 3H), 2.38 (m, 10H), 0.97 (t, 3H), 0.80 (m, 2H), 0.64 (m, 2H).

Example 128

3-((4-(Cyclopropylamino)thieno[3,2-d]pyrimidine-7-yl)ethynyl)-4-methyl-N-(4-(1-methylpiperazine-1-yloxy)-3-(trifluoromethyl)phenyl)benzamide

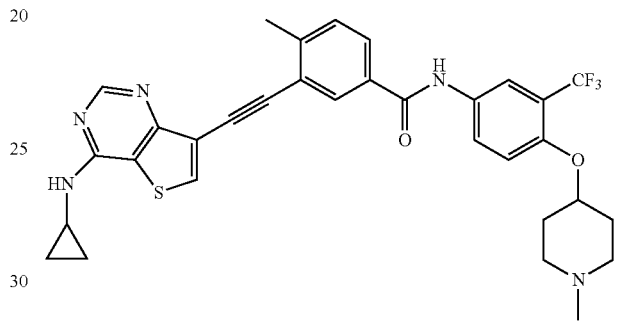

The procedure of Step 5 of Example 1 was repeated except for using 3-((4-(cyclopropylamino)thieno[3,2-d]pyrimidine-7-yl)ethynyl)-4-methylbenzoic acid obtained in Step 6 of Example 124 and 4-(1-methylpiperidine-4-yloxy)-3-(trifluoromethyl)aniline to obtain the title compound.

$^1$H NMR (DMSO, 300 MHz) δ 10.41 (s, 1H), 8.56 (s, 1H), 8.49 (s, 1H), 8.24 (d, 1H), 8.18 (d, 1H), 8.11 (d, 1H), 8.03 (d, 1H), 7.92 (d, 1H), 7.52 (d, 1H), 7.33 (d, 1H), 4.60 (m, 1H), 3.01 (m, 1H), 2.60 (s, 3H), 2.38 (m, 4H), 2.28 (s, 3H), 1.93 (m, 2H), 1.71 (m, 2H), 0.83 (m, 2H), 0.69 (m, 2H).

The structures, NMR and MS m/z data of the compounds obtained in Examples 1 to 128 are summarized in Table 1.

TABLE 1

| Example No. | Chemical name / Structure | NMR and/or MS m/z |
|---|---|---|
| 1 | (E)-3-(2-(4-aminothieno[3,2-d]pyrimidine-7-yl)vinyl)-4-methyl-N-(3-(trifluoromethyl)phenyl)benzamide | MS m/z [M + 1] 455.20. |

TABLE 1-continued

| Example No. | Structure / Chemical name | NMR and/or MS m/z |
|---|---|---|
| 2 | (E)-3-(2-(4-aminothieno[3,2-d]pyrimidine-7-yl)vinyl)-N-(4-((4-ethylpiperazine-1-yl)methyl)-3-(trifluoromethyl)phenyl)-4-methylbenzamide | MS m/z [M + 1] 567.21. |
| 3 | (E)-3-(2-(4-aminothieno[3,2-d]pyrimidine-7-yl)vinyl)-N-(3-(4-ethylpiperazine-1-yl)-5-(trifluoromethyl)phenyl)-4-methylbenzamide | MS m/z [M + 1] 567.21. |
| 4 | (E)-N-(3-(2-(4-aminothieno[3,2-d]pyrimidine-7-yl)vinyl)-4-methylphenyl)-3-(4-methyl-1H-imidazole-1-yl)-5-(trifluoromethyl)benzamide | $^1$H NMR (400 MHz, DMSO-$d_6$) δ 8.50 (s, 1H), 8.44 (d, 1H), 8.37 (s, 1H), 8.25 (d, 1H), 8.04 (d, 1H), 7.56 (d, 1H), 7.52 (d, 1H), 7.45 (s, 2H), 2.58 (s, 3H); MS m/z [M + 1] 313.25. |

TABLE 1-continued

| Example No. | Chemical name Structure | NMR and/or MS m/z |
|---|---|---|
| 5 | (E)-N-(3-(2-(4-aminothieno[3,2-d]pyrimidine-7-yl)vinyl)-4-methylphenyl)-4-(1-methylpiperidine-4-yloxy)-3-(trifluoromethyl)benzamide | MS m/z [M + 1] 568.21. |
| 6 | (E)-N-(3-(2-(4-aminothieno[3,2-d]pyrimidine-7-yl)vinyl)-4-methylphenyl)-3-(trifluoromethyl)benzamide | MS m/z [M + 1] 455.11. |
| 7 | (E)-N-(3-(2-(4-aminothieno[3,2-d]pyrimidine-7-yl)vinyl)-4-methylphenyl)-4-((4-ethylpiperazin-1-yl)methyl)-3-(trifluoromethyl)benzamide | MS m/z [M + 1] 581.23. |
| 8 | 4-amino-N-(2-methyl-5-(3-(trifluoromethyl)phenylcarbamoyl)phenyl)thieno[3,2-d]pyrimidine-7-carboxamide | $^1$H NMR (300 MHz, DMSO-$d_6$) δ 11.80 (s, 1H), 10.47 (s, 1H), 8.89 (s, 1H), 8.80 (d, 1H, J = 1.6 Hz), 8.52 (s, 1H), 8.20-8.17 (m, 1H), 8.00-7.97 (m, 2H), 7.95-8.95 (bs, 2H), 7.63-7.60 (m, 1H), 7.52 (t, 1H, J = 8.0 Hz), 7.40-7.36 (m, 2H), 2.51 (s, 3H). |

TABLE 1-continued

| Example No. | Structure / Chemical name | NMR and/or MS m/z |
|---|---|---|
| 9 | 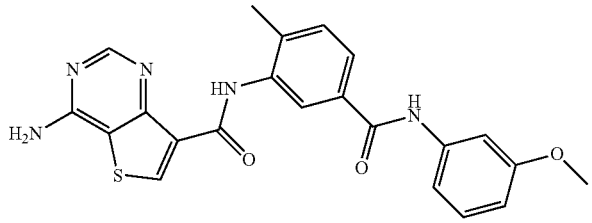 [SMILES: COc1cccc(NC(=O)c2ccc(C)c(NC(=O)c3csc4c(N)ncnc34)c2)c1]<br>4-amino-N-(5-(3-methoxyphenylcarbamoyl)-2-methylphenyl)thieno[3,2-d]pyrimidine-7-carboxamide | $^1$H NMR (300 MHz, DMSO-$d_6$) δ 11.80 (s, 1H), 10.12 (s, 1H), 8.89 (s, 1H), 8.76 (d, 1H, J = 1.6 Hz), 8.52 (s, 1H), 7.87 (bs, 2H), 7.59-7.56 (m, 1H), 7.40-7.29 (m, 3H), 7.16 (t, 1H, J = 8.1 Hz), 6.59 (dd, 1H, J = 8.1 Hz, 1.6 Hz), 3.68 (s, 3H) |
| 10 | 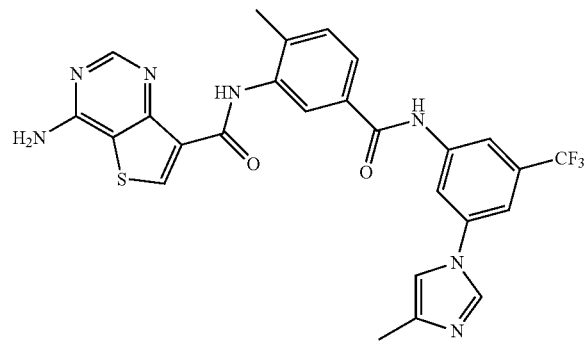 [SMILES: Cc1cn(-c2cc(NC(=O)c3ccc(C)c(NC(=O)c4csc5c(N)ncnc45)c3)cc(C(F)(F)F)c2)cn1]<br>4-amino-N-(2-methyl-5-(3-(4-methyl-1H-imidazole-1-yl)-5-(trifluoromethyl)phenylcarbamoyl)phenyl)thieno[3,2-d]pyrimidine-7-carboxamide | $^1$H NMR (400 MHz, DMSO-$d_6$) δ 11.89 (s, 1 H), 10.68 (s, 1 H), 8.96 (s, 1 H), 8.91 (br s, 1 H), 8.59 (s, 1 H), 8.31 (s, 1 H), 8.23 (s, 1 H), 8.15 (s, 1 H), 7.94 (br s, 2 H), 7.71 (m, 2 H), 7.49 (m, 2 H), 2.54 (s, 3 H), 2.18 (s, 3 H); MS m/z [M + 1] 552.38 |
| 11 | 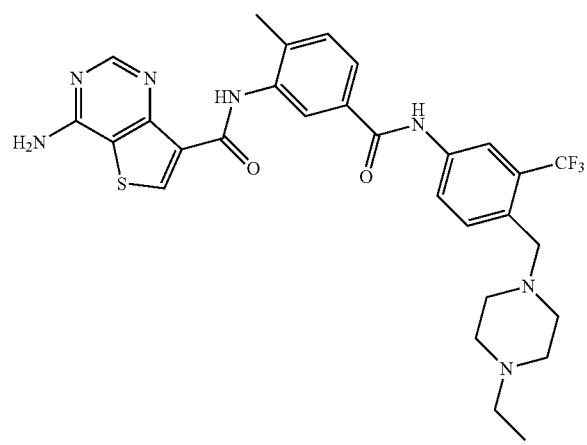 [SMILES: CCN1CCN(Cc2ccc(NC(=O)c3ccc(C)c(NC(=O)c4csc5c(N)ncnc45)c3)cc2C(F)(F)F)CC1]<br>4-amino-N-(5-(4-((4-ethylpiperazin-1-yl)methyl)-3-(trifluoromethyl)phenylcarbamoyl)-2-methylphenyl)thieno[3,2-d]pyrimidine-7-carboxamide | $^1$H NMR (400 MHz, DMSO-$d_6$) δ 11.88 (s, 1H), 10.50 (s, 1H), 8.97 (s, 1H), 8.88 (s, 1H), 8.60 (s, 1H), 8.21 (s, 1H), 8.07-8.05 (d, 1H), 7.95 (s, 2H), 7.72-7.69 (d, 2H), 7.48-7.46 (d, 1H), 3.57 (s, 2H), 2.61 (s, 3H), 2.40 (s, 8H), 2.34-2.27 (q, 2H), 1.00-0.96 (t, 3H) |
| 12 | 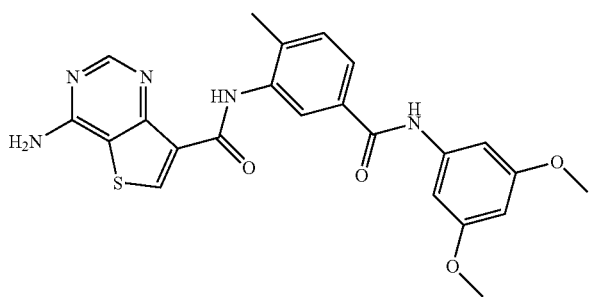 [SMILES: COc1cc(NC(=O)c2ccc(C)c(NC(=O)c3csc4c(N)ncnc34)c2)cc(OC)c1]<br>4-amino-N-(5-(3,5-dimethoxyphenylcarbamoyl)-2-methylphenyl)thieno[3,2-d]pyrimidine-7-carboxamide | $^1$H NMR (400 MHz, DMSO-$d_6$) δ 11.86 (s, 1H), 10.20 (s, 1H), 8.97 (s, 1H), 8.85-8.80 (m, 1H), 8.60 (s, 1H), 7.95 (br, 2H), 7.67-7.64 (m, 1H), 7.46-7.43 (m, 1H), 7.11-7.10 (m, 2H), 6.30-6.20 (m, 1H), 3.74 (s, 6H), 2.54 (s, 3H), |

TABLE 1-continued

| Example No. | Structure / Chemical name | NMR and/or MS m/z |
|---|---|---|
| 13 | 4-(4-methoxyphenylamino)-N-(2-methyl-5-(3-(trifluoromethyl)phenylcarbamoyl)phenyl)thieno[3,2-d]pyrimidine-7-carboxamide | $^1$H NMR (400 MHz, DMSO-$d_6$) δ 11.85 (s, 1H), 10.56 (s, 1H), 10.06 (s, 1H), 9.00 (s, 1H), 8.87 (s, 1H), 8.73 (s, 1H), 8.26 (s, 1H), 8.08 (d, 1H), 7.72 (d, 1H), 7.63-7.57 (m, 3H), 7.47 (d, 2H), 7.01 (d, 2H), 3.79 (s, 3H), 2.54 (s, 3H); MS m/z [M + 1] 578.07. |
| 14 | N-(2-methyl-5-(3-(trifluoromethyl)phenylcarbamoyl)phenyl)-4-(3,4,5-trimethoxyphenylamino)thieno[3,2-d]pyrimidine-7-carboxamide | $^1$H NMR (400 MHz, DMSO-$d_6$) δ 11.90 (s, 1H), 10.57 (s, 1H), 10.12 (s, 1H), 9.04 (s, 1H), 8.88 (s, 1H), 8.81 (s, 1H), 8.26 (s, 1H), 8.08 (d, 1H), 7.72 (d, 1H), 7.61 (t, 1H), 7.48 (dd, 2H), 7.15 (s, 2H), 3.80 (s, 6H), 3.69 (s, 3H), 2.56 (s, 3H); MS m/z [M + 1] 638.08 |
| 15 | N-(2-methyl-5-(3-(trifluoromethyl)phenylcarbamoyl)phenyl)-4-(6-methylpyridine-3-ylamino)thieno[3,2-d]pyrimidine-7-carboxamide | $^1$H NMR (400 MHz, DMSO-$d_6$) δ 11.74 (s, 1H), 10.52 (s, 1H), 10.45 (s, 1H), 9.12 (s, 1H), 8.98 (br s, 1H), 8.87 (d, 2H), 8.30-8.26 (m, 2H), 8.08 (d, 1H), 7.73 (d, 1H), 7.61 (t, 1H), 7.53-7.45 (m, 3H), 2.56 (br s, 6H); MS m/z [M + 1] 563.06 |

TABLE 1-continued

| Example No. | Structure | NMR and/or MS m/z |
|---|---|---|
| 16 | 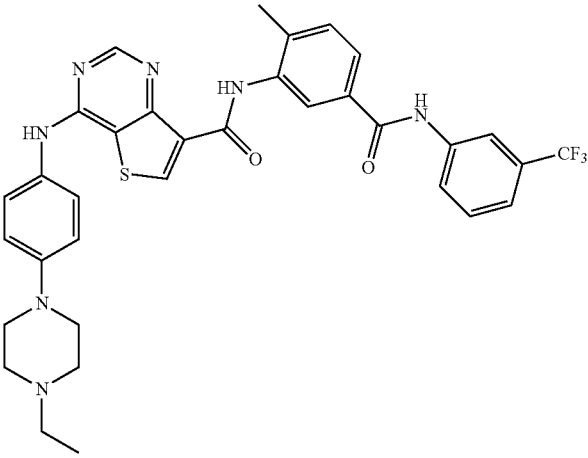 [SMILES: CCN1CCN(c2ccc(Nc3ncnc4c(C(=O)Nc5cc(C(=O)Nc6cccc(C(F)(F)F)c6)ccc5C)csc34)cc2)CC1]<br>4-(4-(4-ethylpiperazin-1-yl)phenylamino)-N-(2-methyl-5-(3-(trifluoromethyl)phenylcarbamoyl)phenyl)thieno[3,2-d]pyrimidine-7-carboxamide | $^1$H NMR (400 MHz, DMSO-$d_6$) δ 11.85 (s, 1H), 10.56 (s, 1H), 10.04 (s, 1H), 9.36 (s, 1H), 9.02 (s, 1H), 8.88 (s, 1H), 8.73 (s, 1H), 8.26 (s, 1H), 8.08 (d, 1H), 7.71 (d, 1H), 7.63-7.57 (m, 2H), 7.50-7.45 (m, 2H), 7.09 (d, 2H), 3.89 (d, 3H), 3.29-3.14 (m, 5H), 2.98 (q, 2H), 2.56 (s, 3H), 1.27 (t, 3H); MS m/z [M + 1] 660.21 |
| 17 | 4-(isopropylamino)-N-(2-methyl-5-(3-(trifluoromethyl)phenylcarbamoyl)phenyl)thieno[3,2-d]pyrimidine-7-carboxamide | $^1$H NMR (400 MHz, DMSO-$d_6$) δ 11.80 (s, 1H), 10.55 (s, 1H), 8.97 (s, 1H), 8.81 (br s, 1H), 8.66 (s, 1H), 8.26 (s, 1H), 8.08 (d, 1H), 7.72 (d, 1H), 7.60 (t, 1H), 7.47 (t, 2H), 4.56-4.48 (m, 1H), 2.53 (s, 1H), 1.27 (d, 6H); MS m/z [M + 1] 514.08 |
| 18 | N-(2-methyl-5-(3-(trifluoromethyl)phenylcarbamoyl)phenyl)-4-(methylamino)thieno[3,2-d]pyrimidine-7-carboxamide | $^1$H NMR (400 MHz, DMSO-$d_6$) δ 11.88 (s, 1H), 10.64 (s, 1H), 8.94 (s, 1H), 8.88 (s, 1H), 8.68 (s, 1H), 8.38-8.36 (m, 1H), 8.25 (s, 1H), 8.08 (d, 1H), 7.70 (d, 1H), 7.60 (t, 1H), 7.47 (t, 2H), 3.04 (d, 3H), 2.55 (s, 3H); MS m/z [M + 1] 486.01 |
| 19 | 4-(2-hydroxyethylamino)-N-(2-methyl-5-(3-(trifluoromethyl)phenylcarbamoyl)phenyl)thieno[3,2-d]pyrimidine-7-carboxamide | $^1$H NMR (400 MHz, DMSO-$d_6$) δ 11.89 (s, 1H), 10.56 (s, 1H), 8.95 (s, 1H), 8.86 (d, 1H), 8.66 (s, 1H), 8.51 (br s, 1H), 8.25 (s, 1H), 8.08 (s, 1H), 7.71 (d, 2H), 7.60 (t, 1H), 7.47 (t, 2H), 4.83 (s, 1H), 3.65-3.58 (m, 2H), 2.68-2.65 (m, 2H), 2.45 (s, 3H); MS m/z [M + 1] 516.07 |

TABLE 1-continued

| Example No. | Structure / Chemical name | NMR and/or MS m/z |
|---|---|---|
| 20 | 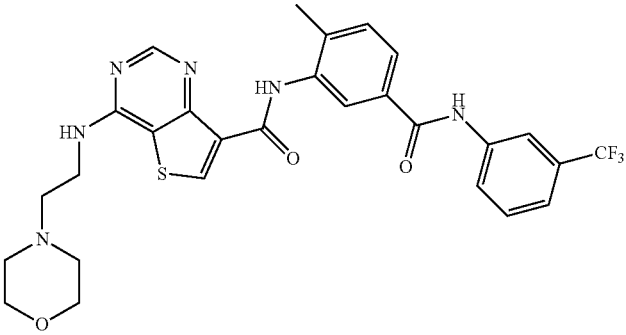 [SMILES: Cc1ccc(C(=O)Nc2cccc(C(F)(F)F)c2)cc1NC(=O)c1csc2c(NCCN3CCOCC3)ncnc12]<br>N-(2-methyl-5-(3-(trifluoromethyl)phenylcarbamoyl)phenyl)-4-(2-morpholinoethylamino)thieno[3,2-d]pyrimidine-7-carboxamide | $^1$H NMR (400 MHz, DMSO-d$_6$) δ 11.82 (s, 1H), 10.56 (s, 1H), 9.01 (s, 1H), 8.88 (s, 1H), 8.74 (s, 1H), 8.56 (br s, 1H), 8.07 (d, 1H), 7.73 (d, 1H), 7.61 (t, 1H), 7.47 (dd, 2H), 3.40 (s, 4H), 3.30 (s, 4H), 2.55-2.53 (m, 7H); MS m/z [M + 1] 585.12 |
| 21 | 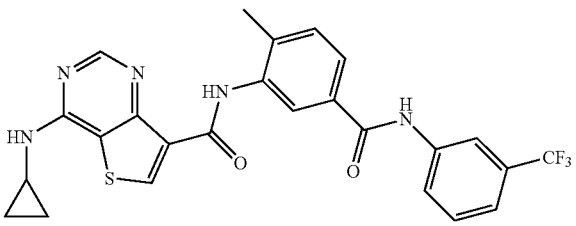 [SMILES: Cc1ccc(C(=O)Nc2cccc(C(F)(F)F)c2)cc1NC(=O)c1csc2c(NC3CC3)ncnc12]<br>4-(cyclopropylamino)-N-(2-methyl-5-(3-(trifluoromethyl)phenylcarbamoyl)phenyl)thieno[3,2-d]pyrimidine-7-carboxamide | MS m/z [M + 1] 512.06 |
| 22 | 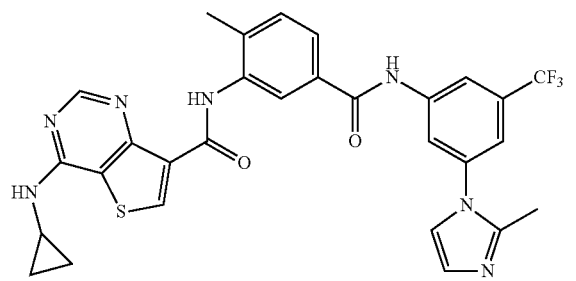 [SMILES: Cc1ccc(C(=O)Nc2cc(-n3ccnc3C)cc(C(F)(F)F)c2)cc1NC(=O)c1csc2c(NC3CC3)ncnc12]<br>4-(cyclopropylamino)-N-(2-methyl-5-(3-(2-methyl-1H-imidazole-1-yl)-5-(trifluoromethyl)phenylcarbamoyl)phenyl)thieno[3,2-d]pyrimidine-7-carboxamide | $^1$H-NMR (300 MHz, DMSO-d$_6$) δ 11.9 (s, 1H), 10.8 (s, 1H), 8.98 (s, 1H), 8.90 (s, 1H), 8.67 (s, 1H), 8.52 (s, 1H), 8.31 (s, 1H), 8.18 (s, 1H), 7.73 (d, 1H), 7.58 (s, 1H), 7.50 (d, 1H), 7.42 (s, 1H), 6.95 (s, 1H), 3.04 (m, 1H), 2.55 (s, 3H), 2.35 (s, 3H), 0.84 (m, 2H), 0.69 (m, 2H) |
| 23 | 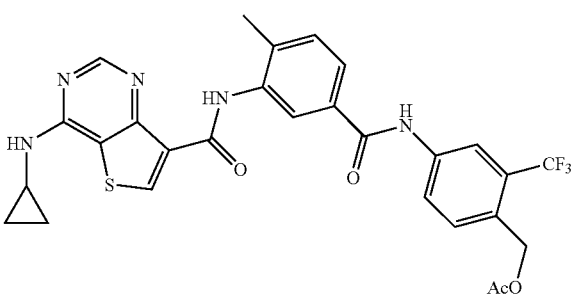<br>4-(3-(4-(cyclopropylamino)thieno[3,2-d]pyrimidine-7-carboxamido)-4-methylbenzamido)-2-(trifluoromethyl)benzyl acetate | $^1$H NMR (400 MHz, DMSO-d$_6$) δ 11.91 (s, 1H), 10.60 (s, 1H), 8.99 (br s, 1H), 8.89 (s, 1H), 8.69 (br s, 1H), 8.53 (br s, 1H), 8.29 (s, 1H), 8.12 (d, 1H), 7.71 (d, 1H), 7.65 (d, 1H), 7.18 (d, 1H), 5.19 (s, 2H), 3.06-3.04 (m, 1H), 2.89 (s, 3H), 2.08 (s, 3H), 0.85-0.80 (m, 2H), 0.70-0.64 (m, 2H); MS m/z [M + 1] 584.04. |

TABLE 1-continued

| Example No. | Structure / Chemical name | NMR and/or MS m/z |
|---|---|---|
| 24 | 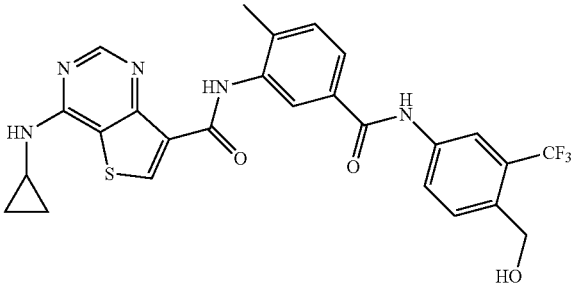 [SMILES: Cc1ccc(C(=O)Nc2ccc(CO)c(C(F)(F)F)c2)cc1NC(=O)c1csc2c(NC3CC3)ncnc12]<br>4-(cyclopropylamino)-N-(5-(4-(hydroxymethyl)-3-(trifluoromethyl)phenylcarbamoyl)-2-methylphenyl)thieno[3,2-d]pyrimidine-7-carboxamide | $^1$H NMR (400 MHz, DMSO-$d_6$) δ 11.91 (s, 1H), 10.50 (s, 1H), 8.99 (br s, 1H), 8.88 (s, 1H), 8.68 (br s, 1H), 8.52 (br s, 1H), 8.20 (s, 1H), 8.08 (d, 1H), 7.72 (dd, 2H), 7.47 (d, 1H), 5.44 (br s, 1H), 4.64 (d, 2H), 3.09-3.05 (m, 1H), 2.70 (s, 3H), 0.92-0.80 (m, 2H), 0.76-0.65 (m, 2H); MS m/z [M + 1] 541.96. |
| 25 | 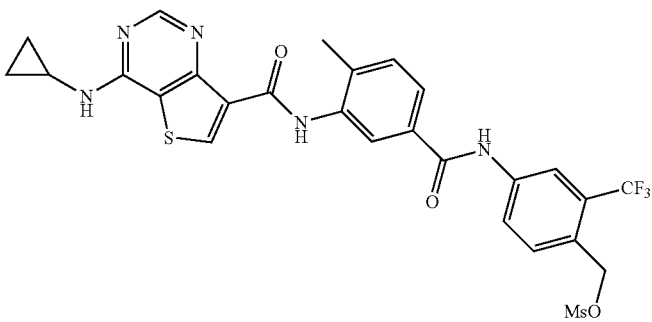 [SMILES: Cc1ccc(C(=O)Nc2ccc(COS(C)(=O)=O)c(C(F)(F)F)c2)cc1NC(=O)c1csc2c(NC3CC3)ncnc12]<br>4-(3-(4-(cyclopropylamino)thieno[3,2-d]pyrimidine-7-carboxamido)-4-methylbenzamido)-2-(trifluoromethyl)benzyl methanesulfonate | $^1$H NMR (400 MHz, DMSO-$d_6$) δ 11.92 (s, 1H), 10.63 (s, 1H), 8.99 (br s, 1H), 8.89 (s, 1H), 8.68 (br s, 1H), 8.52 (br s, 1H), 8.28 (s, 1H), 8.14 (d, 1H), 7.72 (dd, 2H), 7.49 (d, 1H), 4.86 (s, 2H), 3.12-3.05 (m, 1H), 2.67 (s, 3H), 1.20 (s, 3H), 0.92-0.87 (m, 2H), 0.74-0.60 (m, 2H); MS m/z [M + 1] 619.98 |
| 26 | 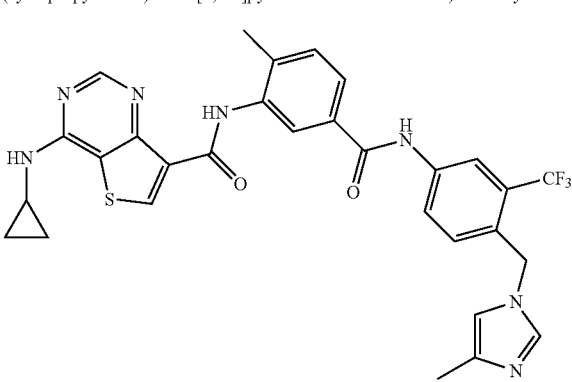<br>4-(cyclopropylamino)-N-(2-methyl-5-(4-((4-methyl-1H-imidazole-1-yl)methyl)-3-(trifluoromethyl)phenylcarbamoyl)phenyl)thieno[3,2-d]pyrimidine-7-carboxamide | $^1$H NMR (400 MHz, DMSO-$d_6$) δ 11.94 (s, 1H), 10.74 (s, 1H), 8.99 (br s, 1H), 8.93 (s, 1H), 8.68 (br s, 1H), 8.53 (br s, 1H), 8.41 (s, 1H), 8.21 (s, 1H), 7.82 (s, 1H), 7.74 (d, 2H), 7.51 (d, 1H), 4.47 (s, 2H), 3.09-3.02 (m, 1H), 2.24 (s, 3H), 1.17-1.00 (m, 2H), 0.85-0.78 (m, 2H). |
| 27 | 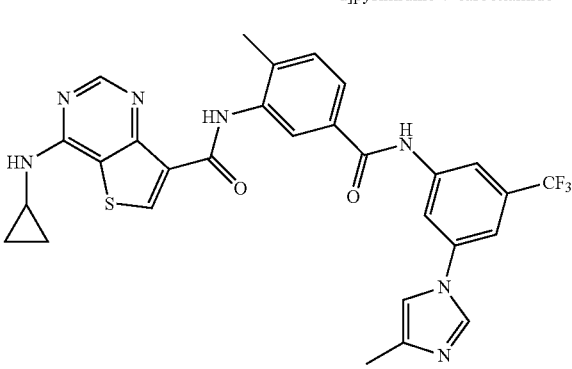<br>4-(cyclopropylamino)-N-(2-methyl-5-(3-(4-methyl-1H-imidazole-1-yl)-5-(trifluoromethyl)phenylcarbamoyl)phenyl)thieno[3,2-d]pyrimidine-7-carboxamide | $^1$H NMR (300 MHz, DMSO-$d_6$) δ 11.90 (s, 1 H), 10.67 (s, 1 H), 8.97 (s, 1 H), 8.90 (s, 1 H), 8.66 (s, 1 H), 8.51 (s, 1 H), 8.30 (s, 1 H), 8.19 (s, 1 H), 8.16 (s, 1 H), 7.71 (m, 2 H), 7.49 (m, 2 H), 3.12 (m, 1 H), 2.55 (s, 3 H), 2.17 (s, 3 H), 0.84 (m, 2 H), 0.69 (m, 2 H). |

TABLE 1-continued

| Example No. | Structure / Chemical name | NMR and/or MS m/z |
|---|---|---|
| 28 | N-(5-(3-bromo-5-(trifluoromethylcarbamoyl)phenyl)-2-methylphenyl)-4-(cyclopropylamino)thieno[3,2-d]pyrimidine-7-carboxamide | MS m/z [M + 1] 589.69, 591.67 |
| 29 | 4-(cyclopropylamino)-N-(2-methyl-5-(6-morpholinopyridine-3-ylcarbamoyl)phenyl)thieno[3,2-d]pyrimidine-7-carboxamide | MS m/z [M + 1] 530.14 |
| 30 | 4-(cyclopropylamino)-N-(5-(6-(4-ethylpiperazine-1-yl)pyridine-3-ylcarbamoyl)-2-methylphenyl)thieno[3,2-d]pyrimidine-7-carboxamide | MS m/z [M + 1] 557.12 |
| 31 | 4-(cyclopropylamino)-N-(5-(3-(2,4-dimethyl-1H-imidazole-1-yl)-5-(trifluoromethyl)phenylcarbamoyl)-2-methylphenyl)thieno[3,2-d]pyrimidine-7-carboxamide | $^1$H NMR (300 MHz, DMSO-$d_6$) δ 11.9 (s, 1H), 10.7 (s, 1H), 8.98 (s, 1H), 8.90 (s, 1H), 8.67 (s, 1H), 8.52 (s, 1H), 8.26 (s, 1H), 8.15 (s, 1H), 7.71 (d, 1H), 7.50 (d, 2H), 7.10 (s, 1H), 3.05 (m, 1H), 2.55 (s, 3H), 2.31 (s, 3H), 2.10 (s, 3H), 0.84 (m, 2H), 0.69 (m, 2H) |

TABLE 1-continued

| Example No. | Structure / Chemical name | NMR and/or MS m/z |
|---|---|---|
| 32 | 4-(cyclopropylamino)-N-(2-methyl-5-(4-((4-methyl-1,4-diazepan-1-yl)methyl)-3-(trifluoromethyl)phenylcarbamoyl)phenyl)thieno[3,2-d]pyrimidine-7-carboxamide | MS m/z [M + 1] 638.1 |
| 33 | (S)-4-(cyclopropylamino)-N-(5-(4-((3-(dimethylamino)pyrrolidine-1-yl)methyl)-3-(trifluoromethyl)phenylcarbamoyl)-2-methylphenyl)thieno[3,2-d]pyrimidine-7-carboxamide | MS m/z [M + 1] 638.11 |
| 34 | 4-(cyclopropylamino)-N-(5-(3-(4-hydroxymethyl)-1H-imidazole-1-yl)-5-(trifluoromethyl)phenylcarbamoyl)-2-methylphenyl)thieno[3,2-d]pyrimidine-7-carboxamide | $^{1}$H NMR (300 MHz, DMSO-$d_6$) δ 11.9 (s, 1H), 10.7 (s, 1H), 8.98 (s, 1H), 8.90 (s, 1H), 8.67 (s, 1H), 8.52 (s, 1H), 8.26 (s, 1H), 8.15 (s, 1H), 7.71 (d, 1H), 7.50 (d, 2H), 7.10 (s, 1H), 3.05 (m, 1H), 2.55 (s, 3H), 2.31 (s, 3H), 2.10 (s, 3H), 0.84 (m, 2H), 0.69 (m, 2H) |

| Example No. | Structure | NMR and/or MS m/z |
|---|---|---|
| 35 | 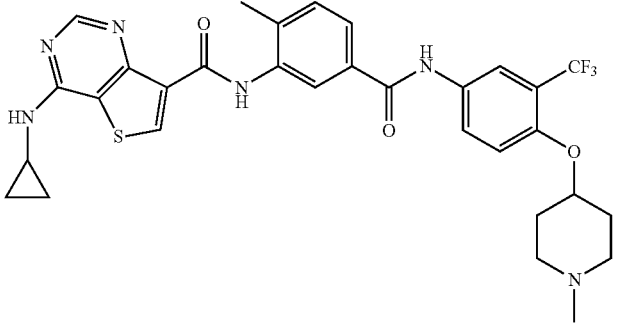 [SMILES: Cc1ccc(C(=O)Nc2ccc(OC3CCN(C)CC3)c(C(F)(F)F)c2)cc1NC(=O)c1csc2c(NC3CC3)ncnc12] 4-(cyclopropylamino)-N-(2-methyl-5-(4-(1-methylpiperidine-4-yloxy)-3-(trifluoromethyl)phenylcarbamoyl)phenyl)thieno[3,2-d]pyrimidine-7-carboxamide | $^1$H NMR (300 MHz, DMSO-$d_6$) δ 11.88 (s, 1H), 10.32 (s, 1H), 8.96 (s, 1H), 8.84 (s, 1H), 8.66 (s, 1H), 8.51 (s, 1H), 8.08 (s, 1H), 7.96 (d, 1H), 7.67 (d, 1H), 7.44 (d, 1H), 7.30 (d, 1H), 4.56 (m, 1H), 3.04 (m, 1H), 2.52 (s, 3H), 2.24 (m, 4H), 2.19 (s, 3H), 1.93 (m, 2H), 1.66 (m, 2H), 0.84 (m, 2H), 0.69 (m, 2H). |
| 36 | 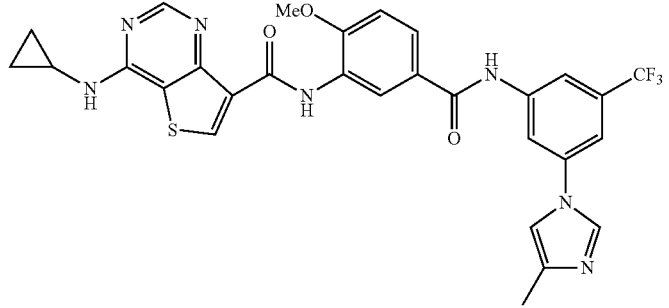 [SMILES: COc1ccc(C(=O)Nc2cc(-n3cnc(C)c3)cc(C(F)(F)F)c2)cc1NC(=O)c1csc2c(NC3CC3)ncnc12] 4-(cyclopropylamino)-N-(2-methoxy-5-(3-(4-methyl-1H-imidazole-1-yl)-5-(trifluoromethyl)phenylcarbamoyl)phenyl)thieno[3,2-d]pyrimidine-7-carboxamide | $^1$H NMR (300 MHz, DMSO-$d_6$) δ 12.45 (br, 1H), 10.67 (br, 1H), 9.17 (m, 1H), 9.00 (s, 1H), 8.75 (s, 1H), 8.51 (s, 1H), 8.35 (s, 1H), 8.25 (s, 1H), 8.20 (s, 1H), 7.86 (dd, 1H), 7.75 (s, 1H), 7.54 (s, 1H), 7.32 (d, 1H), 4.16 (s, 3H), 3.08 (m, 1H), 2.22 (s, 3H), 0.89 (m, 2H), 0.74 (m, 2H). |
| 37 | 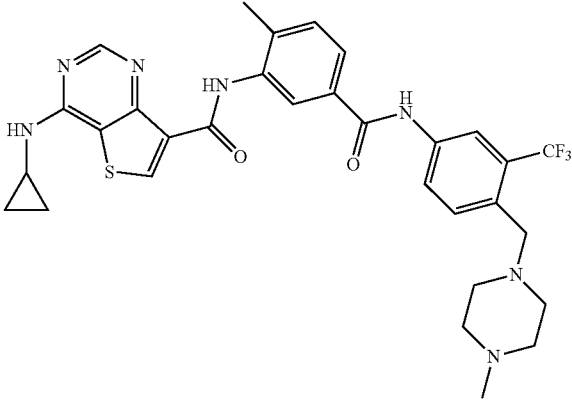 [SMILES: Cc1ccc(C(=O)Nc2ccc(CN3CCN(C)CC3)c(C(F)(F)F)c2)cc1NC(=O)c1csc2c(NC3CC3)ncnc12] 4-(cyclopropylamino)-N-(2-methyl-5-(4-((4-methylpiperazine-1-yl)methyl)-3-(trifluoromethyl)phenylcarbamoyl)phenyl)thieno[3,2-d]pyrimidine-7-carboxamide | $^1$H NMR (300 MHz, DMSO-$d_6$) δ 11.90 (s, 1H), 10.50 (s, 1H), 8.98 (s, 1H), 8.88 (d, 1H), 8.68 (s, 1H), 8.51 (s, 1H), 8.22 (d, 1H), 8.06 (d, 1H), 7.72 (s, 1H), 7.69 (s, 1H), 7.47 (d, 1H), 3.57 (s, 2H), 3.05 (m, 1H), 2.55 (s, 3H), 2.36 (br, 8H), 2.21 (s, 3H), 0.86 (m, 2H), 0.70 (m, 2H). |

TABLE 1-continued

| Example No. | Chemical name / Structure | NMR and/or MS m/z |
|---|---|---|
| 38 | 4-(cyclopropylamino)-N-(5-(4-((4-ethylpiperazin-1-yl)methyl)-3-(trifluoromethyl)phenylcarbamoyl)-2-methylphenyl)thieno[3,2-d]pyrimidine-7-carboxamide | $^1$H NMR (300 MHz, DMSO-$d_6$) δ 11.88 (s, 1H), 10.49 (s, 1H), 9.05 (s, 1H), 8.95 (d, 1H), 8.86 (s, 1H), 8.76 (s, 1H), 8.20 (d, 1H), 8.12 (d, 1H), 7.70 (s, 1H), 7.68 (s, 1H), 7.47 (d, 1H), 3.55 (s, 2H), 3.04 (m, 1H), 2.53 (s, 5H), 2.39 (br, 8H), 0.97 (t, 3H), 0.86 (m, 2H), 0.70 (m, 2H). |
| 39 | 4-amino-N-(2-methyl-5-(3-(trifluoromethyl)benzamido)phenyl)thieno[3,2-d]pyrimidine-7-carboxamide | $^1$H NMR (300 MHz, DMSO-$d_6$) δ 11.74 (s, 1 H), 10.51 (s, 1 H), 8.92 (s, 1 H), 8.67 (s, 1 H), 8.58 (s, 1 H), 8.31 (s, 1 H), 8.28 (d, 1 H), 7.96 (d, 1 H), 7.94 (s, 2 H), 7.77 (t, 1 H), 7.58 (d, 1 H), 7.27 (d, 1 H), 2.44 (s, 3 H). |
| 40 | 4-(cyclopropylamino)-N-(2-methyl-5-(4-morpholino-3-(trifluoromethyl)benzamido)phenyl)thieno[3,2-d]pyrimidine-7-carboxamide | $^1$H NMR (300 MHz, DMSO-$d_6$) δ 11.8 (s, 1H), 10.4 (s, 1H), 8.95 (s, 1H), 8.66 (d, 2H), 8.50 (s, 1H), 8.26 (d, 2H), 7.65 (d, 1H), 7.50 (d, 1H), 7.27 (d, 1H), 3.74 (m, 4H), 3.03 (m, 1H), 2.98 (m, 4H), 2.48 (s, 3H), 0.85 (m, 2H), 0.68 (m, 2H). |

TABLE 1-continued

| Example No. | Structure / Chemical name | NMR and/or MS m/z |
|---|---|---|
| 41 | 4-(cyclopropylamino)-N-(5-(3-(3-(dimethylamino)propylamino)-5-(trifluoromethyl)benzamido)-2-methylphenyl)thieno[3,2-d]pyrimidine-7-carboxamide | ¹H NMR (300 MHz, DMSO-d₆) δ 11.74 (s, 1H), 10.31 (s, 1H), 8.90 (s, 1H), 8.62 (m, 2H), 8.48 (s, 1H), 7.52 (d, 1H), 7.37 (s, 1H), 7.32 (s, 1H), 7.23 (d, 1H), 6.98 (s, 1H), 6.38 (s, 1H), 3.12 (m, 2H), 3.03 (m, 1H), 2.42 (s, 3H), 2.29 (m, 2H), 2.12 (3, 6H), 1.69 (m, 2H), 0.84 (m, 2H), 0.68 (m, 2H). |
| 42 | 4-amino-N-(5-benzamido-2-methylphenyl)thieno[3,2-d]pyrimidine-7-carboxamide | ¹H NMR (300 MHz, DMSO-d₆) δ 11.75 (s, 1 H), 10.21 (s, 1 H), 8.95 (s, 1 H), 8.70 (s, 1 H), 8.58 (s, 1 H), 8.03 (m, 4 H), 7.65 (m, 4 H), 7.24 (d, 1 H), 2.43 (s, 3 H); MS m/z [M + 1] 403.96 |
| 43 | 4-amino-N-(5-(3,5-dimethoxybenzamido)-2-methylphenyl)thieno[3,2-d]pyrimidine-7-carboxamide | ¹H NMR (300 MHz, DMSO-d₆) δ 11.72 (s, 1 H), 10.20 (s, 1 H), 8.92 (s, 1 H), 8.65 (s, 1 H), 8.59 (s, 1 H), 7 92 (br s, 2 H), 7.55 (d, 1 H), 7.25 (d, 1 H), 7.14 (br s, 2 H), 6.70 (s, 1 H), 3.83 (s, 6 H), 2.44 (s, 3 H) |
| 44 | N-(5-benzamido-2-methylphenyl)-4-(5-methylpyridin-2-ylamino)thieno[3,2-d]pyrimidine-7-carboxamide | ¹H NMR (300 MHz, DMSO-d₆) δ 11.75 (s, 1 H), 10.83 (s, 1 H), 10.30 (s, 1 H), 9.04 (s, 1 H), 8.85 (s, 1 H), 8.68 (s, 1 H), 8.25 (d, 1 H), 7.98 (d, 2 H), 7.90 (m, 1 H), 7.75 (m, 1 H), 7.56 (m, 4 H), 7.31 (m, 2 H), 2.46 (s, 3 H), 2.31 (s, 3 H); MS m/z [M + 1] 516.91 |

TABLE 1-continued

| Example No. | Structure / Chemical name | NMR and/or MS m/z |
|---|---|---|
| 45 | 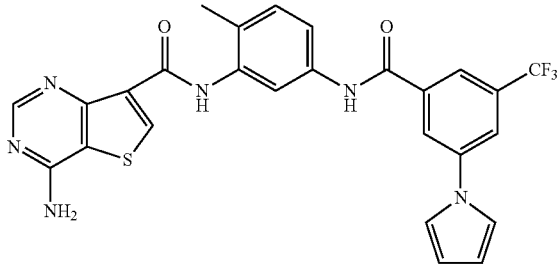 [SMILES: Cc1ccc(NC(=O)c2cc(-n3cccc3)cc(C(F)(F)F)c2)cc1NC(=O)c1csc2c(N)ncnc12]<br>N-(5-(3-(1H-pyrrol-1-yl)-5-(trifluoromethyl)benzamido)-2-methylphenyl)-4-aminothieno[3,2-d]pyrimidine-7-carboxamide | $^1$H NMR (300 MHz, DMSO-$d_6$) δ 11.75 (s, 1 H), 10.54 (s, 1 H), 8.92 (s, 1 H), 8.67 (s, 1 H), 8.56 (s, 1 H), 8.42 (s, 1 H), 8.14 (s, 1 H), 8.09 (s, 1 H), 7.95 (s, 2 H), 7.64 (m, 2 H), 7.60 (d, 1 H), 7.29 (d, 1 H), 6.36 (m, 2 H), 2.45 (s, 3 H) |
| 46 | 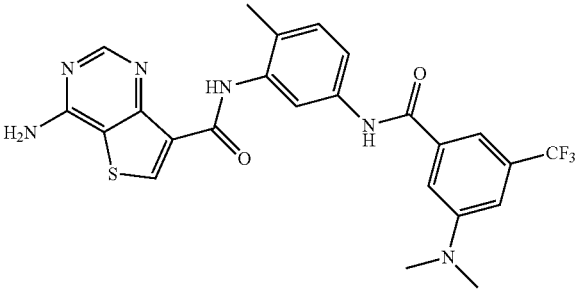 [SMILES: Cc1ccc(NC(=O)c2cc(N(C)C)cc(C(F)(F)F)c2)cc1NC(=O)c1csc2c(N)ncnc12]<br>4-amino-N-(5-(3-(dimethylamino)-5-(trifluoromethyl)benzamido)-2-methylphenyl)thieno[3,2-d]pyrimidine-7-carboxamide | $^1$H NMR (300 MHz, DMSO-$d_6$) δ 11.71 (s, 1 H), 10.40 (s, 1 H), 8.90 (s, 1 H), 8.86-8.62 (m, 2 H), 8.07-7.78 (m, 2 H), 7.63-7.48 (m, 3 H), 7.30-7.20 (m, 1 H), 7.13-7.05 (m, 1 H), 3.00 (s, 6 H), 2.43 (s, 3 H) |
| 47 | 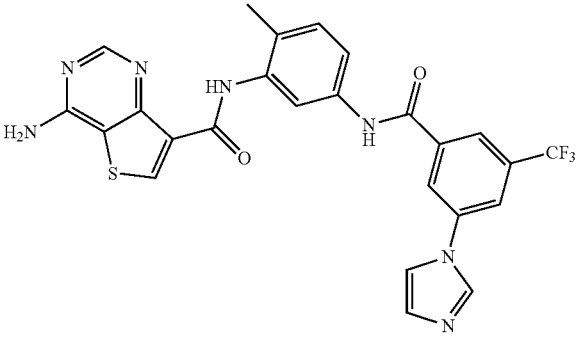 [SMILES: Cc1ccc(NC(=O)c2cc(-n3ccnc3)cc(C(F)(F)F)c2)cc1NC(=O)c1csc2c(N)ncnc12]<br>N-(5-(3-(1H-imidazol-1-yl)-5-(trifluoromethyl)benzamido)-2-methylphenyl)-4-aminothieno[3,2-d]pyrimidine-7-carboxamide | $^1$H NMR (300 MHz, DMSO-$d_6$) δ 11.78 (s, 1H), 10.70 (s, 1H), 8.94 (s, 1H), 8.75-8.65 (m, 1H), 8.59-8.53 (m, 2H), 8.35-8.25 (m, 1H), 8.25-8.15 (m, 1H), 8.10-8.07 (m, 1H), 8.01-7.90 (m, 2H), 7.63-7.59 (m, 1H), 7.32-7.29 (m, 1H), 7.19-7.15 (m, 1H), 2.47 (s, 3H) |
| 48 | 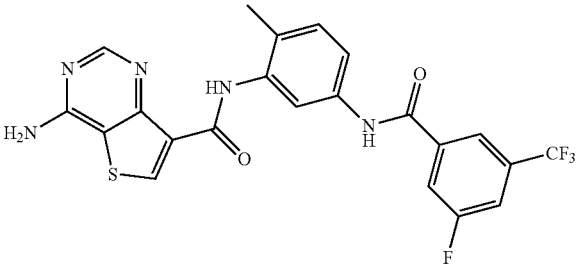 [SMILES: Cc1ccc(NC(=O)c2cc(F)cc(C(F)(F)F)c2)cc1NC(=O)c1csc2c(N)ncnc12]<br>4-amino-N-(5-(3-fluoro-5-(trifluoromethyl)benzamido)-2-methylphenyl)thieno[3,2-d]pyrimidine-7-carboxamide | $^1$H NMR (300 MHz, DMSO-$d_6$) δ 11.76 (s, 1 H), 10.55 (s, 1 H), 8.93 (s, 1 H), 8.68 (s, 1 H), 8.59 (s, 1 H), 8.31 (s, 2 H), 8.20 (s, 1 H), 8.15 (d, 1 H), 7.94 (m, 2 H), 7.60 (d, 1 H), 7.39 (d, 1 H), 2.46 (s, 3 H); MS m/z [M + 1] 489.95 |

TABLE 1-continued

| Example No. | Structure / Chemical name | NMR and/or MS m/z |
|---|---|---|
| 49 | 4-amino-N-(5-(4-((4-ethylpiperazine-1-yl)methyl)-3-(trifluoromethyl)benzamido)-2-methylphenyl)thieno[3,2-d]pyrimidine-7-carboxamide | $^1$H NMR (300 MHz, DMSO-$d_6$) δ 11.74 (s, 1 H), 10.49 (s, 1 H), 8.92 (s, 1 H), 8.67 (s, 1 H), 8.58 (s, 1 H), 8.27 (m, 2 H), 7.95 (m, 3 H), 7.59 (d, 1 H), 7.27 (d, 1 H), 3.68 (s, 2 H), 2.45-2.27 (m, 10 H), 0.98 (m, 3 H); MS m/z [M + 1] 597.92 |
| 50 | 1-(4-(3-(4-aminothieno[3,2-d]pyrimidine-7-carboxyamido)-4-methylphenylcarbamoyl)-2-(trifluoromethyl)benzyl)piperidine-4-yl acetate | $^1$H NMR (300 MHz, DMSO-$d_6$) δ 11.78 (s, 1 H), 10.49 (s, 1 H), 8.93 (s, 1 H), 8.66 (d, 1 H), 8.59 (s, 1 H), 8.31 (s, 1 H), 8.23 (m, 2 H), 7.93 (m, 2 H), 7.59 (d, 1 H), 7.27 (d, 1 H), 4.58 (d, 1 H), 4.05 (m, 1 H), 2.69 (m, 4 H), 1.25 (m, 4 H) |
| 51 | N-(2-methyl-5-(3-(trifluoromethyl)benzamido)phenyl)-4-(phenylamino)thieno[3,2-d]pyrimidine-7-carboxamide | $^1$H NMR (300 MHz, DMSO-$d_6$) δ 11.69 (s, 1 H), 10.51 (s, 1 H), 10.14 (s, 1 H), 9.00 (s, 1 H), 8.76 (s, 1 H), 8.68 (d, 1 H), 8.31 (s, 1 H), 8.28 (d, 1 H), 7.96 (d, 1 H), 7.80-7.73 (m, 3 H), 7.68 (d, 1 H), 7.41 (m, 2 H), 7.28 (d, 1 H), 7.17 (t, 1 H), 2.46 (s, 3 H); 548 |
| 52 | N-(2-methyl-5-(3-(trifluoromethyl)benzamido)phenyl)-4-(pyridine-4-ylamino)thieno[3,2-d]pyrimidine-7-carboxamide | MS m/z [M + 1] 571 |

TABLE 1-continued

| Example No. | Structure / Chemical name | NMR and/or MS m/z |
|---|---|---|
| 53 | N-(2-methyl-5-(3-(trifluoromethyl)benzamido)phenyl)-4-(pyridine-2-ylamino)thieno[3,2-d]pyrimidine-7-carboxamide | $^1$H NMR (300 MHz, DMSO-$d_6$) δ 11.19 (s, 1 H), 10.50 (s, 1 H), 8.93 (s, 1 H), 8.62 (s, 1 H), 8.50 (s, 1 H), 8.30 (s, 1 H), 8.27 (d, 1 H), 7.95 (d, 1 H), 7.87 (d, 1 H), 7.77 (t, 1 H), 7.59 (dd, 1 H), 7.31 (m, 3 H), 6.43 (m, 2 H), 2.40 (s, 3 H); MS m/z [M + 1] 549.77 |
| 54 | 4-amino-N-(5-isoquinoline-1-carboxyamido)-2-methylphenyl)thieno[3,2-d]pyrimidine-7-carboxamide | $^1$H NMR (300 MHz, DMSO-$d_6$) δ 11.75 (s, 1 H), 10.78 (s, 1 H), 8.93 (s, 1 H), 8.81 (br d, 2 H), 8.62 (d, 1 H), 8.58 (s, 1 H), 8.08 (d, 1 H), 8.06 (d, 1 H), 7.92 (s, 1 H), 7.85 (t, 1 H), 7.76 (t, 1 H), 7.62 (dd, 1 H), 7.29 (d, 1 H), 2.45 (s, 3 H) |
| 55 | 4-amino-N-(5-(isoquinoline-3-carboxyamido)-2-methylphenyl)thieno[3,2-d]pyrimidine-7-carboxamide | $^1$H NMR (300 MHz, DMSO-$d_6$) δ 11.74 (s, 1 H), 10.67 (s, 1 H), 9.47 (s, 1 H), 8.94 (s, 1 H), 8.80 (s, 1 H), 8.68 (s, 1 H), 8.58 (s, 1 H), 8.30 (d, 1 H), 8.25 (d, 1 H), 7.93-7.81 (m, 5 H), 7.66 (d, 1 H), 7.28 (d, 1 H), 2.44 (s, 3 H) |
| 56 | 4-amino-N-(5-(4-methoxyquinoline-2-carboxyamido)-2-methylphenyl)thieno[3,2-d]pyrimidine-7-carboxamide | $^1$H NMR (300 MHz, DMSO-$d_6$) δ 11.76 (s, 1 H), 10.65 (s, 1 H), 8.94 (s, 1 H), 8.80 (s, 1 H), 8.59 (s, 1 H), 8.21 (m, 2 H), 7.95 (br s, 2 H), 7.88 (t, 1 H), 7.68 (m, 3 H), 7.30 (d, 1 H), 2.45 (s, 3 H) |

TABLE 1-continued

| Example No. | Structure / Chemical name | NMR and/or MS m/z |
|---|---|---|
| 57 | N-(5-(1H-indole-2-carboxyamido)-2-methylphenyl)-4-aminothieno[3,2-d]pyrimidine-7-carboxamide | $^1$H NMR (300 MHz, DMSO-$d_6$) δ 11.73 (s, 1 H), 11.68 (s, 1 H), 10.25 (s, 1 H), 8.94 (s, 1 H), 8.65 (s, 1 H), 8.58 (s, 1 H), 7.92 (br s, 2 H), 7.65 (m, 2 H), 7.46 (m, 2 H), 7.26 (d, 1 H), 7.21 (t, 1 H), 7.05 (t, 1 H), 2.44 (s, 3 H) |
| 58 | 4-amino-N-(2-methyl-5-(picolinamido)phenyl)thieno[3,2-d]pyrimidine-7-carboxamide | $^1$H NMR (300 MHz, DMSO-$d_6$) δ 11.72 (s, 1 H), 10.54 (s, 1 H), 8.92 (s, 1 H), 8.81-8.73 (m, 3 H), 8.54 (s, 1 H), 8.19 (m, 2 H), 8.07 (t, 1 H), 7.67 (br t, 1 H), 7.57 (m, 1 H), 7.27 (t, 1 H), 2.42 (s, 3 H) |
| 59 | 4-amino-N-(2-methyl-5-(nicotinamido)phenyl)thieno[3,2-d]pyrimidine-7-carboxamide | MS m/z [M + 1] 405.41 |
| 60 | 4-amino-N-(5-(isonicotinamido)-2-methylphenyl)thieno[3,2-d]pyrimidine-7-carboxamide | $^1$H NMR (300 MHz, DMSO-$d_6$) δ 11.39 (s, 1 H), 10.56 (s, 1 H), 8.93 (s, 1 H), 8.77 (m, 2 H), 8.69 (d, 1 H), 8.58 (s, 1 H), 7.86 (m, 2 H), 7.57 (dd, 1 H), 7.25 (d, 1 H), 2.43 (s, 3 H) |
| 61 | 4-amino-N-(2-methyl-5-(3-(2-methyl-1H-imidazole-1-yl)-5-(trifluoromethyl)benzamido)phenyl)thieno[3,2-d]pyrimidine-7-carboxamide | $^1$H NMR (300 MHz, DMSO-$d_6$) δ 11.75 (s, 1 H), 10.55 (s, 1 H), 8.92 (s, 1 H), 8.68 (d, 1 H), 8.59 (s, 1 H), 8.35 (d, 2 H), 8.12 (s, 1 H), 7.92 (br s, 2 H), 7.59 (dd, 1 H), 7.50 (s, 1 H), 7.28 (d, 1 H), 6.98 (s, 1 H), 2.44 (s, 3 H), 2.36 (s, 3 H); MS m/z [M + 1] 551.88 |

TABLE 1-continued

| Example No. | Chemical name Structure | NMR and/or MS m/z |
|---|---|---|
| 62 | 4-amino-N-(5-(3-fluorophenylamido)-2-methylphenyl)thieno[3,2-d]pyrimidine-7-carboxamide | $^1$H NMR (300 MHz, DMSO-$d_6$) δ 11.71 (s, 1 H), 10.33 (s, 1 H), 8.92 (s, 1 H), 8.66 (d, 1 H), 8.57 (s, 1 H), 7.93 (m, 2 H), 7.81 (m, 2 H), 7.57 (m, 2 H), 7.43 (br t, 1 H), 7.25 (d, 1 H), 2.43 (s, 3 H) |
| 63 | 4-amino-N-(2-methyl-5-(2-(trifluoromethyl)benzamido)phenyl)thieno[3,2-d]pyrimidine-7-carboxamide | $^1$H NMR (300 MHz, DMSO-$d_6$) δ 11.71 (s, 1 H), 10.53 (s, 1 H), 8.91 (s, 1 H), 8.59 (m, 2 H), 7.97 (m, 2 H), 7.83 (d, 1 H), 7.77 (d, 1 H), 7.69 (br t, 2 H), 7.47 (d, 1 H), 7.24 (d, 1 H), 2.45 (s, 3 H) |
| 64 | (R)-4-amino-N-(5-(3-(3-(dimethylamino)pyrrolidine-1-yl)-5-(trifluoromethyl)benzamido)-2-methylphenyl)thieno[3,2-d]pyrimidine-7-carboxamide | $^1$H NMR (300 MHz, DMSO-$d_6$) δ 11.55 (s, 1 H), 10.34 (s, 1 H), 8.92 (s, 1 H), 8.64 (s, 1 H), 8.57 (s, 1 H), 7.91 (m, 2 H), 7.55 (d, 1 H), 7.53 (s, 1 H), 7.34 (s, 1 H), 7.28 (d, 1 H), 6.93 (s, 1 H), 3.65-3.51 (m, 4 H), 2.43 (s, 3 H), 2.38 (s, 6 H), 2.28 (m, 2 H), 1.95 (m, 1 H) |
| 65 | 4-amino-N-(5-(3-methoxybenzamido)-2-methylphenyl)thieno[3,2-d]pyrimidine-7-carboxamide | $^1$H NMR (300 MHz, DMSO-$d_6$) δ 11.70 (s, 1 H), 10.23 (s, 1 H), 8.91 (s, 1 H), 8.68 (d, 1 H), 8.57 (s, 1 H), 7.92 (br s, 2 H), 7.54 (m, 3 H), 7.42 (t, 1 H), 7.24 (d, 1 H), 7.13 (dd, 1 H), 3.83 (s, 3 H), 2.42 (s, 3 H) |

TABLE 1-continued

| Example No. | Structure / Chemical name | NMR and/or MS m/z |
|---|---|---|
| 66 | 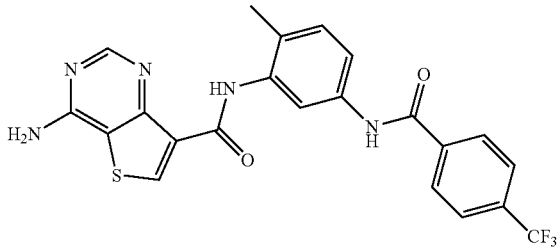 [SMILES: Cc1ccc(NC(=O)c2ccc(C(F)(F)F)cc2)cc1NC(=O)c1csc2c(N)ncnc12]<br>4-amino-N-(2-methyl-5-(4-(trifluoromethyl)benzamido)phenyl)thieno[3,2-d]pyrimidine-7-carboxamide | $^1$H NMR (300 MHz, DMSO-$d_6$) δ 11.73 (s, 1 H), 10.50 (s, 1 H), 8.92 (s, 1 H), 8.68 (d, 1 H), 8.57 (s, 1 H), 8.16 (d, 2 H), 7.91 (m, 4 H), 7.57 (dd, 1 H), 7.26 (d, 1 H), 2.44 (s, 3 H) |
| 67 | 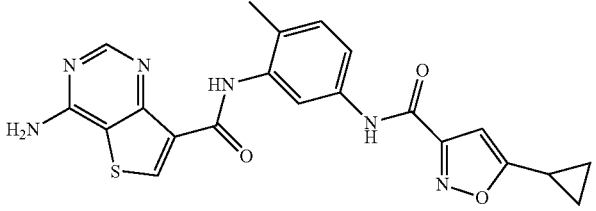 [SMILES: Cc1ccc(NC(=O)c2cc(C3CC3)on2)cc1NC(=O)c1csc2c(N)ncnc12]<br>N-(3-(4-aminothieno[3,2-d]pyrimidine-7-carboxyamido)-4-methylphenyl)-5-cyclopropylisoxazol-3-carboxamide | $^1$H NMR (300 MHz, DMSO-$d_6$) δ 11.72 (s, 1 H) 10.58 (s, 1 H), 8.92 (s, 1 H), 8.68 (s, 1 H), 8.57 (s, 1 H), 7.92 (br s, 2 H), 7.41 (dd, 1 H), 7.24 (d, 1 H), 6.61 (s, 1 H), 2.42 (s, 3 H), 2.12 (m, 1 H), 1.10 (m, 2 H), 0.97 (m, 2 H); MS m/z [M + 1] 435.26 |
| 68 | 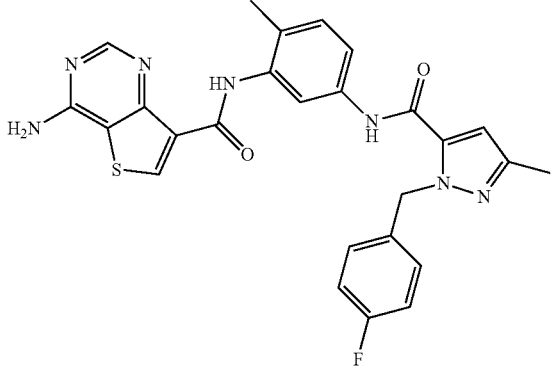 [SMILES: Cc1cc(C(=O)Nc2ccc(C)c(NC(=O)c3csc4c(N)ncnc34)c2)n(Cc2ccc(F)cc2)n1]<br>4-amino-N-(5-(1-(4-fluorobenzyl)-3-methyl-1H-pyrazole-5-carboxyamido)-2-methylphenyl)thieno[3,2-d]pyrimidine-7-carboxamide | MS m/z [M + 1] 516.22 |
| 69 | 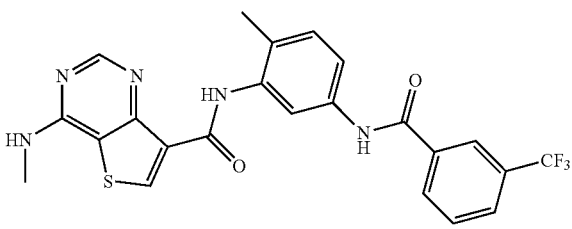 [SMILES: CNc1ncnc2c(C(=O)Nc3cc(NC(=O)c4cccc(C(F)(F)F)c4)ccc3C)csc12]<br>N-(2-methyl-5-(3-(trifluoromethyl)benzamido)phenyl)-4-(methylamino)thieno[3,2-d]pyrimidine-7-carboxamide | $^1$H NMR (300 MHz, DMSO-$d_6$) δ 11.73 (s, 1 H), 10.50 (s, 1 H), 8.88 (s, 1 H), 8.66 (s, 2 H), 8.29 (m, 3 H), 7.95 (d, 1 H), 7.77 (t, 1 H), 7.58 (d, 1 H), 7.27 (d, 1 H), 3.01 (d, 3 H), 2.44 (s, 3 H); MS m/z [M + 1] 486.39 |
| 70 | 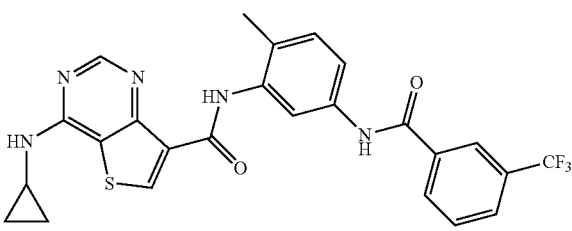 [SMILES: Cc1ccc(NC(=O)c2cccc(C(F)(F)F)c2)cc1NC(=O)c1csc2c(NC3CC3)ncnc12]<br>4-(cycloamino)-N-(2-methyl-5-(3-(trifluoromethyl)benzamido)phenyl)thieno[3,2-d]pyrimidine-7-carboxamide | $^1$H NMR (300 MHz, DMSO-$d_6$) δ 11.76 (s, 1 H), 10.50 (s, 1 H), 8.94 (s, 1 H), 8.66 (br s, 2 H), 8.48 (br s, 1 H), 8.31 (s, 1 H), 8.28 (d, 1 H), 7.95 (d, 1 H), 7.77 (t, 1 H), 7.58 (dd, 1 H), 7.27 (d, 1 H), 3.05 (m, 1 H), 2.44 (s, 3 H), 0.83 (m, 2 H), 0.68 (br s, 2 H); MS m/z [M + 1] 512.25 |

TABLE 1-continued

| Example No. | Chemical name Structure | NMR and/or MS m/z |
|---|---|---|
| 71 | 4-(cyclopentylamino)-N-(2-methyl-5-(3-(trifluoromethyl)benzamido)phenyl)thieno[3,2-d]pyrimidine-7-carboxamide | $^1$H NMR (300 MHz, DMSO-$d_6$) δ 11.78 (s, 1 H), 10.50 (s, 1 H), 8.90 (s, 1 H), 8.67 (s, 1 H), 8.60 (s, 1 H), 8.27 (m, 3 H), 7.95 (d, 1 H), 7.77 (t, 1 H), 7.58 (d, 1 H), 7.26 (d, 1 H), 4.58 (m, 1 H), 2.44 (s, 3 H), 2.01-1.47 (m, 8 H) |
| 72 | N-(2-methyl-5-(3-(trifluoromethyl)benzamido)phenyl)-4-(6-methylpyridine-3-ylamino)thieno[3,2-d]pyrimidine-7-carboxamide | MS m/z [M + 1] 563.07 |
| 73 | 4-(4-(4-ethylpiperazine-1-yl)phenylamino)-N-(2-methyl-5-(3-(trifluoromethyl)benzamido)phenyl)thieno[3,2-d]pyrimidine-7-carboxamide | $^1$H NMR (400 MHz, DMSO-$d_6$) δ 11.72 (s, 1H), 10.53 (s, 1H), 10.04 (s, 1H), 9.43 (br s, 1H), 8.98 (s, 1H), 8.72 (s, 1H), 8.69 (s, 1H), 8.31 (s, 1H), 8.29 (d, 1H), 7.97 (d, 1H), 7.79 (t, 1H), 7.58 (d, 2H), 7.29 (d, 1H), 7.08 (d, 2H), 3.89 (d, 3H), 3.24-3.11 (m, 5H), 2.98 (t, 2H), 2.46 (s, 3H), 1.27 (t, 3H); MS m/z [M + 1] 660.07 |

TABLE 1-continued

| Example No. | Chemical name Structure | NMR and/or MS m/z |
|---|---|---|
| 74 | 4-(cyclopropylamino)-N-(2-methyl-5-(3-(4-methyl-1H-imidazole-1-yl)-5-(trifluoromethyl)benzamido)phenyl)thieno[3,2-d]pyrimidine-7-carboxamide | $^1$H NMR (300 MHz, DMSO-$d_6$) δ 11.79 (s, 1 H), 10.54 (s, 1 H), 8.94 (s, 1 H), 8.68 (br s, 1 H), 8.65 (s, 1 H), 8.50 (br s, 1 H), 8.46 (s, 1 H), 8.40 (s, 1 H), 8.22 (s, 1 H), 8.18 (s, 1 H), 7.71 (s, 1 H), 7.59 (dd, 1 H), 7.29 (d, 1 H), 3.03 (m, 1 H), 2.45 (s, 3 H), 2.18 (s, 3 H), 0.85 (m, 2 H), 0.68 (m, 2 H); MS m/z [M + 1] 614.0 |
| 75 | 4-(cyclopropylamino)-N-(2-methyl-5-(4-(4-methylpiperazin-1-yl)-3-(trifluoromethyl)benzamido)phenyl)thieno[3,2-d]pyrimidine-7-carboxamide | MS m/z [M + 1] 610.67 |
| 76 | (S)-4-(cyclopropylamino)-N-(5-(4-((3-(dimethylamino)pyrrolidin-1-yl)methyl)-3-(trifluoromethyl)benzoamido)-2-methylphenyl)thieno[3,2-d]pyrimidine-7-carboxamide | MS m/z [M + 1] 638.58 |

| Example No. | Structure / Chemical name | NMR and/or MS m/z |
|---|---|---|
| 77 | 4-(cyclopropylamino)-N-(2-methyl-5-(4-((4-methyl-1H-imidazole-1-yl)methyl)-3-(trifluoromethyl)benzoamido)phenyl)thieno[3,2-d]pyrimidine-7-carboxamide | MS m/z [M + 1] 606.57 |
| 78 | N-(2-methyl-5-(3-(4-methyl-1H-imidazole-1-yl)-5-(trifluoromethyl)benzoamido)phenyl)-4-(methylamino)thieno[3,2-d]pyrimidine-7-carboxamide | $^1$H NMR (300 MHz, DMSO-$d_6$) δ 11.75 (s, 1 H), 10.53 (s, 1 H), 8.89 (s, 1 H), 8.66 (s, 2 H), 8.46 (s, 1H), 8.39 (s, 1 H), 8.33 (br q, 1 H), 8.22 (s, 1 H), 8.18 (s, 1 H), 7.71 (s, 1 H), 7.59 (d, 1 H), 7.29 (d, 1 H), 3.03 (d, 3H), 2.45 (s, 3 H), 2.18 (s, 3 H); MS m/z [M + 1] 566.49 |
| 79 | 4-(ethylamino)-N-(2-methyl-5-(3-(4-methyl-1H-imidazole-1-yl)-5-(trifluoromethyl)benzoamido)phenyl)thieno[3,2-d]pyrimidine-7-carboxamide | $^1$H NMR (300 MHz, DMSO-$d_6$) δ 11.76 (s, 1 H), 10.53 (s, 1 H), 8.89 (s, 1 H), 8.67 (s, 1 H), 8.64 (s, 1 H), 8.46 (s, 1 H), 8.39 (s, 1 H), 8.38 (t, 1 H), 8.22 (s, 1 H), 8.18 (s, 1 H), 7.71 (s, 1 H), 7.57 (d, 1 H), 7.29 (d, 1 H), 3.55 (m, 2 H), 2.42 (s, 3 H), 2.18 (s, 3 H), 1.22 (t, 3 H); MS m/z [M + 1] 580.58 |

TABLE 1-continued

| Example No. | Chemical name Structure | NMR and/or MS m/z |
|---|---|---|
| 80 | 4-(cyclopentylamino)-N-(2-methyl-5-(3-(4-methyl-1H-imidazole-1-yl)-5-(trifluoromethyl)benzoamido)phenyl)thieno[3,2-d]pyrimidine-7-carboxamide | MS m/z [M + 1] 620.59 |
| 81 | N-(2-methyl-5-(3-(4-methyl-1H-imidazole-1-yl)-5-(trifluoromethyl)benzoamido)phenyl)-4-(4-(4-methylpiperazin-1-yl)phenylamino)thieno[3,2-d]pyrimidine-7-carboxamide | MS m/z [M + 1] 726.77 |
| 82 | 4-(cyclopropylamino)-N-(2-methyl-5-(4-(4-methyl-1H-imidazole-1-yl)-3-(trifluoromethyl)benzoamido)phenyl)thieno[3,2-d]pyrimidine-7-carboxamide | $^1$H NMR (300 MHz, DMSO-$d_6$) δ 11.8 (s, 1H), 10.6 (s, 1H), 8.93 (s, 1H), 8.67 (d, 2H), 8.47 (s, 2H), 8.39 (d, 1H), 7.94 (s, 1H), 7.75 (d, 1H), 7.60 (m, 1H), 7.29 (m, 1H), 7.11 (s, 1H), 3.05 (m, 1H), 2.18 (s, 3H), 0.84 (m,2H) 0.66 (m, 2H) |

TABLE 1-continued

| Example No. | Chemical name Structure | NMR and/or MS m/z |
|---|---|---|
| 83 | 4-(cyclopropylamino)-N-(2-methyl-5-(3-(2-methyl-1H-imidazole-1-yl)-5-(trifluoromethyl)benzoamido)phenyl)thieno[3,2-d]pyrimidine-7-carboxamide | $^1$H NMR (300 MHz, DMSO-$d_6$) δ 11.8 (s, 1H), 10.6 (s, 1H), 8.93 (s, 1H), 8.67 (d, 2H), 8.49 (s, 1H), 8.38 (d, 2H), 8.12 (s, 1H), 7.60 (m, 2H), 7.29 (m, 1H), 7.09 (s, 1H), 3.04 (m, 1H), 2.39 (s, 3H), 0.84 (m, 2H), 0.70 (m, 2H) |
| 84 | (R)-4-(cyclopropylamino)-N-(5-(3-(3-(dimethylamino)pyrrolidine-1-yl)-5-(trifluoromethyl)benzoamide)-2-methylphenyl)thieno[3,2-d]pyrimidine-7-carboxamide | $^1$H NMR (300 MHz, DMSO-$d_6$) δ 11.8 (s, 1H), 10.3 (s, 1H), 8.93 (s, 1H), 8.65 (s, 2H), 8.49 (d, 1H), 7.55 (d, 1H), 7.49 (s, 1H), 7.34 (s, 1H), 7.35 (d, 1H), z7.49 (s, 1H), 7.34 (s, 1H), 7.25 (d, 1H), 6.94 (s, 1H), 3.56 (m, 4H), 3.04 (m, 1H), 2.26 (s, 6H), 0.77 (m, 6H) |
| 85 | 4-(cyclopropylamino)-N-(2-methyl-5-(3-(4-methylpiperazin-1-yl)-5-(trifluoromethyl)benzoamido)phenyl)thieno[3,2-d]pyrimidine-7-carboxamide | $^1$H NMR (300 MHz, DMSO-$d_6$) δ 11.8 (s, 1H), 10.4 (s, 1H), 8.93 (s, 1H), 8.64 (s, 1H), 8.49 (s, 1H), 7.74 (s, 1H), 7.63 (s, 1H), 7.56 (d, 1H), 7.36 (s, 1H), 7.25 (m, 1H), 3.06 (m, 1H), 2.30 (s, 3H), 0.80 (m, 2H), 0.66 (m, 2H) |

TABLE 1-continued

| Example No. | Structure / Chemical name | NMR and/or MS m/z |
|---|---|---|
| 86 | 4-(cyclopropylamino)-N-(2-methyl-5-(3-(morpholino-5-(trifluoromethyl)benzoamido)phenyl)thieno[3,2-d]pyrimidine-7-carboxamide | $^1$H NMR (300 MHz, DMSO-$d_6$) δ 11.8 (s, 1H), 10.4 (s, 1H), 8.93 (s, 1H), 8.64 (s, 2H), 8.51 (s, 1H), 7.94 (s, 1H), 7.75 (s, 1H), 7.67 (s, 1H), 7.56 (d, 1H), 7.38 (s, 1H), 7.27 (d, 1H), 3.77 (m, 4H), 3.05 (m, 1H), 2.43 (m, 4H), 0.83 (m, 2H), 0.69 (m, 2H) |
| 87 | 4-(cyclopropylamino)-N-(2-methyl-5-(4-((4-methyl-1,4-diazepan-1-yl)methyl)-3-(trifluoromethyl)benzoamido)phenyl)thieno[3,2-d]pyrimidine-7-carboxamide | $^1$H NMR (300 MHz, DMSO-$d_6$) δ 11.8 (s, 1H), 10.5 (s, 1H), 8.93 (s, 1H), 8.66 (s, 2H), 8.50 (s, 1H), 8.25 (d, 2H), 7.98 (d, 1H), 7.58 (d, 1H), 7.27 (d, 1H), 3.83 (s, 2H), 3.04 (m, 1H), 2.70 (m, 8H), 2.44 (s, 3H), 2.39 (s, 3H), 1.80 (m, 2H), 0.83 (m, 2H), 0.69 (m, 2H); MS m/z [M + 1] 638.62 |
| 88 | 4-(cyclopropylamino)-N-(5-(4-(2,4-dimethyl-1H-imidazole-1-yl)-3-(trifluoromethyl)benzoamido)-2-methylphenyl)thieno[3,2-d]pyrimidine-7-carboxamide | $^1$H NMR (300 MHz, DMSO-$d_6$) δ 11.8 (s, 1H), 10.7 (s, 1H), 8.94 (s, 1H), 8.68 (d, 2H), 8.48 (m, 2H), 8.39 (d, 1H), 7.73 (d, 1H), 7.61 (d, 1H), 7.29 (d, 1H), 6.93 (s, 1H), 3.06 (m, 1H), 2.46 (s, 3H), 2.10 (s, 3H), 2.02 (s, 3H), 0.84 (m, 2H), 0.69 (m, 2H) |

TABLE 1-continued

| Example No. | Structure / Chemical name | NMR and/or MS m/z |
|---|---|---|
| 89 | 4-(cyclopropylamino)-N-(2-fluoro-5-(3-(4-methyl-1,4-diazepane-1-yl)-5-(trifluoromethyl)benzoamido)thieno[3,2-d]pyrimidine-7-carboxamide | $^1$H NMR (300 MHz, DMSO-$d_6$) δ 12.07 (s, 1H), 10.55 (s, 1H), 8.96 (s, 1H), 8.86 (d, 1H), 8.64 (s, 1H), 8.51 (s, 1H), 7.60 (m, 1H), 7.53 (m, 2H), 7.36 (t, 1H), 7.15 (s, 1H), 3.73 (m, 2H), 3.55 (m, 2H), 3.16 (m, 1H), 2.69 (m, 4H), 2.49 (s, 3H), 2.24 (m, 2H), 0.85 (m, 2H), 0.69 (m, 2H). |
| 90 | 4-(cyclopropylamino)-N-(5-(3-(2,4-dimethyl-1H-imidazole-1-yl)-5-(trifluoromethyl)benzoamido)-2-methylphenyl)thieno[3,2-d]pyrimidine-7-carboxamide | $^1$H NMR (300 MHz, DMSO-$d_6$) δ 11.8 (s, 1H), 10.6 (s, 1H), 8.94 (s, 1H), 8.67 (d, 2H), 8.50 (s, 1H), 8.33 (d, 2H), 8.07 (s, 1H), 7.60 (d, 1H), 7.29 (d, 1H), 7.20 (s, 1H), 3.04 (m, 1H), 2.48 (s, 3H), 2.32 (s, 3H), 2.12 (s, 3H), 0.84 (m, 2H), 0.70 (m, 2H) |
| 91 | N-(5-(3-(1H-imidazole-1-yl)-5-(trifluoromethyl)benzoamido)-2-methylphenyl)-4-(cyclopropylamino)thieno[3,2-d]pyrimidine-7-carboxamide | $^1$H NMR (300 MHz, DMSO-$d_6$) δ 11.8 (s, 1H), 10.6 (s, 1H), 8.94 (s, 1H), 8.68 (d, 2H), 8.55 (m, 3H), 8.29 (s, 1H), 8.23 (s, 1H), 8.04 (s, 1H), 7.62 (d, 1H), 7.30 (d, 1H), 7.18 (s, 1H), 3.04 (m, 1H), 2.46 (s, 3H), 0.85 (m, 2H), 0.70 (m, 2H) |

TABLE 1-continued

| Example No. | Structure / Chemical name | NMR and/or MS m/z |
|---|---|---|
| 92 | (S)-4-(cyclopropylamino)-N-(5-(3-(3-(dimethylamino)pyrrolidin-1-yl)-5-(trifluoromethyl)benzoamido)-2-methylphenyl)thieno[3,2-d]pyrimidine-7-carboxamide | $^1$H NMR (300 MHz, DMSO-$d_6$) δ 11.8 (s, 1H), 10.3 (s, 1H), 8.93 (s, 1H), 8.64 (d, 2H), 8.51 (s, 1H), 7.55 (d, 1H), 7.46 (s, 1H), 7.32 (s, 1H), 7.26 (d, 1H), 6.91 (s, 1H), 3.54 (m, 4H), 3.15 (m, 1H), 3.05 (m, 1H), 2.44 (s, 3H), 2.22 (s, 6H), 1.89 (m, 2H), 0.84 (m, 2H), 0.69 (m, 2H) |
| 93 | 4-(cyclopropylamino)-N-(2-methyl-5-(3-(4-methyl-1,4-diazepan-1-yl)-5-(trifluoromethyl)benzoamido)thieno[3,2-d]pyrimidine-7-carboxamide | $^1$H NMR (300 MHz, DMSO-$d_6$) δ 11.8 (s, 1H), 10.3 (s, 1H), 8.93 (s, 1H), 8.64 (d, 2H), 8.49 (s, 1H), 7.54 (d, 1H), 7.45 (s, 2H), 7.26 (d, 1H), 7.05 (s, 1H), 3.63 (m, 2H), 3.54 (t, 2H), 3.05 (m, 1H), 2.70 (m, 2H), 2.44 (s, 3H), 2.28 (s, 3H), 1.92 (m, 2H), 0.84 (m, 2H), 0.69 (m, 2H) |
| 94 | (R)-4-(cyclopropylamino)-N-(5-(4-(3-(dimethylamino)pyrrolidine-1-yl)-3-(trifluoromethyl)benzoamido)-2-methylphenyl)thieno[3,2-d]pyrimidine-7-carboxamide | $^1$H NMR (300 MHz, DMSO-$d_6$) δ 11.8 (s, 1H), 10.2 (s, 1H), 8.93 (s, 1H), 8.63 (d, 2H), 8.49 (s, 1H), 8.25 (s, 1H), 8.08 (d, 1H), 7.55 (d, 1H), 7.23 (d, 1H), 7.04 (d, 1H), 3.52 (m, 5H), 3.04 (m, 1H), 2.74 (m, 2H), 2.43 (s, 3H), 2.19 (s, 6H), 1.93 (m, 1H), 1.77 (m, 1H), 0.84 (m, 2H), 0.68 (m, 2H) |

TABLE 1-continued

| Example No. | Structure / Chemical name | NMR and/or MS m/z |
|---|---|---|
| 95 | (S)-4-(cyclopropylamino)-N-(5-(4-(3-(dimethylamino)pyrrolidine-1-yl)-3-(trifluoromethyl)benzoamido)-2-methylphenyl)thieno[3,2-d]pyrimidine-7-carboxamide | $^1$H NMR (300 MHz, DMSO-$d_6$) δ 11.7 (s, 1H), 10.2 (s, 1H), 8.93 (s, 1H), 8.63 (d, 2H), 8.49 (s, 1H), 8.25 (s, 1H), 8.08 (d, 1H), 7.55 (d, 1H), 7.23 (d, 1H), 7.04 (d, 1H), 3.52 (m, 5H), 3.04 (m, 1H), 2.74 (m, 2H), 2.43 (s, 3H), 2.19 (s, 6H), 1.93 (m, 1H), 1.77 (m, 1H), 0.84 (m, 2H), 0.68 (m, 2H) |
| 96 | N-(2-methyl-5-(3-(4-methyl-1H-imidazole-1-yl)-5-(trifluoromethyl)benzoamido)phenyl)-4-(1-methylpiperidine-4-ylamino)thieno[3,2-d]pyrimidine-7-carboxamide | 1H NMR (DMSO, 300 MHz); δ 11.74 (s, 1H), 10.52 (s, 1H), 8.89 (s, 1H), 8.64 (m, 2H), 8.45 (s, 1H), 8.39 (s, 1H), 8.19 (m, 3H), 7.70 (s, 1H), 7.58 (d, 1H), 7.28 (d, 1H), 4.10 (m, 1H), 2.80 (m, 2H), 2.43 (s, 3H), 2.17 (d, 6H), 1.96 (m, 4H), 1.65 (m, 2H). |
| 97 | 4-(cyclopropylamino)-N-(5-(4-(diethylamino)-3-(trifluoromethyl)benzoamido)-2-methylphenyl)thieno[3,2-d]pyrimidine-7-carboxamide | 1H NMR (DMSO, 300 MHz); δ 11.75 (s, 1H), 10.41 (s, 1H), 8.93 (s, 1H), 8.64 (s, 2H), 8.49 (s, 1H), 8.24 (s, 1H), 8.21 (d, 1H), 7.63 (d, 1H), 7.54 (dd, 1H), 7.24 (d, 1H), 3.30 (m, 1H), 3.02 (q, 4H), 2.43 (s, 3H), 0.94 (t, 6H), 0.82 (m, 2H), 0.68 (m, 2H). |
| 98 | 4-(cyclopropylamino)-N-(2-methyl-5-(4-(1-methylpiperidine-4-ylamino)-3-(trifluoromethyl)benzoamido)phenyl)thieno[3,2-d]pyrimidine-7-carboxamide | 1H NMR (DMSO, 300 MHz); δ 11.72 (s, 1H), 10.11 (s, 1H), 8.92 (s, 1H), 8.64 (s, 1H), 8.59 (s, 1H), 8.49 (s, 1H), 8.12 (s, 1H), 8.06 (d, 1H), 7.53 (d, 1H), 7.22 (d, 1H), 7.00 (d, 1H), 5.14 (d, 1H), 3.30 (m, 1H), 3.03 (m, 1H), 2.68 (m, 2H), 2.41 (s, 3H), 2.24 (s, 3H), 2.06 (m, 2H), 1.90 (m, 2H), 1.60 (m, 2H), 0.83 (m, 2H), 0.67 (m, 2H). |

TABLE 1-continued

| Example No. | Structure | NMR and/or MS m/z |
|---|---|---|
| 99 | 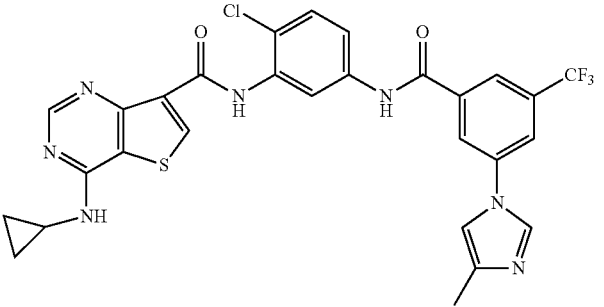 [SMILES: Cc1cn(-c2cc(C(=O)Nc3ccc(Cl)c(NC(=O)c4csc5c(NC6CC6)ncnc45)c3)cc(C(F)(F)F)c2)cn1]<br>N-(2-chloro-5-(3-(4-methyl-1H-imidazole-1-yl)-5-(trifluoromethyl)benzoamido)phenyl)-4-(cyclopropylamino)thieno[3,2-d]pyrimidine-7-carboxamide | $^1$H NMR (300 MHz, DMSO-$d_6$) δ 12.21 (s, 1H), 10.72 (s, 1H), 9.00 (d, 2H), 8.65 (s, 1H), 8.50 (s, 1H), 8.46 (s, 1H), 8.40 (s, 1H), 8.24 (s, 1H), 8.17 (s, 1H), 7.71 (m, 2H), 7.57 (d, 1H), 3.04 (m, 1H), 2.18 (s, 3H), 0.83 (m, 2H), 0.68 (m, 2H). |
| 100 | 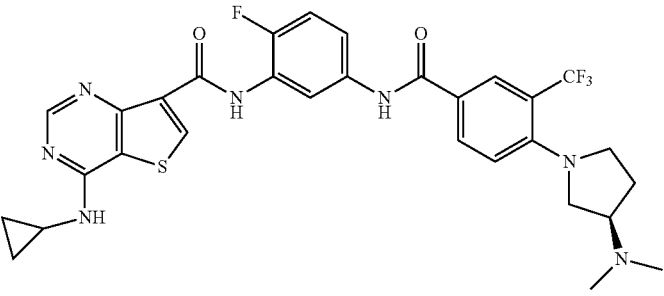 [SMILES: CN(C)[C@@H]1CCN(c2ccc(C(=O)Nc3ccc(F)c(NC(=O)c4csc5c(NC6CC6)ncnc45)c3)cc2C(F)(F)F)C1]<br>(R)-4-(cyclopropylamino)-N-(5-(4-(3-(dimethylamino)pyrrolidine-1-yl)-3-(trifluoromethyl)benzoamido)-2-fluorophenyl)thieno[3,2-d]pyrimidine-7-carboxamide | 1H NMR (DMSO, 300 MHz); δ 12.14 (s, 1H), 10.26 (s, 1H), 8.96 (s, 1H), 8.84 (dd, 1H), 8.64 (s, 1H), 8.51 (s, 1H), 8.23 (d, 1H), 8.06 (d, 1H), 7.62 (m, 1H), 7.33 (t, 1H), 7.05 (d, 1H), 3.47 (m, 4H), 3.02 (m, 1H), 2.71 (m, 1H), 2.18 (s, 6H), 2.16 (m, 1H), 1.76 (m, 1H), 0.84 (m, 2H), 0.68 (m, 2H). |
| 101 | 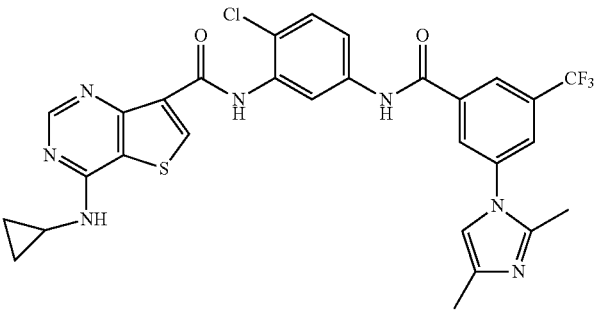<br>N-(2-chloro-5-(3-(2,4-dimethyl-1H-imidazole-1-yl)-5-(trifluoromethyl)benzoamido)phenyl)-4-(cyclopropylamino)thieno[3,2-d]pyrimidine-7-carboxamide | $^1$H NMR (300 MHz, DMSO-$d_6$) δ 12.05 (s, 1H), 10.45 (s, 1H), 8.85 (s, 1H), 8.79 (d, 1H), 8.61 (s, 1H), 8.36 (s, 1H), 8.27 (s, 1H), 8.24 (s, 1H), 8.00 (s, 1H), 7.54 (d, 1H), 7.19 (d, 1H), 7.14 (s, 1H), 3.08 (m, 1H), 2.65 (s, 3H), 2.49 (s, 3H), 0.78 (m, 2H), 0.64 (m, 2H). |
| 102 | 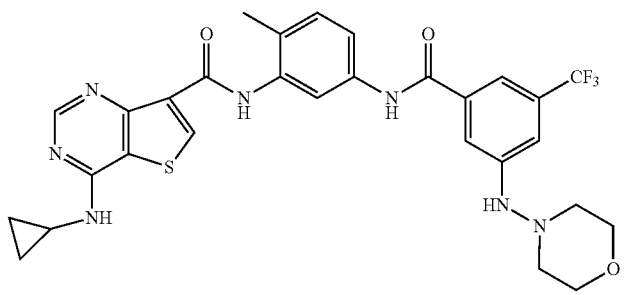 [SMILES: Cc1ccc(NC(=O)c2cc(NN3CCOCC3)cc(C(F)(F)F)c2)cc1NC(=O)c1csc2c(NC3CC3)ncnc12]<br>4-(cyclopropylamino)-N-(2-methyl-5-(3-(morpholinoamino)-5-(trifluoromethyl)benzoamido)phenyl)thieno[3,2-d]pyrimidine-7-carboxamide | 1H NMR (DMSO, 300 MHz); δ 11.75 (s, 1H), 10.38 (s, 1H), 8.92 (s, 1H), 8.63 (s, 2H), 8.49 (s, 1H), 7.73 (s, 1H), 7.66 (s, 1H), 7.55 (d, 1H), 7.37 (s, 1H), 7.25 (d, 1H), 3.76 (br, 4H), 3.30 (br, 4H), 3.03 (m, 1H), 2.44 (s, 3H), 0.85 (m, 2H), 0.69 (m, 2H). |

| Example No. | Structure | NMR and/or MS m/z |
|---|---|---|
| 103 | 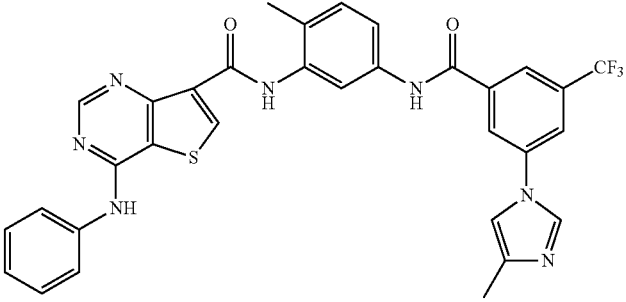 [SMILES: Cc1cn(-c2cc(C(=O)Nc3ccc(C)c(NC(=O)c4csc5c(Nc6ccccc6)ncnc45)c3)cc(C(F)(F)F)c2)cn1] N-(2-methyl-5-(3-(4-methyl-1H-imidazole-1-yl)-5-(trifluoromethyl)benzoamido)phenyl)-4-(phenylamino)thieno[3,2-d]pyrimidine-7-carboxamide | 1H NMR (DMSO, 300 MHz); δ 11.70 (s, 1H), 10.66 (s, 1H), 10.14 (s, 1H), 9.01 (s, 1H), 8.77 (s, 1H), 8.68 (d, 1H), 8.46 (s, 1H), 8.40 (s, 1H), 8.22 (s, 1H), 8.18 (s, 1H), 7.74 (t, 3H), 7.60 (d, 1H), 7.41 (t, 2H), 7.30 (d, 1H), 7.18 (t, 1H), 2.49 (s, 3H), 2.18 (s, 3H). |
| 104 | 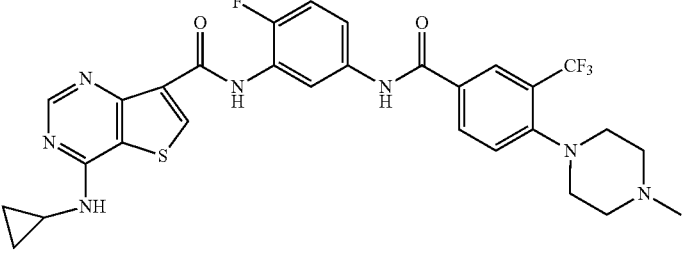 4-(cyclopropylamino)-N-(2-fluoro-5-(4-(4-methylpiperazine-1-yl)-3-(trifluoromethyl)benzoamido)phenyl)thieno[3,2-d]pyrimidine-7-carboxamide | 1H NMR (DMSO, 300 MHz); δ 12.05 (s, 1H), 10.43 (s, 1H), 8.91 (s, 1H), 8.81 (d, 1H), 8.58 (s, 1H), 8.46 (s, 1H), 8.16 (m, 2H), 7.55 (m, 2H), 7.33 (1, 1H), 3.26 (m, 4H), 3.04~2.91 (m, 5H), 2.22 (s, 3H), 0.78 (m, 2H), 0.63 (m, 2H). |
| 105 | 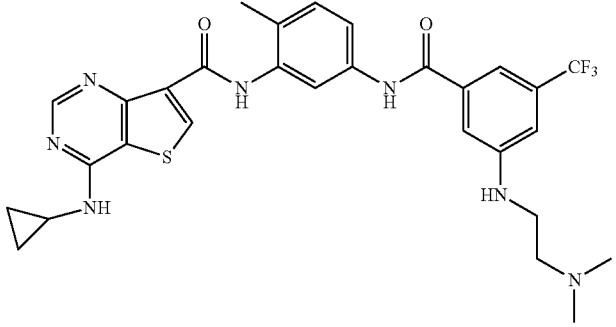 [SMILES: Cc1ccc(NC(=O)c2cc(NCCN(C)C)cc(C(F)(F)F)c2)cc1NC(=O)c1csc2c(NC3CC3)ncnc12] 4-(cyclopropylamino)-N-(5-(3-(2-(dimethylamino)ethylamino)-5-(trifluoromethyl)benzoamido)-2-methylphenyl)thieno[3,2-d]pyrimidine-7-carboxamide | 1H NMR (DMSO, 300 MHz); δ 11.78 (s, 1H), 10.33 (s, 1H), 8.94 (s 1H), 8.67 (m, 2H), 8.58 (s, 1H), 7.57 (d, 1H), 7.41 (d, 2H), 7.27 (d, 1H), 7.08 (s, 1H), 6.25 (s, 1H), 3.22 (m, 1H), 3.07 (m, 2H), 2.46 (s, 3H), 2.22 (s, 6H), 2.20 (m, 2H), 0.87 (m, 2H), 0.74 (m, 2H). |
| 106 | 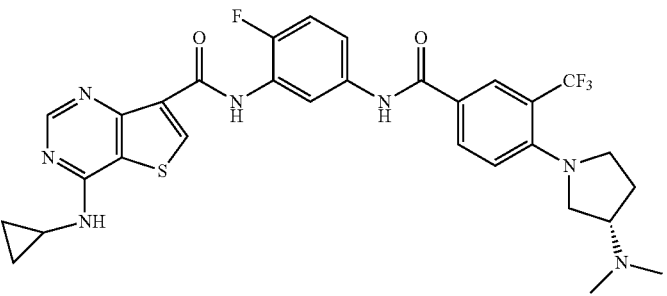 [SMILES: CN(C)[C@H]1CCN(c2ccc(C(=O)Nc3ccc(F)c(NC(=O)c4csc5c(NC6CC6)ncnc45)c3)cc2C(F)(F)F)C1] (S)-4-(cyclopropylamino)-N-(5-(4-(3-(dimethylamino)pyrrolidine-1-yl)-3-(trifluoromethyl)benzoamido)-2-fluorophenyl)thieno[3,2-d]pyrimidine-7-carboxamide | 1H NMR (DMSO, 300 MHz); δ 12.14 (s, 1H), 10.26 (s, 1H), 8.96 (s, 1H), 8.84 (dd, 1H), 8.63 (s, 1H), 8.50 (s, 1H), 8.24 (d, 1H), 8.06 (dd, 1H), 7.61(m, 1H), 7.29 (t, 1H), 7.05 (d, 1H), 3.47 (m, 4H), 3.02 (m, 1H), 2.69 (m, 1H), 2.18 (s, 6H), 2.16 (m, 1H), 1.76 (m, 1H), 0.82 (m, 2H), 0.69 (m, 2H). |

| Example No. | Chemical name Structure | NMR and/or MS m/z |
|---|---|---|
| 107 | (S)-4-(cyclopropylamino)-N-(5-(3-(3-(dimethylamino)pyrrolidine-1-yl)-5-(trifluoromethyl)benzoamido)-2-fluorophenyl)thieno[3,2-d]pyrimidine-7-carboxamide | 1H NMR (DMSO, 300 MHz); δ 12.16 (s, 1H), 10.43 (s, 1H), 8.96 (s, 1H), 8.86 (dd, 1H), 8.63 (s, 1H), 8.51 (s, 1H), 7.61 (m, 1H), 7.45 (s, 1H), 7.33 (m, 2H), 6.91 (s, 1H), 3.54 (m, 4H), 3.13 (t, 1H), 3.03 (m, 1H), 2.08 (s, 1H), 2.20 (s, 6H), 1.82 (m, 1H), 0.84 (m, 2H), 0.63 (m, 2H). |
| 108 | 4-(cyclopropylamino)-N-(5-(3-(2,4-dimethyl-1H-imidazole-1-yl)-5-(trifluoromethyl)benzoamido)-2-fluorophenyl)thieno[3,2-d]pyrimidine-7-carboxamide | 1H NMR (DMSO, 300 MHz); δ 12.20 (s, 1H), 10.63 (s, 1H), 8.97 (s, 1H), 8.89 (m, 1H), 8.64 (s, 1H), 8.51 (s, 1H), 8.33 (s, 1H), 8.30 (s, 1H), 8.08 (s, 1H), 7.65 (m, 1H), 7.36 (t, 1H), 7.20 (s, 1H), 3.04 (m, 1H), 2.32 (s, 3H), 2.16 (s, 3H), 0.84 (m, 2H), 0.68 (m, 2H). |
| 109 | 4-(cyclopropylamino)-N-(2-methyl-5-(3-(piperidine-1-yl)-5-(trifluoromethyl)benzoamido)phenyl)thieno[3,2-d]pyrimidine-7-carboxamide | $^1$H NMR (300 MHz, DMSO-$d_6$) δ 11.8 (s, 1H), 10.4 (s, 1H), 8.93 (s, 1H), 8.64 (s, 2H), 8.52 (s, 1H), 7.72 (s, 1H), 7.56 (d, 2H), 7.32 (s, 1H), 7.25 (d, 1H), 3.33 (m, 4H), 3.04 (m, 1H), 2.44 (s, 3H), 1.73 (m, 6H), 0.84 (m, 2H), 0.68 (m, 2H) |

TABLE 1-continued

| Example No. | Chemical name Structure | NMR and/or MS m/z |
|---|---|---|
| 110 | 4-(cyclopropylamino)-N-(5-(3-(4-ethylpiperazin-1-yl)-5-(trifluoromethyl)benzoamido)-2-methylphenyl)thieno[3,2-d]pyrimidine-7-carboxamide | $^1$H NMR (300 MHz, DMSO-$d_6$) δ 11.8 (s, 1H), 10.4 (s, 1H), 8.93 (s, 1H), 8.65 (s, 2H), 8.53 (s, 1H), 7.75 (d, 2H), 7.56 (d, 1H), 7.48 (s, 1H), 7.27 (d, 1H), 3.30 (m, 4H), 2.49 (m, 4H), 2.44 (s, 3H), 2.37 (q, 2H), 1.04 (t, 3H), 0.84 (m, 2H), 0.69 (m, 2H) |
| 111 | 4-(cyclopropylamino)-N-(2-methyl-5-(4-(1-methylpiperidine-4-yloxy)-3-(trifluoromethyl)benzoamido)phenyl)thieno[3,2-d]pyrimidine-7-carboxamide | $^1$H NMR (300 MHz, DMSO-$d_6$) δ 11.7 (s, 1H), 10.3 (s, 1H), 8.93 (s, 1H), 8.63 (s, 2H), 8.49 (s, 1H), 8.25 (m, 2H), 7.57 (d, 1H), 7.45 (d, 1H), 7.25 (d, 1H), 4.77 (m, 1H), 3.04 (m, 1H), 2.30 (s, 3H), 2.28 (m, 4H), 2.18 (s, 3H), 1.95 (m, 4H), 0.84 (m, 2H), 0.68 (m, 2H); MS m/z [M + 1] 625.18 |
| 112 | 4-(cyclopropylamino)-N-(2-methyl-5-(3-(pyrrolidine-1-yl)-5-(trifluoromethyl)benzoamido)phenyl)thieno[3,2-d]pyrimidine-7-carboxamide | $^1$H NMR (300 MHz, DMSO-$d_6$) δ 11.8 (s, 1H), 10.3 (s, 1H), 8.93 (s, 1H), 8.64 (s, 2H), 8.50 (s, 1H), 7.55 (d, 1H), 7.45 (s, 1H), 7.32 (s, 1H), 7.25 (d, 1H), 6.88 (s, 1H), 3.33 (m, 4H), 3.04 (m, 1H), 2.43 (s, 3H), 1.97 (m, 4H), 0.82 (m, 2H), 0.68 (m, 2H) |
| 113 | (R)-4-(cyclopropylamino)-N-(2-methyl-5-(3-(2-methylpyrrolidine-1-yl)-5-(trifluoromethyl)benzoamido)phenyl)thieno[3,2-d]pyrimidine-7-carboxamide | $^1$H NMR (300 MHz, DMSO-$d_6$) δ 11.8 (s, 1H), 10.6 (s, 1H), 8.94 (s, 1H), 8.66 (s, 2H), 8.59 (s, 1H), 7.60 (d, 1H), 7.45 (d, 2H), 7.24 (d, 1H), 6.88 (s, 1H), 4.14 (m, 3H), 3.15 (s, 3H), 3.04 (m, 1H), 2.44 (s, 3H), 1.98 (m, 4H), 0.84 (m, 2H), 0.68 (m, 2H) |

TABLE 1-continued

| Example No. | Structure / Chemical name | NMR and/or MS m/z |
|---|---|---|
| 114 | 4-(cyclopropylamino)-N-(5-(3-(diethylamino)-5-(trifluoromethyl)benzoamido)-2-methylphenyl)thieno[3,2-d]pyrimidine-7-carboxamide | $^1$H NMR (300 MHz, DMSO-$d_6$) δ 11.8 (s, 1H), 10.4 (s, 1H), 8.93 (s, 1H), 8.66 (s, 2H), 8.52 (s, 1H), 7.55 (d, 1H), 7.42 (d, 2H), 7.26 (d, 1H), 6.98 (s, 1H), 3.45 (q, 4H), 3.04 (m, 1H), 2.44 (s, 3H), 1.12 (t, 6H), 0.82 (m, 2H), 0.69 (m, 2H) |
| 115 | 4-(cyclopropylamino)-N-(5-(3-(ethylamino)-5-(trifluoromethyl)benzoamido)-2-methylphenyl)thieno[3,2-d]pyrimidine-7-carboxamide | $^1$H NMR (300 MHz, DMSO-$d_6$) δ 11.8 (s, 1H), 10.3 (s, 1H), 8.93 (s, 1H), 8.64 (s, 2H), 8.50 (s, 1H), 7.54 (d, 1H), 7.40 (s, 1H), 7.33 (s, 1H), 7.25 (d, 1H), 6.97 (s, 1H), 6.36 (t, 1H), 3.14 (q, 2H), 3.04 (m, 1H), 2.44 (s, 3H), 1.18 (t, 3H), 0.86 (m, 2H), 0.68 (m, 2H) |
| 116 | 4-(cyclopropylamino)-N-(2-methyl-5-(3-(1-methylpiperidine-4-ylamino)-5-(trifluoromethyl)benzoamido)phenyl)thieno[3,2-d]pyrimidine-7-carboxamide | $^1$H NMR (300 MHz, DMSO-$d_6$) δ 11.8 (s, 1H), 10.3 (s, 1H), 8.93 (s, 1H), 8.65 (s, 2H), 8.51 (s, 1H), 7.53 (d, 1H), 7.38 (s, 1H), 7.33 (s, 1H), 7.24 (d, 1H), 7.01 (s, 1H), 6.30 (d, 1H), 3.04 (m, 1H), 2.78 (m, 1H), 2.44 (s, 3H), 2.22 (s, 3H), 2.18 (m, 2H), 1.91 (m, 2H), 1.45 (m, 2H), 0.83 (m, 4H), 0.69 (m, 2H) |
| 117 | 4-(cyclopropylamino)-N-(3-(3-(4-methyl-1H-imidazole-1-yl)-5-(trifluoromethyl)benzoamido)phenyl)thieno[3,2-d]pyrimidine-7-carboxamide | $^1$H NMR (300 MHz, DMSO-$d_6$) δ 11.93 (br, 1H), 10.61 (br, 1H), 9.07 (s, 1H), 8.87 (s, 1H), 8.50 (d, 2H), 8.42 (s, 1H), 8.25 (s, 1H), 8.18 (d, 2H), 7.73 (s, 1H), 7.63 (t, 2H), 7.41 (t, 1H), 3.04 (m, 1H), 2.19 (s, 3H), 0.84 (m, 2H), 0.72 (m, 2H). |

TABLE 1-continued

| Example No. | Structure / Chemical name | NMR and/or MS m/z |
|---|---|---|
| 118 | 4-(cyclopropylamino)-N-(2-methoxy-5-(3-(4-methyl-1H-imidazole-1-yl)-5-(trifluoromethyl)benzoamido)phenyl)thieno[3,2-d]pyrimidine-7-carboxamide | $^{1}$H NMR (300 MHz, DMSO-$d_6$) δ 12.50 (br, 1H), 10.50 (br, 1H), 8.92 (s, 1H), 8.86 (d, 1H), 8.70 (s, 1H), 8.47 (s, 2H), 8.41 (s, 1H), 8.23 (s, 1H), 8.19 (s, 1H), 7.73 (s, 1H), 7.62 (dd, 1H), 7.13 (d, 1H), 3.98 (s, 3H), 3.05 (m, 1H), 2.19 (s, 3H), 0.86 (m, 2H), 0.70 (m, 2H). |
| 119 | 4-(cyclopropylcarboxyamido)-N-(2-methyl-5-(3-(4-methyl-1H-imidazole-1-yl)-5-(trifluoromethyl)benzoamido)phenyl)thieno[3,2-d]pyrimidine-7-carboxamide | $^{1}$H NMR (300 MHz, DMSO-$d_6$) δ 11.82 (br, 1H), 11.64 (br, 1H), 10.57 (br, 1H), 9.14 (s, 1H), 9.07 (s, 1H), 8.70 (s, 1H), 8.46 (s, 1H), 8.41 (s, 1H), 8.23 (s, 1H), 8.18 (s, 1H), 7.83 (s, 1H), 7.72 (d, 1H), 7.30 (d, 3H), 3.30 (m, 1H), 2.49 (s, 3H), 2.25 (s, 3H), 1.01 (m, 4H) |
| 120 | 4-benzoamido-N-(2-methyl-5-(3-(4-methyl-1H-imidazole-1-yl)-5-(trifluoromethyl)benzoamido)phenyl)thieno[3,2-d]pyrimidine-7-carboxamide | $^{1}$H NMR (300 MHz, DMSO-$d_6$) δ 11.62 (br, 1H), 10.58 (br, 1H), 9.20 (d, 2H), 8.72 (d, 1H), 8.48 (s, 1H), 8.41 (s, 1H), 8.24 (s, 1H), 8.20 (s, 1H), 8.13 (d, 2H), 7.73 (s, 1H), 7.61 (m, 4H), 7.34 (d, 1H), 2.49 (s, 3H), 2.20 (s, 3H) |
| 121 | 4-(cyclopropylamino)-N-(2-fluoro-5-(3-(4-methyl-1H-imidazole-1-yl)-5-(trifluoromethyl)benzoamido)phenyl)thieno[3,2-d]pyrimidine-7-carboxamide | $^{1}$H NMR (300 MHz, DMSO-$d_6$) δ 12.21 (br, 1H), 10.64 (br, 1H), 8.98 (s, 1H), 8.89 (dd, 1H), 8.70 (s, 1H), 8.51 (s, 1H), 8.46 (s, 1H), 8.40 (s, 1H), 8.24 (s, 1H), 8.17 (s, 1H), 7.72 (s, 1H), 7.70 (m, 1H), 7.37 (dd, 1H), 3.14 (m, 1H), 2.18 (s, 3H), 0.84 (m, 2H), 0.68 (m, 2H). |

TABLE 1-continued

| Example No. | Structure / Chemical name | NMR and/or MS m/z |
|---|---|---|
| 122 | 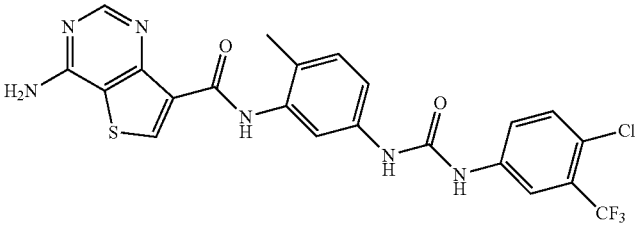 [SMILES: Cc1ccc(NC(=O)Nc2ccc(Cl)c(C(F)(F)F)c2)cc1NC(=O)c1csc2c(N)ncnc12]<br>4-amino-N-(5-(3-(4-chloro-3-(trifluoromethyl)phenyl)ureido)-2-methylphenyl)thieno[3,2-d]pyrimidine-7-carboxamide | $^1$H NMR (300 MHz, DMSO-$d_6$) δ 11.70 (s, 1H), 9.01 (s, 1H), 8.91 (s, 1H), 8.87 (s, 1H), 8.56 (s, 1H), 8.40 (s, 1H), 8.11 (s, 1H), 7.89 (br s, 2H), 7.60 (m, 2H), 7.28 (d, 1H), 7.18 (d, 1H), 2.40 (s, 3H) |
| 123 | 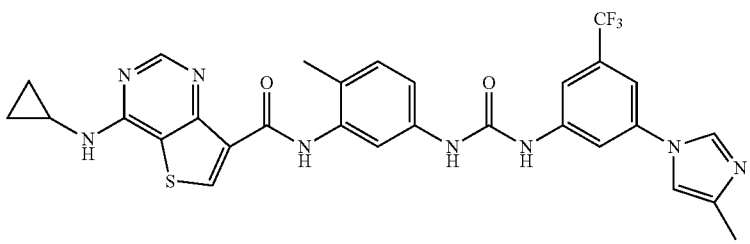 [SMILES: Cc1cn(-c2cc(NC(=O)Nc3ccc(C)c(NC(=O)c4csc5c(NC6CC6)ncnc45)c3)cc(C(F)(F)F)c2)cn1]<br>4-(cyclopropylamino)-N-(2-methyl-5-(3-(3-(4-methyl-1H-imidazol-1-yl)-5-(trifluoromethyl)phenyl)ureido)phenyl)thieno[3,2-d]pyrimidine-7-carboxamide | $^1$H NMR (300 MHz, DMSO-$d_6$) δ 11.76 (br, 2H), 9.06 (d, 1H), 8.94 (s, 1H), 8.64 (m, 2H), 8.51 (s, 1H), 8.40 (d, 1H), 8.2l (s, 1H), 7.94 (d, 1H), 7.53 (d, 1H), 7.32 (m, 2H), 7.19 (m, 1H), 3.04 (m, 1H), 2.37 (s, 3H), 2.18 (s, 3H), 0.85 (m, 2H), 0.69 (m, 2H). |
| 124 | 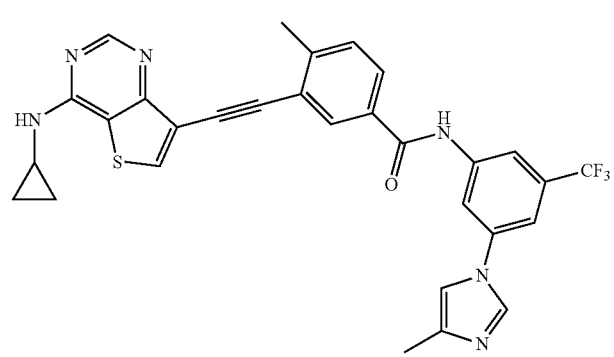 [SMILES: Cc1cn(-c2cc(NC(=O)c3ccc(C)c(C#Cc4csc5c(NC6CC6)ncnc45)c3)cc(C(F)(F)F)c2)cn1]<br>3-((4-(cyclopropylamino)thieno[3,2-d]pyrimidine-7-yl)ethynyl)-4-methyl-N-(3-(4-methyl-1H-imidazole-1-yl)-5-(trifluoromethyl)phenyl)benzamide | MS m/z: 573.17 [M +1]. |
| 125 | 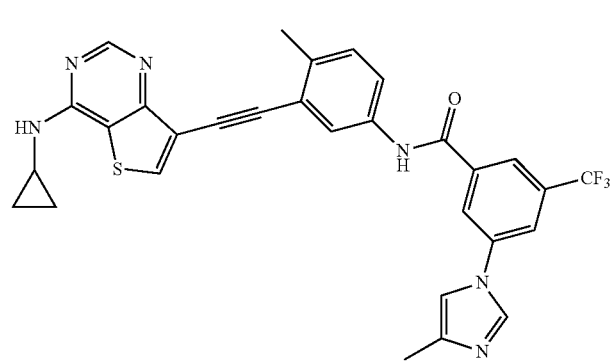 [SMILES: Cc1cn(-c2cc(C(=O)Nc3ccc(C)c(C#Cc4csc5c(NC6CC6)ncnc45)c3)cc(C(F)(F)F)c2)cn1]<br>N-(3-((4-(cyclopropylamino)thieno[3,2-d]pyrimidine-7-yl)ethynyl)-4-methylphenyl)-3-(4-methyl-1H-imidazole-1-yl)-5-(trifluoromethyl)benzamide | MS m/z: 573.19 [M + 1]. |

TABLE 1-continued

| Example No. | Structure / Chemical name | NMR and/or MS m/z |
|---|---|---|
| 126 | 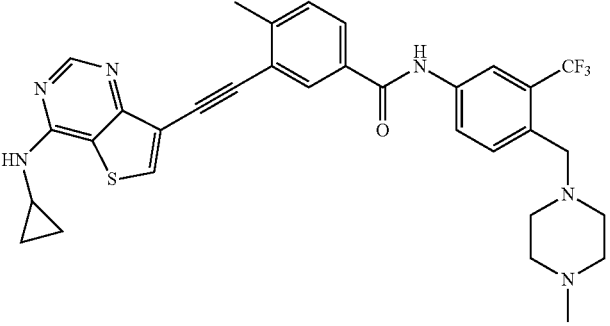 [SMILES: Cc1ccc(C(=O)Nc2ccc(CN3CCN(C)CC3)c(C(F)(F)F)c2)cc1C#Cc1csc2c(NC3CC3)ncnc12]<br>3-((4-(cyclopropylamino)thieno[3,2-d]pyrimidine-7-yl)ethynyl)-4-methyl-N-(4-((4-methylpiperazine-1-yl)methyl)-3-(trifluoromethyl)phenyl)benzamide | MS m/z: 605.15 [M + 1] |
| 127 | 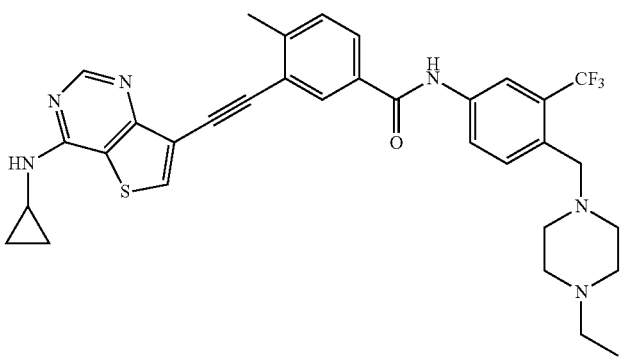 [SMILES: CCN1CCN(Cc2ccc(NC(=O)c3ccc(C)c(C#Cc4csc5c(NC6CC6)ncnc45)c3)cc2C(F)(F)F)CC1]<br>3-((4-(cyclopropylamino)thieno[3,2-d]pyrimidine-7-yl)ethynyl)-N-(4-((4-ethylpiperazine-1-yl)methyl)-3-(trifluoromethyl)phenyl)-4-methylbenzamide | 1H NMR (DMSO, 300 MHz); δ 10.54 (s, 1H), 8.54 (s, 1H), 8.48(s, 1H), 8.19 (m, 3H), 8.05 (d, 1H), 7.91 (d, 1H), 7.70 (d, 1H), 7.5 1 (d, 1H), 3.55 (s, 2H), 2.98 (m, 1H), 2.59 (s, 3H), 2.38 (m, 10H), 0.97 (t, 3H), 0.80 (m, 2H), 0.64 (m, 2H) |
| 128 | 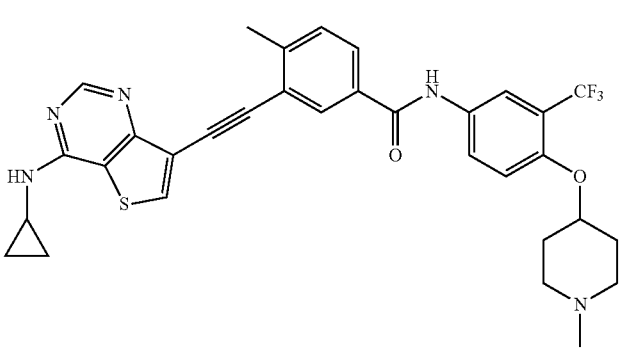 [SMILES: Cc1ccc(C(=O)Nc2ccc(OC3CCN(C)CC3)c(C(F)(F)F)c2)cc1C#Cc1csc2c(NC3CC3)ncnc12]<br>3-((4-(cyclopropylamino)thieno[3,2-d]pyrimidine-7-yl)ethynyl)-4-methyl-N-(4-(1-methylpiperazine-1-yloxy)-3-(trifluoromethyl)phenyl)benzamide | 1H NMR (DMSO, 300 MHz); δ 10.41 (s, 1H), 8.56 (s, 1H), 8.49 (s, 1H), 8.24 (d, 1H), 8.18 (d, 1H), 8.11 (d, 1H), 8.03 (d, 1H), 7.92 (d, 1H), 7.52 (d, 1H), 7.33 (d, 1H), 4.60 (m, 1H), 3.01 (m, 1H), 2.60 (s, 3H), 2.38 (m, 4H), 2.28 (s, 3H), 1.93 (m, 2H), 1.71 (m, 2H), 0.83 (m, 2H), 0.69 (m, 2H) |

Test 1: Kinase Activation Assay ($IC_{50}$)

A kinase domain (Millipore) comprising the entire cytoplasmic sequences of Bcr-Abl$^{wt}$ and Bcr-Abl$^{T315I}$ mutation kinases and a tyrosine kinase assay kit (Panvera, P2837) were used to measure an inhibitory activation on Bcr-abl. Other kinases such as FGFR, Flt, KDR, PDGFR, Fms, Kit, Raf, Tie2, Src, and Ret were also measured by the same method. In order to prepare a sample, the each compound obtained in Examples 1 to 128 was diluted 10 times with a kinase buffer to a concentration of 10~0.0001 μM.

The each kinase was diluted with a kinase buffer to a concentration of 30~300 ng/assay by using the each Kd value. The kinase buffer consisted of 100 mM HEPES (PH 7.4), 25 mM $MgCl_2$, 10 mM $MnCl_2$, and 250 μM $Na_3VO_4$, being kept refrigerated after filtered.

The test was conducted in 96 well polystyrene round bottom plates. First, 10 μL of the diluted sample was combined with 10 μL of the enzyme solution at room temperature for 10 minutes using a shaker. 10 μL of Poly (Glu, Tyr) 4:1 (Sigma) matrix solution in an appropriate concentration and 10 μL of ATP solution (5~300 μM) were added to the sample and subjected to a reaction at room temperature for 60 minutes in a shaker. After 60 minutes, an EDTA solution was added thereto to complete the kinase reaction and the reaction mixture was left in a shaker for 5 minutes at room temperature. A tracer, an antibody, and a fluorescence polarization (FP) diluted reaction solution were mixed at a ratio of 1:1:3 to prepare a detecting solution, 50 μL of which was added to the each sample and subjected to a reaction at room temperature for 30 minutes in a shaker. As fluorescing, light was blocked out and the FP value was measured using a FP instrument (excitation wavelength: 485 nm, and emission wavelength: 530 nm).

And the inhibition on kinase reaction was calculated for the sample in the range of 0~100% as compared to the control group, and the concentration on x-axis at 50% inhibition was obtained as an inhibitory concentration ($IC_{50}$) value.

50% inhibitory concentration ($IC_{50}$)

$Y$=bottom+(top−bottom)/(1+10exp($X$−log $IC_{50}$))

The $IC_{50}$ values of Bcr-Abl$^{wt}$ and Bcr-Abl$^{T315I}$ kinases for the compounds obtained in the examples were summarized in Table 2.

TABLE 2

| Example | Bcr-Abl$^{wt}$ | Bcr-Abl$^{T315I}$ | Example | Bcr-Abl$^{wt}$ | Bcr-Abl$^{T315I}$ |
|---|---|---|---|---|---|
| 3 | * | *** | 56 | ** | *** |
| 6 | ** | *** | 61 | * | * |
| 7 | * | ** | 65 | * | *** |
| 8 | * | * | 66 | ** | *** |
| 12 | * | ** | 67 | * | *** |
| 14 | ** | *** | 68 | *** | *** |
| 17 | * | *** | 71 | * | *** |
| 23 | * | *** | 76 | * | * |
| 24 | * | * | 78 | * | ** |
| 29 | * | *** | 83 | * | * |
| 30 | *** | *** | 86 | * | ** |
| 31 | * | * | 87 | * | * |
| 36 | * | *** | 93 | * | * |
| 39 | * | * | 107 | * | ** |
| 41 | * | * | 110 | * | ** |
| 43 | * | ** | 113 | ** | ** |
| 45 | * | * | 116 | * | * |
| 49 | * | * | 121 | * | * |

\* represents $IC_{50}$ value in the range of 1 nM to 100 nM
\*\* represents $IC_{50}$ value in the range of 100 nM to 1,000 nM
\*\*\* represents $IC_{50}$ value in the range of 1,000 nM to 10,000 nM As shown in Table 2, the inventive compounds have excellent inhibitory activity on Bcr-Abl$^{wt}$ and Bcr-Abl$^{T315I}$ kinases.

What is claimed is:

1. A thieno[3,2-d]compound of formula (I), and a pharmaceutically acceptable salt thereof:

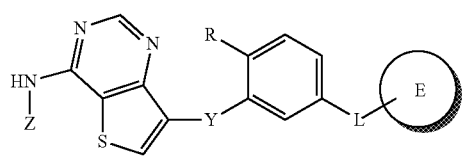

(I)

wherein,
Y is —CH═CR$^1$—, —CC—, or —C(═O)NR$^1$—;
L is —C(═O)NR$^2$—, —NR$^2$C(═O)—, or —NR$^2$C(═O)NR$^2$—;
R$^1$ and R$^2$ are each independently H, $C_{1-6}$alkyl, or $C_{3-8}$cycloalkyl;
R is H, halogen, methyl, or methoxy;
E is $C_{3-14}$aryl or $C_{2-13}$heteroaryl, which is unsubstituted or substituted by 1 to 3 substituents selected from the group consisting of halogen, —NO$_2$, —CN, —NH$_2$, —OH, —CF$_3$, $C_{1-6}$alkyl, hydroxy-$C_{1-6}$alkyl, $C_{3-8}$cycloalkyl, —(CH$_2$)$_n$—$C_{1-6}$alkylamino, —(CH$_2$)$_n$-di$C_{1-6}$alkylamino, —(CH$_2$)$_n$C$_{1-6}$alkoxy, —(CH$_2$)$_n$—OS(═O)$_2$—$C_{1-6}$alkyl, —(CH$_2$)$_n$—$C_{3-14}$aryl, —(CH$_2$)$_n$—$C_{2-13}$heteroaryl and —(CH$_2$)$_n$—$C_{2-13}$heterocycloalkyl, wherein n is an integer number of 0 to 3, and the aryl, heteroaryl and heterocycloalkyl are each independently unsubstituted or substituted by a substituent selected from the group consisting of $C_{1-6}$alkyl, hydroxy-$C_{1-6}$alkyl, halogen, di$C_{1-6}$alkylamino, and $C_{1-6}$ alkoxy; and
Z is H, —C(═O)R$^3$, $C_{1-6}$alkyl, hydroxy$C_{1-6}$alkyl, $C_{3-8}$cycloalkyl, $C_{2-7}$heterocycloalkyl, $C_{3-14}$aryl, or $C_{2-13}$heteroaryl, wherein the aryl, heteroaryl, and heterocycloalkyl are each independently unsubstituted or substituted by $C_{1-6}$alkyl, $C_{1-6}$alkoxy, $C_{3-8}$ cycloalkyl, R$^3$—$C_{2-7}$heterocycloalkyl or $C_{2-7}$heterocycloalkyl, and R$^3$ is $C_{1-6}$alkyl, $C_{3-6}$ cycloalkyl, or phenyl.

2. The compound of claim 1, wherein
E is phenyl, pyridinyl, quinolinyl, isoquinolinyl, indolyl, isoxazlyl, or pyrazolyl, which is unsubstituted or substituted by 1 to 3 substituents selected from the group consisting of halogen, —NO$_2$, —CN, —NH$_2$, —OH, —CF$_3$, $C_{1-6}$alkyl, $C_{3-8}$cycloalkyl, —(CH$_2$)$_n$—$C_{1-6}$alkylamino, —(CH$_2$)$_n$-di$C_{1-6}$alkylamino, —(CH$_2$)$_n$$C_{1-6}$alkoxy, —(CH$_2$)$_n$—OS(═O)$_2$—$C_{1-6}$alkyl, —(CH$_2$)$_n$—$C_{3-14}$aryl, —(CH$_2$)$_n$—$C_{2-13}$heteroaryl and —(CH$_2$)$_n$—$C_{2-13}$heterocycloalkyl, wherein n is an integer number of 0 to 3.

3. The compound of claim 2, wherein
aryl is phenyl;
heteroaryl is pyrrolyl or imidazolyl; and
heterocycloalkyl is pyrrolidinyl, piperidinyl, piperazinyl, morpholinyl, or diazepanyl,
wherein said aryl, heteroaryl and heterocycloalkyl are each independently unsubstituted or substituted by $C_{1-6}$alkyl, halogen, di$C_{1-6}$alkylamino or $C_{1-6}$alkoxy.

4. The compound of claim 1, wherein
Z is H, methyl, ethyl, 2-hydroxyethyl, 2-morpholinoethyl, isopropyl, cyclopropyl, cyclopentyl, cyclopropylcarbonyl, benzoyl, phenyl, 4-methoxyphenyl, 4-(4-methylpiperidine-1-yl)phenyl, 4-(4-ethylpiperazin-1-yl)phenyl, pyridine-4-yl, pyridine-2-yl, 5-methylpyridine-2-yl, or 6-methylpyridine-3-yl.

5. The compound of claim 1, which is selected from the group consisting of:
1) (E)-3-(2-(4-aminothieno[3,2-d]pyrimidine-7-yl)vinyl)-4-methyl-N-(3-(trifluoromethyl)phenyl)benzamide;
2) (E)-3-(2-(4-aminothieno[3,2-d]pyrimidine-7-yl)vinyl)-N-(4-((4-ethylpiperazine-1-yl)methyl)-3-(trifluoromethyl)phenyl)-4-methylbenzamide;
3) (E)-3-(2-(4-aminothieno[3,2-d]pyrimidine-7-yl)vinyl)-N-(3-(4-ethylpiperazine-1-yl)-5-(trifluoromethyl)phenyl)-4-methylbenzamide;
4) (E)-N-(3-(2-(4-aminothieno[3,2-d]pyrimidine-7-yl)vinyl)-4-methylphenyl)-3-(4-methyl-1H-imidazole-1-yl)-5-(trifluoromethyl)benzamide;
5) (E)-N-(3-(2-(4-aminothieno[3,2-d]pyrimidine-7-yl)vinyl)-4-methylphenyl)-4-(1-methylpiperidine-4-yloxy)-3-(trifluoromethyl)benzamide;
6) (E)-N-(3-(2-(4-aminothieno[3,2-d]pyrimidine-7-yl)vinyl)-4-methylphenyl)-3-(trifluoromethyl)benzamide;
7) (E)-N-(3-(2-(4-aminothieno[3,2-d]pyrimidine-7-yl)vinyl)-4-methylphenyl)-4-((4-ethylpiperazin-1-yl)methyl)-3-(trifluoromethyl)benzamide;

8) 4-amino-N-(2-methyl-5-(3-(trifluoromethyl)phenylcarbamoyl)phenyl)thieno[3,2-d]pyrimidine-7-carboxamide;
9) 4-amino-N-(5-(3-methoxyphenylcarbamoyl)-2-methylphenyl)thieno[3,2-d]pyrimidine-7-carboxamide;
10) 4-amino-N-(2-methyl-5-(3-(4-methyl-1H-imidazole-1-yl)-5-(trifluoromethyl)phenylcarbamoyl)phenyl)thieno[3,2-d]pyrimidine-7-carboxamide;
11) 4-amino-N-(5-(4-((4-ethylpiperazin-1-yl)methyl)-3-(trifluoromethyl)phenylcarbamoyl)-2-methylphenyl)thieno[3,2-d]pyrimidine-7-carboxamide;
12) 4-amino-N-(5-(3,5-dimethoxyphenylcarbamoyl)-2-methylphenyl)thieno[3,2-d]pyrimidine-7-carboxamide;
13) 4-(4-methoxyphenylamino)-N-(2-methyl-5-(3-(trifluoromethyl)phenylcarbamoyl)phenyl)thieno[3,2-d]pyrimidine-7-carboxamide;
14) N-(2-methyl-5-(3-(trifluoromethyl)phenylcarbamoyl)phenyl)-4-(3,4,5-trimethoxyphenylamino)thieno[3,2-d]pyrimidine-7-carboxamide;
15) N-(2-methyl-5-(3-(trifluoromethyl)phenylcarbamoyl)phenyl)-4-(6-methylpyridine-3-ylamino)thieno[3,2-d]pyrimidine-7-carboxamide;
16) 4-(4-(4-ethylpiperazin-1-yl)phenylamino)-N-(2-methyl-5-(3-(trifluoromethyl)phenylcarbamoyl)phenyl)thieno[3,2-d]pyrimidine-7-carboxamide;
17) 4-(isopropylamino)-N-(2-methyl-5-(3-(trifluoromethyl)phenylcarbamoyl)phenyl)thieno[3,2-d]pyrimidine-7-carboxamide;
18) N-(2-methyl-5-(3-(trifluoromethyl)phenylcarbamoyl)phenyl)-4-(methylamino)thieno[3,2-d]pyrimidine-7-carboxamide;
19) 4-(2-hydroxyethylamino)-N-(2-methyl-5-(3-(trifluoromethyl)phenylcarbamoyl)phenyl)thieno[3,2-d]pyrimidine-7-carboxamide;
20) N-(2-methyl-5-(3-(trifluoromethyl)phenylcarbamoyl)phenyl)-4-(2-morpholinoethylamino)thieno[3,2-d]pyrimidine-7-carboxamide; 21) 4-(cyclopropylamino)-N-(2-methyl-5-(3-(trifluoromethyl)phenylcarbamoyl)phenyl)thieno[3,2-d]pyrimidine-7-carboxamide;
22) 4-(cyclopropylamino)-N-(2-methyl-5-(3-(2-methyl-1H-imidazole-1-yl)-5-(trifluoromethyl)phenylcarbamoyl)phenyl)thieno[3,2-d]pyrimidine-7-carboxamide;
23) 4-(3-(4-(cyclopropylamino)thieno[3,2-d]pyrimidine-7-carboxamido)-4-methylbenzamido)-2-(trifluoromethyl)benzyl acetate;
24) 4-(cyclopropylamino)-N-(5-(4-(hydroxymethyl)-3-(trifluoromethyl)phenylcarbamoyl)-2-methylphenyl)thieno[3,2-d]pyrimidine-7-carboxamide;
25) 4-(3-(4-(cyclopropylamino)thieno[3,2-d]pyrimidine-7-carboxamido)-4-methylbenzamido)-2-(trifluoromethyl)benzyl methanesulfonate;
26) 4-(cyclopropylamino)-N-(2-methyl-5-(4-((4-methyl-1H-imidazole-1-yl)methyl)-3-(trifluoromethyl)phenylcarbamoyl)phenyl)thieno[3,2-d]pyrimidine-7-carboxamide;
27) 4-(cyclopropylamino)-N-(2-methyl-5-(3-(4-methyl-1H-imidazole-1-yl)-5-(trifluoromethyl)phenylcarbamoyl)phenyl)thieno[3,2-d]pyrimidine-7-carboxamide;
28) N-(5-(3-bromo-5-(trifluoromethylcarbamoyl)phenyl)-2-methylphenyl)-4-(cyclopropylamino)thieno[3,2-d]pyrimidine-7-carboxamide; 29) 4-(cyclopropylamino)-N-(2-methyl-5-(6-morpholinopyridine-3-ylcarbamoyl)phenyl)thieno[3,2-d]pyrimidine-7-carboxamide;
30) 4-(cyclopropylamino)-N-(5-(6-(4-ethylpiperazine-1-yl)pyridine-3-ylcarbamoyl)-2-methylphenyl)thieno[3,2-d]pyrimidine-7-carboxamide;
31) 4-(cyclopropylamino)-N-(5-(3-(2,4-dimethyl-1H-imidazole-1-yl)-5-(trifluoromethyl)phenylcarbamoyl)-2-methylphenyl)thieno[3,2-d]pyrimidine-7-carboxamide;
32) 4-(cyclopropylamino)-N-(2-methyl-5-(4-((4-methyl-1,4-diazepan-1-yl)methyl)-3-(trifluoromethyl)phenylcarbamoyl)phenyl)thieno[3,2-d]pyrimidine-7-carboxamide;
33) (S)-4-(cyclopropylamino)-N-(5-(4-((3-(dimethylamino)pyrrolidine-1-yl)methyl)-3-(trifluoromethyl)phenylcarbamoyl)-2-methylphenyl)thieno[3,2-d]pyrimidine-7-carboxamide;
34) 4-(cyclopropylamino)-N-(5-(3-(4-hydroxymethyl)-1H-imidazole-1-yl)-5-(trifluoromethyl)phenylcarbamoyl)-2-methylphenyl)thieno[3,2-d]pyrimidine-7-carboxamide;
35) 4-(cyclopropylamino)-N-(2-methyl-5-(4-(1-methylpiperidine-4-yloxy)-3-(trifluoromethyl)phenylcarbamoyl)phenyl)thieno[3,2-d]pyrimidine-7-carboxamide;
36) 4-(cyclopropylamino)-N-(2-methoxy-5-(3-(4-methyl-1H-imidazole-1-yl)-5-(trifluoromethyl)phenylcarbamoyl)phenyl)thieno[3,2-d]pyrimidine-7-carboxamide;
37) 4-(cyclopropylamino)-N-(2-methyl-5-(4-((4-methylpiperazine-1-yl)methyl)-3-(trifluoromethyl)phenylcarbamoyl)phenyl)thieno[3,2-d]pyrimidine-7-carboxamide;
38) 4-(cyclopropylamino)-N-(5-(4-((4-ethylpiperazine-1-yl)methyl)-3-(trifluoromethyl)phenylcarbamoyl)-2-methylphenyl)thieno[3,2-d]pyrimidine-7-carboxamide;
39) 4-amino-N-(2-methyl-5-(3-(trifluoromethyl)benzamido)phenyl)thieno[3,2-d]pyrimidine-7-carboxamide;
40) 4-(cyclopropylamino)-N-(2-methyl-5-(4-morpholino-3-(trifluoromethyl)benzamido)phenyl)thieno[3,2-d]pyrimidine-7-carboxamide;
41) 4-(cyclopropylamino)-N-(5-(3-(3-(dimethylamino)propylamino)-5-(trifluoromethyl)benzamido)-2-methylphenyl)thieno[3,2-d]pyrimidine-7-carboxamide;
42) 4-amino-N-(5-benzamido-2-methylphenyl)thieno[3,2-d]pyrimidine-7-carboxamide;
43) 4-amino-N-(5-(3,5-dimethoxybenzamido)-2-methylphenyl)thieno[3,2-d]pyrimidine-7-carboxamide;
44) N-(5-benzamido-2-methylphenyl)-4-(5-methylpyridin-2-ylamino)thieno[3,2-d]pyrimidine-7-carboxamide;
45) N-(5-(3-(1H-pyrrol-1-yl)-5-(trifluoromethyl)benzamido)-2-methylphenyl)-4-aminothieno[3,2-d]pyrimidine-7-carboxamide; 46) 4-amino-N-(5-(3-(dimethylamino)-5-(trifluoromethyl)benzamido)-2-methylphenyl)thieno[3,2-d]pyrimidine-7-carboxamide;
47) N-(5-(3-(1H-imidazol-1-yl)-5-(trifluoromethyl)benzamido)-2-methylphenyl)-4-aminothieno[3,2-d]pyrimidine-7-carboxamide;
48) 4-amino-N-(5-(3-fluoro-5-(trifluoromethyl)benzamido)-2-methylphenyl)thieno[3,2-d]pyrimidine-7-carboxamide;
49) 4-amino-N-(5-(4-((4-ethylpiperazine-1-yl)methyl)-3-(trifluoromethyl)benzamido)-2-methylphenyl)thieno[3,2-d]pyrimidine-7-carboxamide;
50) 1-(4-(3-(4-aminothieno[3,2-d]pyrimidine-7-carboxyamido)-4-methylphenylcarbamoyl)-2-(trifluoromethyl)benzyl)piperidine-4-yl acetate;
51) N-(2-methyl-5-(3-(trifluoromethyl)benzamido)phenyl)-4-(phenylamino)thieno[3,2-d]pyrimidine-7-carboxamide;

52) N-(2-methyl-5-(3-(trifluoromethyl)benzamido)phenyl)-4-(pyridine-4-ylamino)thieno[3,2-d]pyrimidine-7-carboxamide;
53) N-(2-methyl-5-(3-(trifluoromethyl)benzamido)phenyl)-4-(pyridine-2-ylamino)thieno[3,2-d]pyrimidine-7-carboxamide;
54) 4-amino-N-(5-(isoquinoline-1-carboxyamido)-2-methylphenyl)thieno[3,2-d]pyrimidine-7-carboxamide;
55) 4-amino-N-(5-(isoquinoline-3-carboxyamido)-2-methylphenyl)thieno[3,2-d]pyrimidine-7-carboxamide;
56) 4-amino-N-(5-(4-methoxyquinoline-2-carboxyamido)-2-methylphenyl)thieno[3,2-d]pyrimidine-7-carboxamide;
57) N-(5-(1H-indole-2-carboxyamido)-2-methylphenyl)-4-aminothieno[3,2-d]pyrimidine-7-carboxamide;
58) 4-amino-N-(2-methyl-5-(picolinamido)phenyl)thieno[3,2-d]pyrimidine-7-carboxamide;
59) 4-amino-N-(2-methyl-5-(nicotinamido)phenyl)thieno[3,2-d]pyrimidine-7-carboxamide;
60) 4-amino-N-(5-(isonicotinamido)-2-methylphenyl)thieno[3,2-d]pyrimidine-7-carboxamide;
61) 4-amino-N-(2-methyl-5-(3-(2-methyl-1H-imidazole-1-yl)-5-(trifluoromethyl)benzamido)phenyl)thieno[3,2-d]pyrimidine-7-carboxamide;
62) 4-amino-N-(5-(3-fluorophenylamido)-2-methylphenyl)thieno[3,2-d]pyrimidine-7-carboxamide;
63) 4-amino-N-(2-methyl-5-(2-(trifluoromethyl)benzamido)phenyl)thieno[3,2-d]pyrimidine-7-carboxamide;
64) (R)-4-amino-N-(5-(3-(3-(dimethylamino)pyrrolidine-1-yl)-5-(trifluoromethyl)benzamido)-2-methylphenyl)thieno[3,2-d]pyrimidine-7-carboxamide;
65) 4-amino-N-(5-(3-methoxybenzamido)-2-methylphenyl)thieno[3,2-d]pyrimidine-7-carboxamide;
66) 4-amino-N-(2-methyl-5-(4-(trifluoromethyl)benzamido)phenyl)thieno[3,2-d]pyrimidine-7-carboxamide;
67) N-(3-(4-aminothieno[3,2-d]pyrimidine-7-carboxyamido)-4-methylphenyl)-5-cyclopropylisoxazol-3-carboxamide;
68) 4-amino-N-(5-(1-(4-fluorobenzyl)-3-methyl-1H-pyrazole-5-carboxyamido)-2-methylphenyl)thieno[3,2-d]pyrimidine-7-carboxamide;
69) N-(2-methyl-5-(3-(trifluoromethyl)benzamido)phenyl)-4-(methylamino)thieno[3,2-d]pyrimidine-7-carboxamide;
70) 4-(cycloamino)-N-(2-methyl-5-(3-(trifluoromethyl)benzamido)phenyl)thieno[3,2-d]pyrimidine-7-carboxamide;
71) 4-(cyclopentylamino)-N-(2-methyl-5-(3-(trifluoromethyl)benzamido)phenyl)thieno[3,2-d]pyrimidine-7-carboxamide;
72) N-(2-methyl-5-(3-(trifluoromethyl)benzamido)phenyl)-4-(6-methylpyridine-3-ylamino)thieno[3,2-d]pyrimidine-7-carboxamide;
73) 4-(4-(4-ethylpiperazine-1-yl)phenylamino)-N-(2-methyl-5-(3-(trifluoromethyl)benzamido)phenyl)thieno[3,2-d]pyrimidine-7-carboxamide;
74) 4-(cyclopropylamino)-N-(2-methyl-5-(3-(4-methyl-1H-imidazole-1-yl)-5-(trifluoromethyl)benzamido)phenyl)thieno[3,2-d]pyrimidine-7-carboxamide;
75) 4-(cyclopropylamino)-N-(2-methyl-5-(4-(4-methylpiperazin-1-yl)-3-(trifluoromethyl)benzamido)phenyl)thieno[3,2-d]pyrimidine-7-carboxamide;
76) (S)-4-(cyclopropylamino)-N-(5-(4-((3-(dimethylamino)pyrrolidin-1-yl)methyl)-3-(trifluoromethyl)benzamido)-2-methylphenyl)thieno[3,2-d]pyrimidine-7-carboxamide;
77) 4-(cyclopropylamino)-N-(2-methyl-5-(4-((4-methyl-1H-imidazole-1-yl)methyl)-3-(trifluoromethyl)benzoamido)phenyl)thieno[3,2-d]pyrimidine-7-carboxamide;
78) N-(2-methyl-5-(3-(4-methyl-1H-imidazole-1-yl)-5-(trifluoromethyl)benzoamido)phenyl)-4-(methylamino)thieno[3,2-d]pyrimidine-7-carboxamide;
79) 4-(ethylamino)-N-(2-methyl-5-(3-(4-methyl-1H-imidazole-1-yl)-5-(trifluoromethyl)benzoamido)phenyl)thieno[3,2-d]pyrimidine-7-carboxamide;
80) 4-(cyclopentylamino)-N-(2-methyl-5-(3-(4-methyl-1H-imidazole-1-yl)-5-(trifluoromethyl)benzoamido)phenyl)thieno[3,2-d]pyrimidine-7-carboxamide;
81) N-(2-methyl-5-(3-(4-methyl-1H-imidazole-1-yl)-5-(trifluoromethyl)benzoamido)phenyl)-4-(4-(4-methylpiperazin-1-yl)phenylamino)thieno[3,2-d]pyrimidine-7-carboxamide;
82) 4-(cyclopropylamino)-N-(2-methyl-5-(4-(4-methyl-1H-imidazole-1-yl)-3-(trifluoromethyl)benzoamido)phenyl)thieno[3,2-d]pyrimidine-7-carboxamide;
83) 4-(cyclopropylamino)-N-(2-methyl-5-(3-(2-methyl-1H-imidazole-1-yl)-5-(trifluoromethyl)benzoamido)phenyl)thieno[3,2-d]pyrimidine-7-carboxamide;
84) (R)-4-(cyclopropylamino)-N-(5-(3-(3-(dimethylamino)pyrrolidine-1-yl)-5-(trifluoromethyl)benzoamido)-2-methylphenyl)thieno[3,2-d]pyrimidine-7-carboxamide;
85) 4-(cyclopropylamino)-N-(2-methyl-5-(3-(4-methylpiperazin-1-yl)-5-(trifluoromethyl)benzoamido)phenyl)thieno[3,2-d]pyrimidine-7-carboxamide;
86) 4-(cyclopropylamino)-N-(2-methyl-5-(3-(morpholino-5-(trifluoromethyl)benzoamido)phenyl)thieno[3,2-d]pyrimidine-7-carboxamide;
87) 4-(cyclopropylamino)-N-(2-methyl-5-(4-((4-methyl-1,4-diazepan-1-yl)methyl)-3-(trifluoromethyl)benzoamido)phenyl)thieno[3,2-d]pyrimidine-7-carboxamide;
88) 4-(cyclopropylamino)-N-(5-(4-(2,4-dimethyl-1H-imidazole-1-yl)-3-(trifluoromethyl)benzoamido)-2-methylphenyl)thieno[3,2-d]pyrimidine-7-carboxamide;
89) 4-(cyclopropylamino)-N-(2-fluoro-5-(3-(4-methyl-1,4-diazepane-1-yl)-5-(trifluoromethyl)benzoamido)phenyl)thieno[3,2-d]pyrimidine-7-carboxamide;
90) 4-(cyclopropylamino)-N-(5-(3-(2,4-dimethyl-1H-imidazole-1-yl)-5-(trifluoromethyl)benzoamido)-2-methylphenyl)thieno[3,2-d]pyrimidine-7-carboxamide;
91) N-(5-(3-(1H-imidazole-1-yl)-5-(trifluoromethyl)benzoamido)-2-methylphenyl)-4-(cyclopropylamino)thieno[3,2-d]pyrimidine-7-carboxamide;
92) (S)-4-(cyclopropylamino)-N-(5-(3-(3-(dimethylamino)pyrrolidin-1-yl)-5-(trifluoromethyl)benzoamido)-2-methylphenyl)thieno[3,2-d]pyrimidine-7-carboxamide;
93) 4-(cyclopropylamino)-N-(2-methyl-5-(3-(4-methyl-1,4-diazepan-1-yl)-5-(trifluoromethyl)benzoamido)phenyl)thieno[3,2-d]pyrimidine-7-carboxamide;
94) (R)-4-(cyclopropylamino)-N-(5-(4-(3-(dimethylamino)pyrrolidine-1-yl)-3-(trifluoromethyl)benzoamido)-2-methylphenyl)thieno[3,2-d]pyrimidine-7-carboxamide;
95) (S)-4-(cyclopropylamino)-N-(5-(4-(3-(dimethylamino)pyrrolidine-1-yl)-3-(trifluoromethyl)benzoamido)-2-methylphenyl)thieno[3,2-d]pyrimidine-7-carboxamide;
96) N-(2-methyl-5-(3-(4-methyl-1H-imidazole-1-yl)-5-(trifluoromethyl)benzoamido)phenyl)-4-(1-methylpiperidine-4-ylamino)thieno[3,2-d]pyrimidine-7-carboxamide;

97) 4-(cyclopropylamino)-N-(5-(4-(diethylamino)-3-(trifluoromethyl)benzoamido)-2-methylphenyl)thieno[3,2-d]pyrimidine-7-carboxamide;

98) 4-(cyclopropylamino)-N-(2-methyl-5-(4-(1-methylpiperidine-4-ylamino)-3-(trifluoromethyl)benzoamido)phenyl)thieno[3,2-d]pyrimidine-7-carboxamide;

99) N-(2-chloro-5-(3-(4-methyl-1H-imidazole-1-yl)-5-(trifluoromethyl)benzoamido)phenyl)-4-(cyclopropylamino)thieno[3,2-d]pyrimidine-7-carboxamide;

100) (R)-4-(cyclopropylamino)-N-(5-(4-(3-(dimethylamino)pyrrolidine-1-yl)-3-(trifluoromethyl)benzoamido)-2-fluorophenyl)thieno[3,2-d]pyrimidine-7-carboxamide;

101) N-(2-chloro-5-(3-(2,4-dimethyl-1H-imidazole-1-yl)-5-(trifluoromethyl)benzoamido)phenyl)-4-(cyclopropylamino)thieno[3,2-d]pyrimidine-7-carboxamide;

102) 4-(cyclopropylamino)-N-(2-methyl-5-(3-(morpholinoamino)-5-(trifluoromethyl)benzoamido)phenyl)thieno[3,2-d]pyrimidine-7-carboxamide;

103) N-(2-methyl-5-(3-(4-methyl-1H-imidazole-1-yl)-5-(trifluoromethyl)benzoamido)phenyl)-4-(phenylamino)thieno[3,2-d]pyrimidine-7-carboxamide;

104) 4-(cyclopropylamino)-N-(2-fluoro-5-(4-(4-methylpiperazine-1-yl)-3-(trifluoromethyl)benzoamido)phenyl)thieno[3,2-d]pyrimidine-7-carboxamide;

105) 4-(cyclopropylamino)-N-(5-(3-(2-(dimethylamino)ethylamino)-5-(trifluoromethyl)benzoamido)-2-methylphenyl)thieno[3,2-d]pyrimidine-7-carboxamide;

106) (S)-4-(cyclopropylamino)-N-(5-(4-(3-(dimethylamino)pyrrolidine-1-yl)-3-(trifluoromethyl)benzoamido)-2-fluorophenyl)thieno[3,2-d]pyrimidine-7-carboxamide;

107) (S)-4-(cyclopropylamino)-N-(5-(3-(3-(dimethylamino)pyrrolidine-1-yl)-5-(trifluoromethyl)benzoamido)-2-fluorophenyl)thieno[3,2-d]pyrimidine-7-carboxamide;

108) 4-(cyclopropylamino)-N-(5-(3-(2,4-dimethyl-1H-imidazole-1-yl)-5-(trifluoromethyl)benzoamido)-2-fluorophenyl)thieno[3,2-d]pyrimidine-7-carboxamide;

109) 4-(cyclopropylamino)-N-(2-methyl-5-(3-(piperidine-1-yl)-5-(trifluoromethyl)benzoamido)phenyl)thieno[3,2-d]pyrimidine-7-carboxamide;

110) 4-(cyclopropylamino)-N-(5-(3-(4-ethylpiperazin-1-yl)-5-(trifluoromethyl)benzoamido)-2-methylphenyl)thieno[3,2-d]pyrimidine-7-carboxamide;

111) 4-(cyclopropylamino)-N-(2-methyl-5-(4-(1-methylpiperidine-4-yloxy)-3-(trifluoromethyl)benzoamido)phenyl)thieno[3,2-d]pyrimidine-7-carboxamide;

112) 4-(cyclopropylamino)-N-(2-methyl-5-(3-(pyrrolidine-1-yl)-5-(trifluoromethyl)benzoamido)phenyl)thieno[3,2-d]pyrimidine-7-carboxamide;

113) (R)-4-(cyclopropylamino)-N-(2-methyl-5-(3-(2-methylpyrrolidine-1-yl)-5-(trifluoromethyl)benzoamido)phenyl)thieno[3,2-d]pyrimidine-7-carboxamide;

114) 4-(cyclopropylamino)-N-(5-(3-(diethylamino)-5-(trifluoromethyl)benzoamido)-2-methylphenyl)thieno[3,2-d]pyrimidine-7-carboxamide;

115) 4-(cyclopropylamino)-N-(5-(3-(ethylamino)-5-(trifluoromethyl)benzoamido)-2-methylphenyl)thieno[3,2-d]pyrimidine-7-carboxamide;

116) 4-(cyclopropylamino)-N-(2-methyl-5-(3-(1-methylpiperidine-4-ylamino)-5-(trifluoromethyl)benzoamido)phenyl)thieno[3,2-d]pyrimidine-7-carboxamide;

117) 4-(cyclopropylamino)-N-(3-(3-(4-methyl-1H-imidazole-1-yl)-5-(trifluoromethyl)benzoamido)phenyl)thieno[3,2-d]pyrimidine-7-carboxamide;

118) 4-(cyclopropylamino)-N-(2-methoxy-5-(3-(4-methyl-1H-imidazole-1-yl)-5-(trifluoromethyl)benzoamido)phenyl)thieno[3,2-d]pyrimidine-7-carboxamide;

119) 4-(cyclopropylcarboxyamido)-N-(2-methyl-5-(3-(4-methyl-1H-imidazole-1-yl)-5-(trifluoromethyl)benzoamido)phenyl)thieno[3,2-d]pyrimidine-7-carboxamide;

120) 4-benzoamido-N-(2-methyl-5-(3-(4-methyl-1H-imidazole-1-yl)-5-(trifluoromethyl)benzoamido)phenyl)thieno[3,2-d]pyrimidine-7-carboxamide;

121) 4-(cyclopropylamino)-N-(2-fluoro-5-(3-(4-methyl-1H-imidazole-1-yl)-5-(trifluoromethyl)benzoamido)phenyl)thieno[3,2-d]pyrimidine-7-carboxamide;

122) 4-amino-N-(5-(3-(4-chloro-3-(trifluoromethyl)phenyl)ureido)-2-methylphenyl)thieno[3,2-d]pyrimidine-7-carboxamide;

123) 4-(cyclopropylamino)-N-(2-methyl-5-(3-(3-(4-methyl-1H-imidazole-1-yl)-5-(trifluoromethyl)phenyl)ureido)phenyl)thieno[3,2-d]pyrimidine-7-carboxamide;

124) 3-((4-(cyclopropylamino)thieno[3,2-d]pyrimidine-7-yl)ethynyl)-4-methyl-N-(3-(4-methyl-1H-imidazole-1-yl)-5-(trifluoromethyl)phenyl)benzamide;

125) N-(3-((4-(cyclopropylamino)thieno[3,2-d]pyrimidine-7-yl)ethynyl)-4-methylphenyl)-3-(4-methyl-1H-imidazole-1-yl)-5-(trifluoromethyl)benzamide;

126) 3-((4-(cyclopropylamino)thieno[3,2-d]pyrimidine-7-yl)ethynyl)-4-methyl-N-(4-((4-methylpiperazine-1-yl)methyl)-3-(trifluoromethyl)phenyl)benzamide;

127) 3-((4-(cyclopropylamino)thieno[3,2-d]pyrimidine-7-yl)ethynyl)-N-(4-((4-ethylpiperazine-1-yl)methyl)-3-(trifluoromethyl)phenyl)-4-methylbenzamide;

128) 3-((4-(cyclopropylamino)thieno[3,2-d]pyrimidine-7-yl)ethynyl)-4-methyl-N-(4-(1-methylpiperazine-1-yloxy)-3-(trifluoromethyl)phenyl)benzamide; and a pharmaceutically acceptable salt, thereof.

6. A pharmaceutical composition comprising the compound according to claim 1.

7. A compound of formula (II):

(II)

wherein,

A is halogen, —$OR^4$, —$SR^4$, —$S(=O)R^4$, —$S(=O)_2R^4$, —$NR^4R^5$, or —$NR^4C(=O)R^5$;

$R^4$ and $R^5$ are each independently H, $C_{1-6}$alkyl, $C_{3-8}$cycloalkyl, —$C(=O)R^6$, $C_{2-7}$heterocycloalkyl, $C_{3-14}$aryl, or $C_{2-13}$heteroaryl, wherein the aryl, heteroaryl and heterocycloalkyl are each independently unsubstituted or substituted by the substituent selected from the group consisting of $C_{1-6}$alkyl, $C_{2-7}$cycloalkyl, $C_{1-6}$ alkoxy and $C_{2-7}$heterocycloalkyl; and $R^6$ is H, $C_{1-6}$alkyl or $C_{2-7}$cycloalkyl.

8. A compound of formula (III):

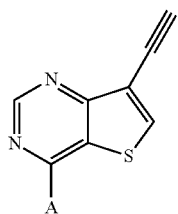

(III)

wherein, A is the same as defined in claim 7.

9. A compound of formula (IV):

(IV)

wherein, A is the same as defined in claim 7.

10. A compound of formula (V):

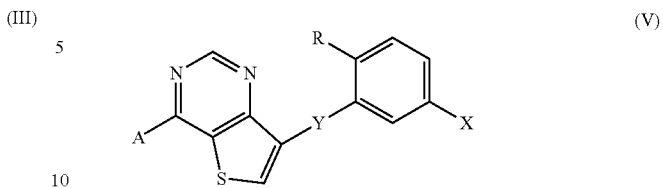

(V)

wherein,
A is the same as defined in claim 7;
X is —$NH_2$ or —C(O)OH;
Y is —$CHR^7$—, —CC—, or —$C(O)NR^7$—, wherein $R^7$ is H, $C_{1-6}$alkyl or $C_{3-8}$cycloalkyl; and
R is H, halogen, methyl or methoxy.

11. A pharmaceutical composition comprising the compound according to claim 2.

12. A pharmaceutical composition comprising the compound according to claim 3.

13. A pharmaceutical composition comprising the compound according to claim 4.

14. A pharmaceutical composition comprising the compound according to claim 5.

* * * * *